United States Patent
Baig et al.

(10) Patent No.: US 11,591,364 B2
(45) Date of Patent: Feb. 28, 2023

(54) SAPONIN PURIFICATION

(71) Applicant: GLAXOSMITHKLINE BIOLOGICALS SA, Rixensart (BE)

(72) Inventors: Ahmad Taimour Baig, Hamilton, MT (US); Felicie Georgette Colette Denet, Pompey, NY (US); Juan Jose Diaz Garcia, Marietta, PA (US); Chad Austin Farrenburg, Hamilton, MT (US); Lora Lea Lawrence, Hamilton, MT (US); Kent Raymond Myers, Hamilton, MT (US); Jeri Kay Sandvick, Hamilton, MT (US); Jeb Yeatts Vandenburg, Hamilton, MT (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 314 days.

(21) Appl. No.: 16/768,402

(22) PCT Filed: Nov. 30, 2018

(86) PCT No.: PCT/EP2018/083234
§ 371 (c)(1),
(2) Date: May 29, 2020

(87) PCT Pub. No.: WO2019/106192
PCT Pub. Date: Jun. 6, 2019

(65) Prior Publication Data
US 2020/0317719 A1 Oct. 8, 2020

Related U.S. Application Data

(60) Provisional application No. 62/593,581, filed on Dec. 1, 2017.

(30) Foreign Application Priority Data

Dec. 21, 2017 (EP) .................................. 17209780

(51) Int. Cl.
| | | |
|---|---|---|
| A61K 39/39 | (2006.01) | |
| C07J 63/00 | (2006.01) | |
| A61K 39/12 | (2006.01) | |
| A61K 39/25 | (2006.01) | |
| C12N 7/00 | (2006.01) | |
| A61K 39/00 | (2006.01) | |

(52) U.S. Cl.
CPC ............ *C07J 63/008* (2013.01); *A61K 39/12* (2013.01); *A61K 39/25* (2013.01); *A61K 39/39* (2013.01); *C12N 7/00* (2013.01); *A61K 2039/55555* (2013.01); *A61K 2039/55577* (2013.01); *C12N 2710/16734* (2013.01); *C12N 2760/18534* (2013.01)

(58) Field of Classification Search
None
See application file for complete search history.

(56) References Cited

U.S. PATENT DOCUMENTS 5,057,540 A 10/1991 Kensil et al.

FOREIGN PATENT DOCUMENTS

| CL | 2011003113 A1 | 8/2012 |
|---|---|---|
| CL | 2020001439 A1 | 2/2021 |
| CL | 2020001440 A1 | 2/2021 |
| JP | 2001505573 A | 4/2001 |
| JP | 2015522643 A | 8/2015 |
| JP | 2020529565 A | 10/2020 |
| JP | 2020529601 A | 10/2020 |
| WO | 1988009336 A1 | 12/1988 |
| WO | 1996032401 A1 | 10/1996 |
| WO | 1998024319 A1 | 6/1998 |
| WO | 9953933 A1 | 10/1999 |
| WO | 2007068907 A2 | 6/2007 |
| WO | 2010142685 A1 | 12/2010 |
| WO | 2014016374 A1 | 1/2014 |
| WO | 2019025520 A1 | 2/2019 |
| WO | 2019047150 A1 | 3/2019 |
| WO | 2019106191 A1 | 6/2019 |
| WO | 2019106192 A1 | 6/2019 |

OTHER PUBLICATIONS

Chaicharoenpong and Petsom, Phytochemical Analysis, Mar. 2009, 20:253-255. (Year: 2009).*
Brunner, Livia, et al., "QS-21 Adjuvant: Laboratory-Scale Purification Method and Formulation Into Liposomes", Chapter 5, Vaccine Adjuvants: Methods in molecular biology (Clifton, N.J.); vol. 1494; pp. 73-86; 2017.
International Search Report and Written Opinion in corresponding International Application No. PCT/EP2018/083234 dated Feb. 14, 2019 (11 pages).
Higuchi et al., "An acylated triterpenoid saponin from Quillaja saponaria", Phytochemistry, 27: 1165-1168 (1988).
Ragupathi et al., "Natural and synthetic saponin adjuvant QS-21 for vaccines against cancer", Expert Review of Vaccines, 10:463-470 (2011).
Thalhamer et al., "Characterization of quillaja bark extracts and evaluation of their purity using liquid chromatography-high resolution mass spectrometry", Phytochemistry Letters, 8: 97-100 (2014).
International Search Report and Written Opinion in corresponding International Application No. PCT/EP2018/083233 dated Mar. 8, 2019, (9 pages).
Gilabert-Oriol Roger et al., "Electrophoretic mobiity as a tool to separate immune adjuvant saponins from Quillaja saponaria Molina", International Journal of Pharmaceutics, Elsevier, NL, vol. 487, No. 1, Mar. 31, 2015 (Mar. 31, 2015), pp. 39-48.

(Continued)

*Primary Examiner* — Stacy B Chen

(57) ABSTRACT

Saponin extracts containing at least 93% QS-21 main peak and 0.25-3% 2018 component by UV absorbance at 214 nm, methods for making said extracts, their use as vaccine adjuvants and related aspects.

32 Claims, 11 Drawing Sheets

Specification includes a Sequence Listing.

(56) References Cited

OTHER PUBLICATIONS

Marty-Roix et al: "Identification of QS-21 as an Inflammasome-activating Molecular Component of Saponin Adjuvants", Journal of Biological Chemistry, vol. 291, No. 3, Jan. 15, 2016 (Jan. 15, 2016), pp. 1123-1136.

Tippel, Janine et al: "Composition of Quillaja saponin extract affects lipid oxidation in oil-in-water emulsions", Food Chemistry, Elsevier Ltd, NL, vol. 221, Oct. 13, 2016 (Oct. 13, 2016), pp. 386-394.

\* cited by examiner

SEQUENCE LISTING

```
<160> NUMBER OF SEQ ID NOS: 9

<210> SEQ ID NO 1
<211> LENGTH: 424
<212> TYPE: PRT
<213> ORGANISM: Artificial
<220> FEATURE:
<223> OTHER INFORMATION: RTS

<400> SEQUENCE: 1

Met Met Ala Pro Asp Pro Asn Ala Asn Pro Asn Ala Asn Pro Asn Ala
1               5                   10                  15

Asn Pro Asn Ala Asn Pro Asn Ala Asn Pro Asn Ala Asn Pro Asn Ala
            20                  25                  30

Asn Pro Asn Ala Asn Pro Asn Ala Asn Pro Asn Ala Asn Pro Asn Ala
        35                  40                  45
```

```
Asn Pro Asn Ala Asn Pro Asn Ala Asn Pro Asn Ala
    50                  55                  60

Asn Pro Asn Ala Asn Pro Asn Ala Asn Pro Asn Lys
65                  70                  75                  80

Asn Asn Gln Gly Asn Gly Gln Gly His Asn Met Pro Asn Asp Pro Asn
                85                  90                  95

Arg Asn Val Asp Glu Asn Ala Asn Ala Asn Ser Ala Val Lys Asn Asn
                100                 105                 110

Asn Asn Glu Glu Pro Ser Asp Lys His Ile Lys Glu Tyr Leu Asn Lys
                115                 120                 125

Ile Gln Asn Ser Leu Ser Thr Glu Trp Ser Pro Cys Ser Val Thr Cys
130                 135                 140

Gly Asn Gly Ile Gln Val Arg Ile Lys Pro Gly Ser Ala Asn Lys Pro
145                 150                 155                 160

Lys Asp Glu Leu Asp Tyr Ala Asn Asp Ile Glu Lys Lys Ile Cys Lys
                165                 170                 175

Met Glu Lys Cys Ser Ser Val Phe Asn Val Val Asn Ser Ser Ile Gly
                180                 185                 190

Leu Gly Pro Val Thr Asn Met Glu Asn Ile Thr Ser Gly Phe Leu Gly
                195                 200                 205

Pro Leu Leu Val Leu Gln Ala Gly Phe Phe Leu Leu Thr Arg Ile Leu
210                 215                 220

Thr Ile Pro Gln Ser Leu Asp Ser Trp Trp Thr Ser Leu Asn Phe Leu
225                 230                 235                 240

Gly Gly Ser Pro Val Cys Leu Gly Gln Asn Ser Gln Ser Pro Thr Ser
                245                 250                 255

Asn His Ser Pro Thr Ser Cys Pro Pro Ile Cys Pro Gly Tyr Arg Trp
                260                 265                 270

Met Cys Leu Arg Arg Phe Ile Ile Phe Leu Phe Ile Leu Leu Leu Cys
                275                 280                 285

Leu Ile Phe Leu Leu Val Leu Leu Asp Tyr Gln Gly Met Leu Pro Val
                290                 295                 300

Cys Pro Leu Ile Pro Gly Ser Thr Thr Thr Asn Thr Gly Pro Cys Lys
305                 310                 315                 320

Thr Cys Thr Thr Pro Ala Gln Gly Asn Ser Met Phe Pro Ser Cys Cys
                325                 330                 335

Cys Thr Lys Pro Thr Asp Gly Asn Cys Thr Cys Ile Pro Ile Pro Ser
                340                 345                 350

Ser Trp Ala Phe Ala Lys Tyr Leu Trp Glu Trp Ala Ser Val Arg Phe
                355                 360                 365

Ser Trp Leu Ser Leu Leu Val Pro Phe Val Gln Trp Phe Val Gly Leu
                370                 375                 380

Ser Pro Thr Val Trp Leu Ser Ala Ile Trp Met Met Trp Tyr Trp Gly
385                 390                 395                 400

Pro Ser Leu Tyr Ser Ile Val Ser Pro Phe Ile Pro Leu Leu Pro Ile
                405                 410                 415

Phe Phe Cys Leu Trp Val Tyr Ile
                420

<210> SEQ ID NO 2
<211> LENGTH: 391
<212> TYPE: PRT
<213> ORGANISM: Mycobacterium tuberculosis

<400> SEQUENCE: 2
```

```
Met Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Gln Met Trp
            20                  25                  30

Asp Ser Val Ala Ser Asp Leu Phe Ser Ala Ala Ser Ala Phe Gln Ser
                35                  40                  45

Val Val Trp Gly Leu Thr Val Gly Ser Trp Ile Gly Ser Ser Ala Gly
    50                  55                  60

Leu Met Val Ala Ala Ser Pro Tyr Val Ala Trp Met Ser Val Thr
65                  70                  75                  80

Ala Gly Gln Ala Glu Leu Thr Ala Ala Gln Val Arg Val Ala Ala Ala
                85                  90                  95

Ala Tyr Glu Thr Ala Tyr Gly Leu Thr Val Pro Pro Val Ile Ala
                100                 105                 110

Glu Asn Arg Ala Glu Leu Met Ile Leu Ile Ala Thr Asn Leu Leu Gly
            115                 120                 125

Gln Asn Thr Pro Ala Ile Ala Val Asn Glu Ala Glu Tyr Gly Glu Met
            130                 135                 140

Trp Ala Gln Asp Ala Ala Ala Met Phe Gly Tyr Ala Ala Ala Thr Ala
145                 150                 155                 160

Thr Ala Thr Ala Thr Leu Leu Pro Phe Glu Glu Ala Pro Glu Met Thr
                165                 170                 175

Ser Ala Gly Gly Leu Leu Glu Gln Ala Ala Ala Val Glu Glu Ala Ser
                180                 185                 190

Asp Thr Ala Ala Ala Asn Gln Leu Met Asn Asn Val Pro Gln Ala Leu
                195                 200                 205

Gln Gln Leu Ala Gln Pro Thr Gln Gly Thr Thr Pro Ser Ser Lys Leu
            210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                245                 250                 255

Ser Met Thr Asn Thr Leu Ser Ser Met Leu Lys Gly Phe Ala Pro Ala
            260                 265                 270

Ala Ala Ala Gln Ala Val Gln Thr Ala Ala Gln Asn Gly Val Arg Ala
            275                 280                 285

Met Ser Ser Leu Gly Ser Ser Leu Gly Ser Ser Gly Leu Gly Gly Gly
            290                 295                 300

Val Ala Ala Asn Leu Gly Arg Ala Ala Ser Val Gly Ser Leu Ser Val
305                 310                 315                 320

Pro Gln Ala Trp Ala Ala Ala Asn Gln Ala Val Thr Pro Ala Ala Arg
                325                 330                 335

Ala Leu Pro Leu Thr Ser Leu Thr Ser Ala Ala Glu Arg Gly Pro Gly
                340                 345                 350

Gln Met Leu Gly Gly Leu Pro Val Gly Gln Met Gly Ala Arg Ala Gly
            355                 360                 365

Gly Gly Leu Ser Gly Val Leu Arg Val Pro Pro Arg Pro Tyr Val Met
370                 375                 380

Pro His Ser Pro Ala Ala Gly
385                 390

<210> SEQ ID NO 3
<211> LENGTH: 323
```

<212> TYPE: PRT
<213> ORGANISM: Mycobacterium tuberculosis

<400> SEQUENCE: 3

```
Ala Pro Pro Ala Leu Ser Gln Asp Arg Phe Ala Asp Phe Pro Ala Leu
1               5                   10                  15

Pro Leu Asp Pro Ser Ala Met Val Ala Gln Val Gly Pro Gln Val Val
            20                  25                  30

Asn Ile Asn Thr Lys Leu Gly Tyr Asn Asn Ala Val Gly Ala Gly Thr
        35                  40                  45

Gly Ile Val Ile Asp Pro Asn Gly Val Val Leu Thr Asn Asn His Val
    50                  55                  60

Ile Ala Gly Ala Thr Asp Ile Asn Ala Phe Ser Val Gly Ser Gly Gln
65                  70                  75                  80

Thr Tyr Gly Val Asp Val Gly Tyr Asp Arg Thr Gln Asp Val Ala
                85                  90                  95

Val Leu Gln Leu Arg Gly Ala Gly Gly Leu Pro Ser Ala Ala Ile Gly
            100                 105                 110

Gly Gly Val Ala Val Gly Glu Pro Val Val Ala Met Gly Asn Ser Gly
        115                 120                 125

Gly Gln Gly Gly Thr Pro Arg Ala Val Pro Gly Arg Val Val Ala Leu
    130                 135                 140

Gly Gln Thr Val Gln Ala Ser Asp Ser Leu Thr Gly Ala Glu Glu Thr
145                 150                 155                 160

Leu Asn Gly Leu Ile Gln Phe Asp Ala Ala Ile Gln Pro Gly Asp Ser
                165                 170                 175

Gly Gly Pro Val Val Asn Gly Leu Gly Gln Val Val Gly Met Asn Thr
            180                 185                 190

Ala Ala Ser Asp Asn Phe Gln Leu Ser Gln Gly Gly Gln Gly Phe Ala
        195                 200                 205

Ile Pro Ile Gly Gln Ala Met Ala Ile Ala Gly Gln Ile Arg Ser Gly
    210                 215                 220

Gly Gly Ser Pro Thr Val His Ile Gly Pro Thr Ala Phe Leu Gly Leu
225                 230                 235                 240

Gly Val Val Asp Asn Asn Gly Asn Gly Ala Arg Val Gln Arg Val Val
                245                 250                 255

Gly Ser Ala Pro Ala Ala Ser Leu Gly Ile Ser Thr Gly Asp Val Ile
            260                 265                 270

Thr Ala Val Asp Gly Ala Pro Ile Asn Ser Ala Thr Ala Met Ala Asp
        275                 280                 285

Ala Leu Asn Gly His His Pro Gly Asp Val Ile Ser Val Thr Trp Gln
    290                 295                 300

Thr Lys Ser Gly Gly Thr Arg Thr Gly Asn Val Thr Leu Ala Glu Gly
305                 310                 315                 320

Pro Pro Ala
```

<210> SEQ ID NO 4
<211> LENGTH: 723
<212> TYPE: PRT
<213> ORGANISM: Artificial
<220> FEATURE:
<223> OTHER INFORMATION: M72

<400> SEQUENCE: 4

```
Met Thr Ala Ala Ser Asp Asn Phe Gln Leu Ser Gln Gly Gly Gln Gly
1               5                   10                  15
```

```
Phe Ala Ile Pro Ile Gly Gln Ala Met Ala Ile Ala Gly Gln Ile Arg
         20                  25                  30

Ser Gly Gly Gly Ser Pro Thr Val His Ile Gly Pro Thr Ala Phe Leu
     35                  40                  45

Gly Leu Gly Val Val Asp Asn Asn Gly Asn Gly Ala Arg Val Gln Arg
 50                  55                  60

Val Val Gly Ser Ala Pro Ala Ala Ser Leu Gly Ile Ser Thr Gly Asp
 65                  70                  75                  80

Val Ile Thr Ala Val Asp Gly Ala Pro Ile Asn Ser Ala Thr Ala Met
             85                  90                  95

Ala Asp Ala Leu Asn Gly His His Pro Gly Asp Val Ile Ser Val Thr
             100                 105                 110

Trp Gln Thr Lys Ser Gly Gly Thr Arg Thr Gly Asn Val Thr Leu Ala
         115                 120                 125

Glu Gly Pro Pro Ala Glu Phe Met Val Asp Phe Gly Ala Leu Pro Pro
 130                 135                 140

Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
                 165                 170                 175

Ala Ala Ser Ala Phe Gln Ser Val Val Trp Gly Leu Thr Val Gly Ser
             180                 185                 190

Trp Ile Gly Ser Ser Ala Gly Leu Met Val Ala Ala Ser Pro Tyr
         195                 200                 205

Val Ala Trp Met Ser Val Thr Ala Gly Gln Ala Glu Leu Thr Ala Ala
         210                 215                 220

Gln Val Arg Val Ala Ala Ala Tyr Glu Thr Ala Tyr Gly Leu Thr
225                 230                 235                 240

Val Pro Pro Pro Val Ile Ala Glu Asn Arg Ala Glu Leu Met Ile Leu
             245                 250                 255

Ile Ala Thr Asn Leu Leu Gly Gln Asn Thr Pro Ala Ile Ala Val Asn
             260                 265                 270

Glu Ala Glu Tyr Gly Glu Met Trp Ala Gln Asp Ala Ala Ala Met Phe
         275                 280                 285

Gly Tyr Ala Ala Ala Thr Ala Thr Ala Thr Leu Leu Pro Phe
290                 295                 300

Glu Glu Ala Pro Glu Met Thr Ser Ala Gly Gly Leu Leu Glu Gln Ala
305                 310                 315                 320

Ala Ala Val Glu Glu Ala Ser Asp Thr Ala Ala Asn Gln Leu Met
             325                 330                 335

Asn Asn Val Pro Gln Ala Leu Gln Gln Leu Ala Gln Pro Thr Gln Gly
             340                 345                 350

Thr Thr Pro Ser Ser Lys Leu Gly Leu Trp Lys Thr Val Ser Pro
         355                 360                 365

His Arg Ser Pro Ile Ser Asn Met Val Ser Met Ala Asn Asn His Met
         370                 375                 380

Ser Met Thr Asn Ser Gly Val Ser Met Thr Asn Thr Leu Ser Ser Met
385                 390                 395                 400

Leu Lys Gly Phe Ala Pro Ala Ala Ala Gln Ala Val Gln Thr Ala
                 405                 410                 415

Ala Gln Asn Gly Val Arg Ala Met Ser Ser Leu Gly Ser Ser Leu Gly
             420                 425                 430
```

```
Ser Ser Gly Leu Gly Gly Gly Val Ala Ala Asn Leu Gly Arg Ala Ala
        435                 440                 445

Ser Val Gly Ser Leu Ser Val Pro Gln Ala Trp Ala Ala Ala Asn Gln
    450                 455                 460

Ala Val Thr Pro Ala Ala Arg Ala Leu Pro Leu Thr Ser Leu Thr Ser
465                 470                 475                 480

Ala Ala Glu Arg Gly Pro Gly Gln Met Leu Gly Gly Leu Pro Val Gly
                485                 490                 495

Gln Met Gly Ala Arg Ala Gly Gly Leu Ser Gly Val Leu Arg Val
        500                 505                 510

Pro Pro Arg Pro Tyr Val Met Pro His Ser Pro Ala Ala Gly Asp Ile
        515                 520                 525

Ala Pro Pro Ala Leu Ser Gln Asp Arg Phe Ala Asp Phe Pro Ala Leu
530                 535                 540

Pro Leu Asp Pro Ser Ala Met Val Ala Gln Val Gly Pro Gln Val Val
545                 550                 555                 560

Asn Ile Asn Thr Lys Leu Gly Tyr Asn Asn Ala Val Gly Ala Gly Thr
                565                 570                 575

Gly Ile Val Ile Asp Pro Asn Gly Val Val Leu Thr Asn Asn His Val
            580                 585                 590

Ile Ala Gly Ala Thr Asp Ile Asn Ala Phe Ser Val Gly Ser Gly Gln
            595                 600                 605

Thr Tyr Gly Val Asp Val Val Gly Tyr Asp Arg Thr Gln Asp Val Ala
        610                 615                 620

Val Leu Gln Leu Arg Gly Ala Gly Gly Leu Pro Ser Ala Ala Ile Gly
625                 630                 635                 640

Gly Gly Val Ala Val Gly Glu Pro Val Val Ala Met Gly Asn Ser Gly
                645                 650                 655

Gly Gln Gly Gly Thr Pro Arg Ala Val Pro Gly Arg Val Val Ala Leu
            660                 665                 670

Gly Gln Thr Val Gln Ala Ser Asp Ser Leu Thr Gly Ala Glu Glu Thr
        675                 680                 685

Leu Asn Gly Leu Ile Gln Phe Asp Ala Ala Ile Gln Pro Gly Asp Ala
    690                 695                 700

Gly Gly Pro Val Val Asn Gly Leu Gly Gln Val Val Gly Met Asn Thr
705                 710                 715                 720

Ala Ala Ser

<210> SEQ ID NO 5
<211> LENGTH: 725
<212> TYPE: PRT
<213> ORGANISM: Artificial
<220> FEATURE:
<223> OTHER INFORMATION: M72-2His

<400> SEQUENCE: 5

Met His His Thr Ala Ala Ser Asp Asn Phe Gln Leu Ser Gln Gly Gly
1               5                  10                  15

Gln Gly Phe Ala Ile Pro Ile Gly Gln Ala Met Ala Ile Ala Gly Gln
            20                  25                  30

Ile Arg Ser Gly Gly Gly Ser Pro Thr Val His Ile Gly Pro Thr Ala
        35                  40                  45

Phe Leu Gly Leu Gly Val Val Asp Asn Gly Asn Gly Ala Arg Val
    50                  55                  60

Gln Arg Val Val Gly Ser Ala Pro Ala Ala Ser Leu Gly Ile Ser Thr
```

-continued

```
                65                  70                  75                  80
Gly Asp Val Ile Thr Ala Val Asp Gly Ala Pro Ile Asn Ser Ala Thr
                    85                  90                  95
Ala Met Ala Asp Ala Leu Asn Gly His His Pro Gly Asp Val Ile Ser
                    100                 105                 110
Val Thr Trp Gln Thr Lys Ser Gly Gly Thr Arg Thr Gly Asn Val Thr
                    115                 120                 125
Leu Ala Glu Gly Pro Pro Ala Glu Phe Met Val Asp Phe Gly Ala Leu
                130                 135                 140
Pro Pro Glu Ile Asn Ser Ala Arg Met Tyr Ala Gly Pro Gly Ser Ala
145                 150                 155                 160
Ser Leu Val Ala Ala Ala Gln Met Trp Asp Ser Val Ala Ser Asp Leu
                    165                 170                 175
Phe Ser Ala Ala Ser Ala Phe Gln Ser Val Val Trp Gly Leu Thr Val
                    180                 185                 190
Gly Ser Trp Ile Gly Ser Ser Ala Gly Leu Met Val Ala Ala Ala Ser
                    195                 200                 205
Pro Tyr Val Ala Trp Met Ser Val Thr Ala Gly Gln Ala Glu Leu Thr
                    210                 215                 220
Ala Ala Gln Val Arg Val Ala Ala Ala Tyr Glu Thr Ala Tyr Gly
225                 230                 235                 240
Leu Thr Val Pro Pro Pro Val Ile Ala Glu Asn Arg Ala Glu Leu Met
                    245                 250                 255
Ile Leu Ile Ala Thr Asn Leu Leu Gly Gln Asn Thr Pro Ala Ile Ala
                    260                 265                 270
Val Asn Glu Ala Glu Tyr Gly Glu Met Trp Ala Gln Asp Ala Ala Ala
                    275                 280                 285
Met Phe Gly Tyr Ala Ala Thr Ala Thr Ala Thr Ala Thr Leu Leu
                    290                 295                 300
Pro Phe Glu Glu Ala Pro Glu Met Thr Ser Ala Gly Gly Leu Leu Glu
305                 310                 315                 320
Gln Ala Ala Ala Val Glu Glu Ala Ser Asp Thr Ala Ala Ala Asn Gln
                    325                 330                 335
Leu Met Asn Asn Val Pro Gln Ala Leu Gln Gln Leu Ala Gln Pro Thr
                    340                 345                 350
Gln Gly Thr Thr Pro Ser Ser Lys Leu Gly Gly Leu Trp Lys Thr Val
                    355                 360                 365
Ser Pro His Arg Ser Pro Ile Ser Asn Met Val Ser Met Ala Asn Asn
                    370                 375                 380
His Met Ser Met Thr Asn Ser Gly Val Ser Met Thr Asn Thr Leu Ser
385                 390                 395                 400
Ser Met Leu Lys Gly Phe Ala Pro Ala Ala Ala Gln Ala Val Gln
                    405                 410                 415
Thr Ala Ala Gln Asn Gly Val Arg Ala Met Ser Ser Leu Gly Ser Ser
                    420                 425                 430
Leu Gly Ser Ser Gly Leu Gly Gly Val Ala Ala Asn Leu Gly Arg
                    435                 440                 445
Ala Ala Ser Val Gly Ser Leu Ser Val Pro Gln Ala Trp Ala Ala Ala
                    450                 455                 460
Asn Gln Ala Val Thr Pro Ala Ala Arg Ala Leu Pro Leu Thr Ser Leu
465                 470                 475                 480
Thr Ser Ala Ala Glu Arg Gly Pro Gly Gln Met Leu Gly Gly Leu Pro
                    485                 490                 495
```

Val Gly Gln Met Gly Ala Arg Ala Gly Gly Gly Leu Ser Gly Val Leu
500 505 510

Arg Val Pro Pro Arg Pro Tyr Val Met Pro His Ser Pro Ala Ala Gly
515 520 525

Asp Ile Ala Pro Pro Ala Leu Ser Gln Asp Arg Phe Ala Asp Phe Pro
530 535 540

Ala Leu Pro Leu Asp Pro Ser Ala Met Val Ala Gln Val Gly Pro Gln
545 550 555 560

Val Val Asn Ile Asn Thr Lys Leu Gly Tyr Asn Asn Ala Val Gly Ala
565 570 575

Gly Thr Gly Ile Val Ile Asp Pro Asn Gly Val Val Leu Thr Asn Asn
580 585 590

His Val Ile Ala Gly Ala Thr Asp Ile Asn Ala Phe Ser Val Gly Ser
595 600 605

Gly Gln Thr Tyr Gly Val Asp Val Val Gly Tyr Asp Arg Thr Gln Asp
610 615 620

Val Ala Val Leu Gln Leu Arg Gly Ala Gly Gly Leu Pro Ser Ala Ala
625 630 635 640

Ile Gly Gly Gly Val Ala Val Gly Glu Pro Val Val Ala Met Gly Asn
645 650 655

Ser Gly Gly Gln Gly Gly Thr Pro Arg Ala Val Pro Gly Arg Val Val
660 665 670

Ala Leu Gly Gln Thr Val Gln Ala Ser Asp Ser Leu Thr Gly Ala Glu
675 680 685

Glu Thr Leu Asn Gly Leu Ile Gln Phe Asp Ala Ala Ile Gln Pro Gly
690 695 700

Asp Ala Gly Gly Pro Val Val Asn Gly Leu Gly Gln Val Val Gly Met
705 710 715 720

Asn Thr Ala Ala Ser
725

<210> SEQ ID NO 6
<211> LENGTH: 546
<212> TYPE: PRT
<213> ORGANISM: Varicella zoster

<400> SEQUENCE: 6

Met Gly Thr Val Asn Lys Pro Val Val Gly Val Leu Met Gly Phe Gly
1 5 10 15

Ile Ile Thr Gly Thr Leu Arg Ile Thr Asn Pro Val Arg Ala Ser Val
20 25 30

Leu Arg Tyr Asp Asp Phe His Ile Asp Glu Asp Lys Leu Asp Thr Asn
35 40 45

Ser Val Tyr Glu Pro Tyr Tyr His Ser Asp His Ala Glu Ser Ser Trp
50 55 60

Val Asn Arg Gly Glu Ser Ser Arg Lys Ala Tyr Asp His Asn Ser Pro
65 70 75 80

Tyr Ile Trp Pro Arg Asn Asp Tyr Asp Gly Phe Leu Glu Asn Ala His
85 90 95

Glu His His Gly Val Tyr Asn Gln Gly Arg Gly Ile Asp Ser Gly Glu
100 105 110

Arg Leu Met Gln Pro Thr Gln Met Ser Ala Gln Glu Asp Leu Gly Asp
115 120 125

Asp Thr Gly Ile His Val Ile Pro Thr Leu Asn Gly Asp Asp Arg His

```
            130                 135                 140
Lys Ile Val Asn Val Asp Gln Arg Gln Tyr Gly Asp Val Phe Lys Gly
145                 150                 155                 160
Asp Leu Asn Pro Lys Pro Gln Gly Gln Arg Leu Ile Glu Val Ser Val
                165                 170                 175
Glu Glu Asn His Pro Phe Thr Leu Arg Ala Pro Ile Gln Arg Ile Tyr
                180                 185                 190
Gly Val Arg Tyr Thr Glu Thr Trp Ser Phe Leu Pro Ser Leu Thr Cys
            195                 200                 205
Thr Gly Asp Ala Ala Pro Ala Ile Gln His Ile Cys Leu Lys His Thr
    210                 215                 220
Thr Cys Phe Gln Asp Val Val Asp Val Asp Cys Ala Glu Asn Thr
225                 230                 235                 240
Lys Glu Asp Gln Leu Ala Glu Ile Ser Tyr Arg Phe Gln Gly Lys Lys
                245                 250                 255
Glu Ala Asp Gln Pro Trp Ile Val Val Asn Thr Ser Thr Leu Phe Asp
                260                 265                 270
Glu Leu Glu Leu Asp Pro Pro Glu Ile Glu Pro Gly Val Leu Lys Val
            275                 280                 285
Leu Arg Thr Glu Lys Gln Tyr Leu Gly Val Tyr Ile Trp Asn Met Arg
    290                 295                 300
Gly Ser Asp Gly Thr Ser Thr Tyr Ala Thr Phe Leu Val Thr Trp Lys
305                 310                 315                 320
Gly Asp Glu Lys Thr Arg Asn Pro Thr Pro Ala Val Thr Pro Gln Pro
                325                 330                 335
Arg Gly Ala Glu Phe His Met Trp Asn Tyr His Ser His Val Phe Ser
                340                 345                 350
Val Gly Asp Thr Phe Ser Leu Ala Met His Leu Gln Tyr Lys Ile His
            355                 360                 365
Glu Ala Pro Phe Asp Leu Leu Leu Glu Trp Leu Tyr Val Pro Ile Asp
    370                 375                 380
Pro Thr Cys Gln Pro Met Arg Leu Tyr Ser Thr Cys Leu Tyr His Pro
385                 390                 395                 400
Asn Ala Pro Gln Cys Leu Ser His Met Asn Ser Gly Cys Thr Phe Thr
                405                 410                 415
Ser Pro His Leu Ala Gln Arg Val Ala Ser Thr Val Tyr Gln Asn Cys
                420                 425                 430
Glu His Ala Asp Asn Tyr Thr Ala Tyr Cys Leu Gly Ile Ser His Met
            435                 440                 445
Glu Pro Ser Phe Gly Leu Ile Leu His Asp Gly Thr Thr Leu Lys
    450                 455                 460
Phe Val Asp Thr Pro Glu Ser Leu Ser Gly Leu Tyr Val Phe Val Val
465                 470                 475                 480
Tyr Phe Asn Gly His Val Glu Ala Val Ala Tyr Thr Val Val Ser Thr
                485                 490                 495
Val Asp His Phe Val Asn Ala Ile Glu Glu Arg Gly Phe Pro Pro Thr
            500                 505                 510
Ala Gly Gln Pro Pro Ala Thr Thr Lys Pro Lys Glu Ile Thr Pro Val
    515                 520                 525
Asn Pro Gly Thr Ser Pro Leu Ile Arg Tyr Ala Ala Trp Gly Gly
    530                 535                 540
Leu Ala
545
```

<210> SEQ ID NO 7
<211> LENGTH: 514
<212> TYPE: PRT
<213> ORGANISM: respiratory syncytial virus

<400> SEQUENCE: 7

```
Met Glu Leu Leu Ile Leu Lys Thr Asn Ala Ile Thr Ala Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Ser Ala Val Thr Glu Leu Gln Leu Leu
                85                  90                  95

Met Gln Ser Thr Pro Ala Thr Asn Asn Lys Phe Leu Gly Phe Leu Gln
            100                 105                 110

Gly Val Gly Ser Ala Ile Ala Ser Gly Ile Ala Val Ser Lys Val Leu
        115                 120                 125

His Leu Glu Gly Glu Val Asn Lys Ile Lys Ser Ala Leu Leu Ser Thr
    130                 135                 140

Asn Lys Ala Val Val Ser Leu Ser Asn Gly Val Ser Val Leu Thr Ser
145                 150                 155                 160

Lys Val Leu Asp Leu Lys Asn Tyr Ile Asp Lys Gln Leu Leu Pro Ile
                165                 170                 175

Val Asn Lys Gln Ser Cys Ser Ile Ser Asn Ile Glu Thr Val Ile Glu
            180                 185                 190

Phe Gln Gln Lys Asn Asn Arg Leu Leu Glu Ile Thr Arg Glu Phe Ser
        195                 200                 205

Val Asn Ala Gly Val Thr Thr Pro Val Ser Thr Tyr Met Leu Thr Asn
    210                 215                 220

Ser Glu Leu Leu Ser Leu Ile Asn Asp Met Pro Ile Thr Asn Asp Gln
225                 230                 235                 240

Lys Lys Leu Met Ser Asn Asn Val Gln Ile Val Arg Gln Gln Ser Tyr
                245                 250                 255

Ser Ile Met Ser Ile Ile Lys Glu Glu Val Leu Ala Tyr Val Val Gln
            260                 265                 270

Leu Pro Leu Tyr Gly Val Ile Asp Thr Pro Cys Trp Lys Leu His Thr
        275                 280                 285

Ser Pro Leu Cys Thr Thr Asn Thr Lys Glu Gly Ser Asn Ile Cys Leu
    290                 295                 300

Thr Arg Thr Asp Arg Gly Trp Tyr Cys Asp Asn Ala Gly Ser Val Ser
305                 310                 315                 320

Phe Phe Pro Leu Ala Glu Thr Cys Lys Val Gln Ser Asn Arg Val Phe
                325                 330                 335

Cys Asp Thr Met Asn Ser Leu Thr Leu Pro Ser Glu Val Asn Leu Cys
            340                 345                 350

Asn Ile Asp Ile Phe Asn Pro Lys Tyr Asp Cys Lys Ile Met Thr Ser
        355                 360                 365

Lys Thr Asp Val Ser Ser Ser Val Ile Thr Ser Leu Gly Ala Ile Val
```

```
                    370                 375                 380
Ser Cys Tyr Gly Lys Thr Lys Cys Thr Ala Ser Asn Lys Asn Arg Gly
385                 390                 395                 400

Ile Ile Lys Thr Phe Ser Asn Gly Cys Asp Tyr Val Ser Asn Lys Gly
                    405                 410                 415

Val Asp Thr Val Ser Val Gly Asn Thr Leu Tyr Val Asn Lys Gln
                420                 425                 430

Glu Gly Lys Ser Leu Tyr Val Lys Gly Glu Pro Ile Ile Asn Phe Tyr
                435                 440                 445

Asp Pro Leu Val Phe Pro Ser Asp Glu Phe Asp Ala Ser Ile Ser Gln
                450                 455                 460

Val Asn Glu Lys Ile Asn Gly Thr Leu Ala Phe Ile Arg Lys Ser Asp
465                 470                 475                 480

Glu Lys Leu His Asn Val Glu Asp Lys Ile Glu Glu Ile Leu Ser Lys
                485                 490                 495

Ile Tyr His Ile Glu Asn Glu Ile Ala Arg Ile Lys Lys Leu Ile Gly
                500                 505                 510

Glu Ala

<210> SEQ ID NO 8
<211> LENGTH: 488
<212> TYPE: PRT
<213> ORGANISM: Human immunodeficiency virus

<400> SEQUENCE: 8

Asn Thr Glu Asp Leu Trp Val Thr Val Tyr Tyr Gly Val Pro Val Trp
1               5                   10                  15

Arg Asp Ala Lys Thr Thr Leu Phe Cys Ala Ser Asp Ala Lys Ala Tyr
                20                  25                  30

Glu Thr Glu Val His Asn Val Trp Ala Thr His Ala Cys Val Pro Thr
                35                  40                  45

Asp Pro Asn Pro Gln Glu Ile Val Leu Gly Asn Val Thr Glu Asn Phe
                50                  55                  60

Asn Met Trp Lys Asn Asp Met Ala Asp Gln Met His Glu Asp Val Ile
65                  70                  75                  80

Ser Leu Trp Asp Gln Ser Leu Lys Pro Cys Val Lys Leu Thr Pro Leu
                85                  90                  95

Cys Val Thr Leu Asn Cys Thr Asp Thr Asn Val Thr Gly Asn Arg Thr
                100                 105                 110

Val Thr Gly Asn Ser Thr Asn Asn Thr Asn Gly Thr Gly Ile Tyr Asn
                115                 120                 125

Ile Glu Glu Met Lys Asn Cys Ser Phe Asn Ala Thr Thr Glu Leu Arg
                130                 135                 140

Asp Lys Lys His Lys Glu Tyr Ala Leu Phe Tyr Arg Leu Asp Ile Val
145                 150                 155                 160

Pro Leu Asn Glu Asn Ser Asp Asn Phe Thr Tyr Arg Leu Ile Asn Cys
                165                 170                 175

Asn Thr Ser Thr Ile Thr Gln Ala Cys Pro Lys Val Ser Phe Asp Pro
                180                 185                 190

Ile Pro Ile His Tyr Cys Ala Pro Ala Gly Tyr Ala Ile Leu Lys Cys
                195                 200                 205

Asn Asn Lys Thr Phe Asn Gly Thr Gly Pro Cys Tyr Asn Val Ser Thr
                210                 215                 220

Val Gln Cys Thr His Gly Ile Lys Pro Val Val Ser Thr Gln Leu Leu
```

```
225                 230                 235                 240

Leu Asn Gly Ser Leu Ala Glu Glu Gly Ile Ile Ile Arg Ser Glu Asn
                245                 250                 255

Leu Thr Glu Asn Thr Lys Thr Ile Ile Val His Leu Asn Glu Ser Val
            260                 265                 270

Glu Ile Asn Cys Thr Arg Pro Asn Asn Thr Arg Lys Ser Val Arg
        275                 280                 285

Ile Gly Pro Gly Gln Ala Phe Tyr Ala Thr Asn Asp Val Ile Gly Asn
    290                 295                 300

Ile Arg Gln Ala His Cys Asn Ile Ser Thr Asp Arg Trp Asn Lys Thr
305                 310                 315                 320

Leu Gln Gln Val Met Lys Lys Leu Gly Glu His Phe Pro Asn Lys Thr
                325                 330                 335

Ile Gln Phe Lys Pro His Ala Gly Gly Asp Leu Glu Ile Thr Met His
            340                 345                 350

Ser Phe Asn Cys Arg Gly Glu Phe Phe Tyr Cys Asn Thr Ser Asn Leu
        355                 360                 365

Phe Asn Ser Thr Tyr His Ser Asn Asn Gly Thr Tyr Lys Tyr Asn Gly
    370                 375                 380

Asn Ser Ser Pro Ile Thr Leu Gln Cys Lys Ile Lys Gln Ile Val
385                 390                 395                 400

Arg Met Trp Gln Gly Val Gly Gln Ala Thr Tyr Ala Pro Pro Ile Ala
                405                 410                 415

Gly Asn Ile Thr Cys Arg Ser Asn Ile Thr Gly Ile Leu Leu Thr Arg
            420                 425                 430

Asp Gly Gly Phe Asn Thr Thr Asn Asn Thr Glu Thr Phe Arg Pro Gly
        435                 440                 445

Gly Gly Asp Met Arg Asp Asn Trp Arg Ser Glu Leu Tyr Lys Tyr Lys
    450                 455                 460

Val Val Glu Ile Lys Pro Leu Gly Ile Ala Pro Thr Lys Ala Lys Arg
465                 470                 475                 480

Arg Val Val Gln Arg Glu Lys Arg
                485

<210> SEQ ID NO 9
<211> LENGTH: 469
<212> TYPE: PRT
<213> ORGANISM: Human immunodeficiency virus

<400> SEQUENCE: 9

Ser Trp Val Thr Val Tyr Tyr Gly Val Pro Val Trp Lys Glu Ala Lys
1               5                   10                  15

Thr Thr Leu Phe Cys Ala Ser Asp Ala Lys Ala Tyr Glu Lys Glu Val
            20                  25                  30

His Asn Val Trp Ala Thr His Ala Cys Val Pro Thr Asp Pro Asn Pro
        35                  40                  45

Gln Glu Met Val Leu Ala Asn Val Thr Glu Asn Phe Asn Met Trp Lys
    50                  55                  60

Asn Asp Met Val Glu Gln Met His Glu Asp Ile Ile Ser Leu Trp Asp
65                  70                  75                  80

Glu Ser Leu Lys Pro Cys Val Lys Leu Thr Pro Leu Cys Val Thr Leu
                85                  90                  95

Asn Cys Thr Asn Val Lys Gly Asn Glu Ser Asp Thr Ser Glu Val Met
            100                 105                 110
```

```
Lys Asn Cys Ser Phe Lys Ala Thr Thr Glu Leu Lys Asp Lys Lys His
            115                 120                 125

Lys Val His Ala Leu Phe Tyr Lys Leu Asp Val Val Pro Leu Asn Gly
    130                 135                 140

Asn Ser Ser Ser Ser Gly Glu Tyr Arg Leu Ile Asn Cys Asn Thr Ser
145                 150                 155                 160

Ala Ile Thr Gln Ala Cys Pro Lys Val Ser Phe Asp Pro Ile Pro Leu
                165                 170                 175

His Tyr Cys Ala Pro Ala Gly Phe Ala Ile Leu Lys Cys Asn Asn Lys
            180                 185                 190

Thr Phe Asn Gly Thr Gly Pro Cys Arg Asn Val Ser Thr Val Gln Cys
        195                 200                 205

Thr His Gly Ile Lys Pro Val Val Ser Thr Gln Leu Leu Leu Asn Gly
    210                 215                 220

Ser Leu Ala Glu Glu Glu Ile Ile Ile Arg Ser Glu Asn Leu Thr Asn
225                 230                 235                 240

Asn Ala Lys Thr Ile Ile Val His Leu Asn Glu Ser Val Asn Ile Val
                245                 250                 255

Cys Thr Arg Pro Asn Asn Asn Thr Arg Lys Ser Ile Arg Ile Gly Pro
            260                 265                 270

Gly Gln Thr Phe Tyr Ala Thr Gly Asp Ile Ile Gly Asn Ile Arg Gln
        275                 280                 285

Ala His Cys Asn Ile Asn Glu Ser Lys Trp Asn Asn Thr Leu Gln Lys
    290                 295                 300

Val Gly Glu Glu Leu Ala Lys His Phe Pro Ser Lys Thr Ile Lys Phe
305                 310                 315                 320

Glu Pro Ser Ser Gly Gly Asp Leu Glu Ile Thr Thr His Ser Phe Asn
                325                 330                 335

Cys Arg Gly Glu Phe Phe Tyr Cys Asn Thr Ser Asp Leu Phe Asn Gly
            340                 345                 350

Thr Tyr Arg Asn Gly Thr Tyr Asn His Thr Gly Arg Ser Ser Asn Gly
        355                 360                 365

Thr Ile Thr Leu Gln Cys Lys Ile Lys Gln Ile Ile Asn Met Trp Gln
    370                 375                 380

Glu Val Gly Arg Ala Ile Tyr Ala Pro Pro Ile Glu Gly Glu Ile Thr
385                 390                 395                 400

Cys Asn Ser Asn Ile Thr Gly Leu Leu Leu Arg Asp Gly Gly Gln
                405                 410                 415

Ser Asn Glu Thr Asn Asp Thr Glu Thr Phe Arg Pro Gly Gly Gly Asp
            420                 425                 430

Met Arg Asp Asn Trp Arg Ser Glu Leu Tyr Lys Tyr Lys Val Val Glu
        435                 440                 445

Ile Lys Pro Leu Gly Val Ala Pro Thr Glu Ala Lys Arg Arg Val Val
    450                 455                 460

Glu Arg Glu Lys Arg
465
```

SAPONIN PURIFICATION

TECHNICAL FIELD

The present application generally relates to saponin extracts, in particular extracts of *Quillaja saponaria* Molina, methods for their manufacture and to associated aspects.

BACKGROUND

Adjuvants are included in vaccines to improve humoral and cellular immune responses, particularly in the case of poorly immunogenic subunit vaccines. Similar to natural infections by pathogens, adjuvants rely on the activation of the innate immune system to promote long-lasting adaptive immunity.

The Adjuvant System 01 (AS01) is a liposome-based adjuvant which contains two immunostimulants, 3-O-desacyl-4'-monophosphoryl lipid A (3D-MPL) and QS-21 (Garcon and Van Mechelen, 2011; Didierlaurent et al., 2017). 3D-MPL is a non-toxic derivative of the lipopolysaccharide from *Salmonella minnesota* which is a TLR4 agonist) and QS-21 is a natural saponin extract from the bark of the South American tree *Quillaja saponaria* Molina (Kensil et al., 1991; Ragupathi et al., 2011). AS01 is included in the recently developed vaccines for malaria (RTS,S-Mosquirix®) and *Herpes zoster* (HZ/su-Shingrix®), and in multiple candidate vaccines in development against pathogens such as human immunodeficiency virus and *Mycobacterium tuberculosis*.

AS01 injection results in rapid and transient activation of innate immunity in animal models. Neutrophils and monocytes are rapidly recruited to the draining lymph node (dLN) upon immunization. Moreover, AS01 induces recruitment and activation of MHCII$^{high}$ dendritic cells (DC), which are necessary for T cell activation (Didierlaurent A. M. et al., 2014). Some data are also available on the mechanism of action of the components of AS01. 3D-MPL signals via TLR4, stimulating NF-κB transcriptional activity and cytokine production and directly activates antigen-presenting cells (APCs) both in humans and in mice (De Becker et al., 2000; Ismaili et al., 2002; Martin et al., 2003; Mata-Haro et al., 2007). QS-21 promotes high antigen-specific antibody responses and CD8$^+$ T-cell responses in mice (Kensil and Kammer, 1998; Newman et al., 1992; Soltysik et al., 1995) and antigen-specific antibody responses in humans (Livingston et al., 1994). Because of its physical properties, it is thought that QS-21 might act as a danger signal in vivo (Lambrecht et al., 2009; Li et al., 2008). Although QS-21 has been shown to activate ASC-NLRP3 inflammasome and subsequent IL-1β/IL-18 release (Marty-Roix, R. et al., 2016), the exact molecular pathways involved in the adjuvant effect of saponins have yet to be clearly defined.

As with any component of a product which is approved as a human medicament, production of QS-21 requires the use of approved manufacturing processes and careful control of final composition to ensure that it meets the required specification. Modification of existing processes requires costly and time consuming re-validation, yet deviations from specification also result in waste. There is a continuing need for robust methods for the manufacture of QS-21 and for QS-21 material of defined composition.

SUMMARY OF THE INVENTION

The present invention provides a saponin extract containing at least 93% QS-21 main peak and 0.25-3% 2018 component by UV absorbance at 214 nm.

Also provided is a saponin extract containing at least 93% by UV absorbance at 214 nm triterpenoid glycosides having by negative ion electrospray mass spectrometry m/z of 1855.9, 1987.9 or 2001.9, and 0.25-3% by UV absorbance at 214 nm triterpenoid glycosides having m/z 2017.9.

Additionally provided is a saponin extract containing at least 93%:

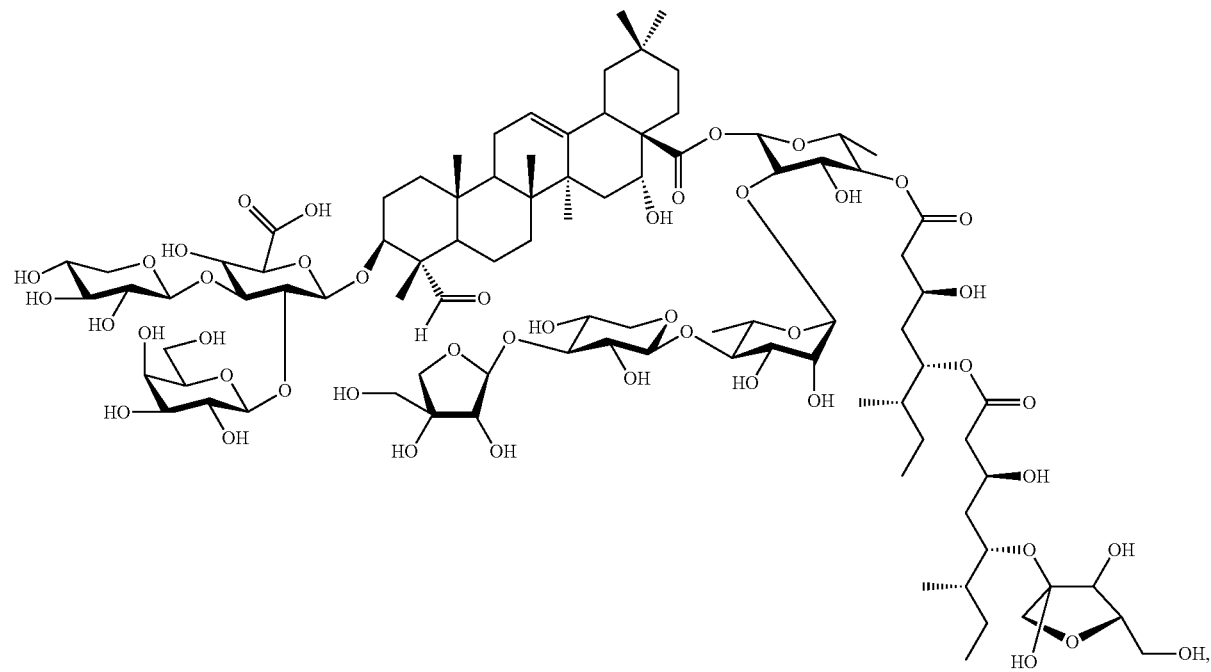

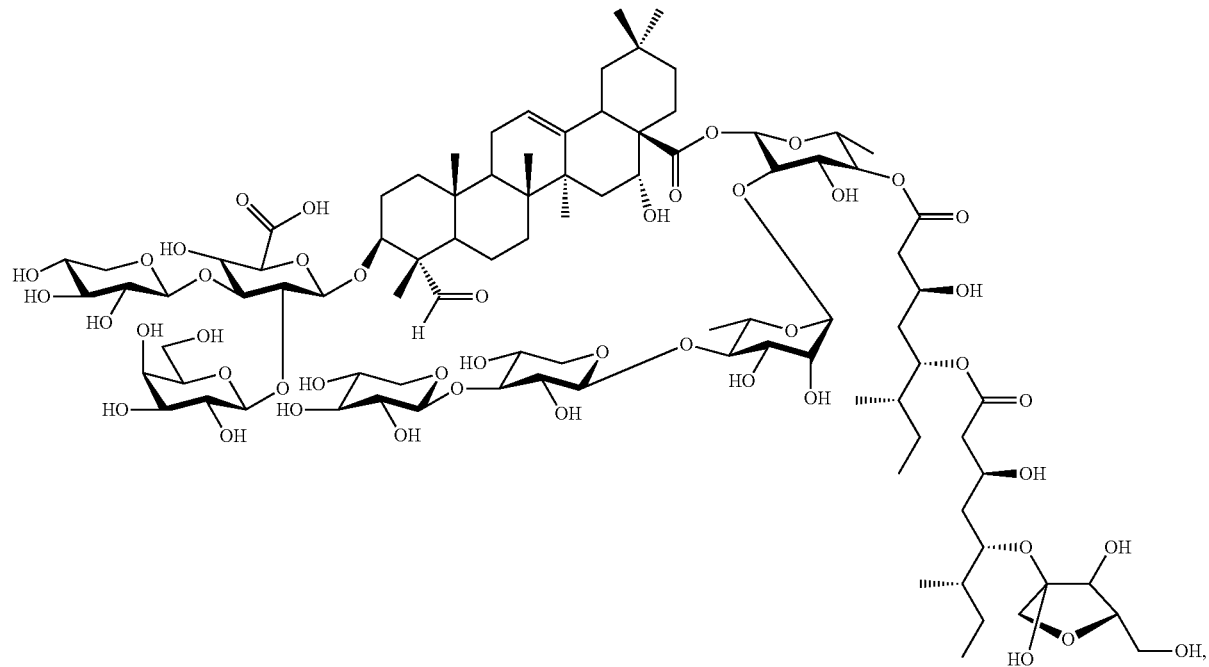
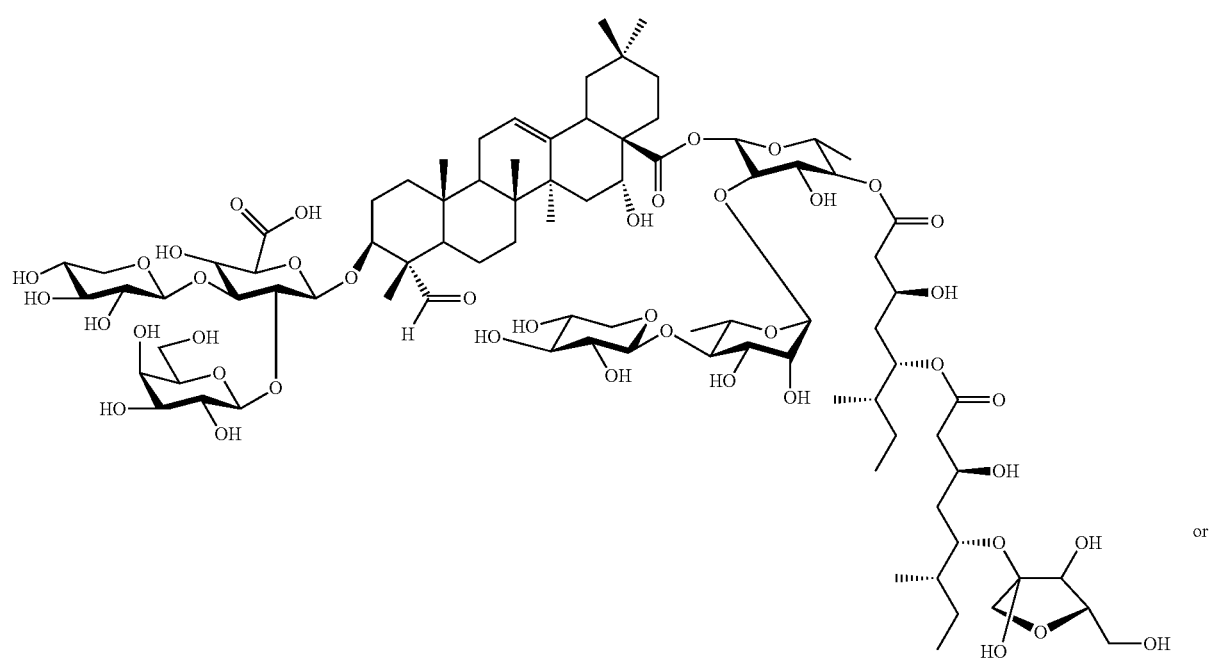

-continued

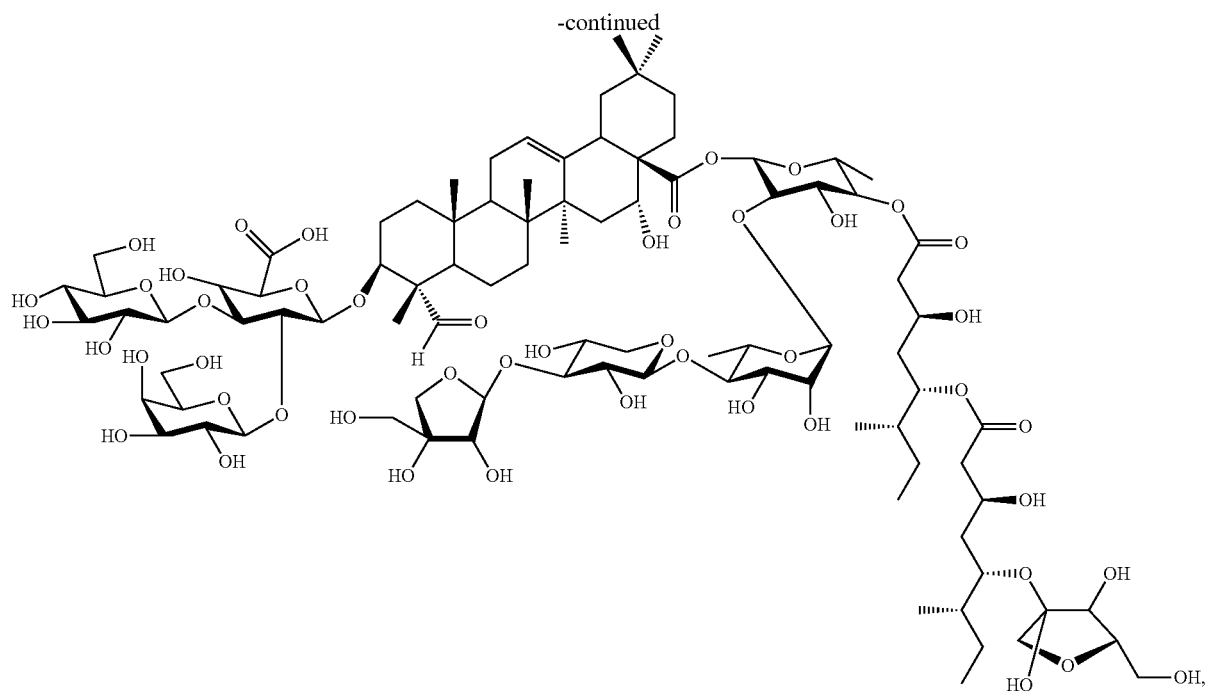

and 0.25-3%:

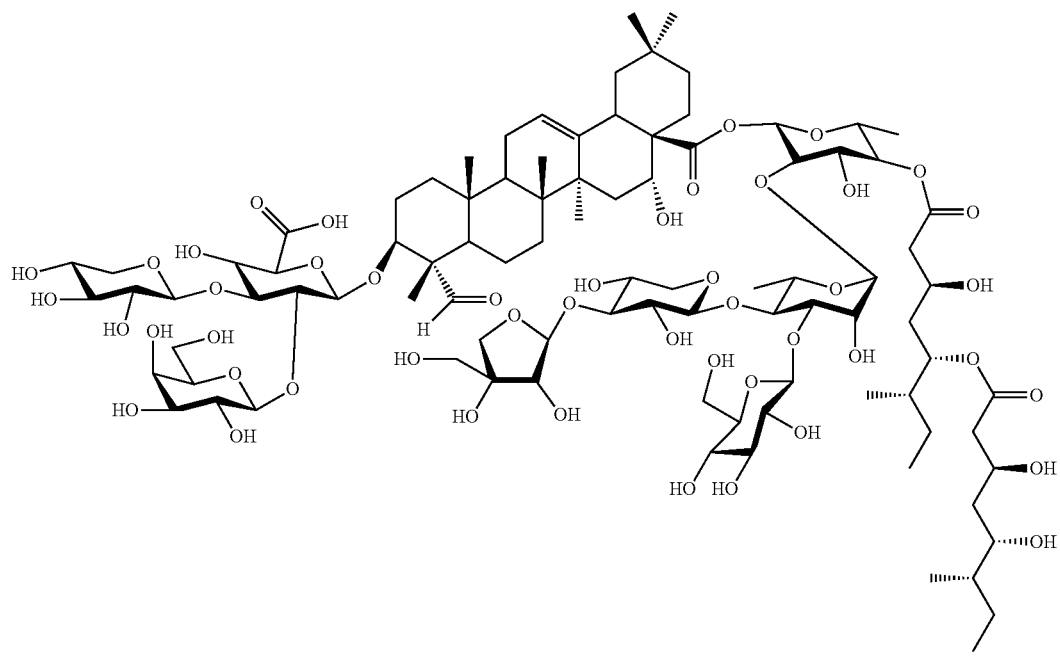

by UV absorbance at 214 nm.

Further, there is provided a method for the manufacture of a saponin extract comprising the steps of:
(i) selecting a crude aqueous extract of *Quillaja saponaria* Molina having a suitable 2018 component composition;
(ii) purifying the extract by reverse phase chromatography using a polystyrene resin; qand
(iii) purifying the extract by reverse phase chromatography using a phenyl resin.

There is provided the use of a saponin extract of the present invention in the manufacture of a medicament.

Also provided are adjuvant compositions and vaccine compositions comprising a saponin extract of the present invention.

BRIEF DESCRIPTION OF THE SEQUENCE IDENTIFIERS

Figure 1:
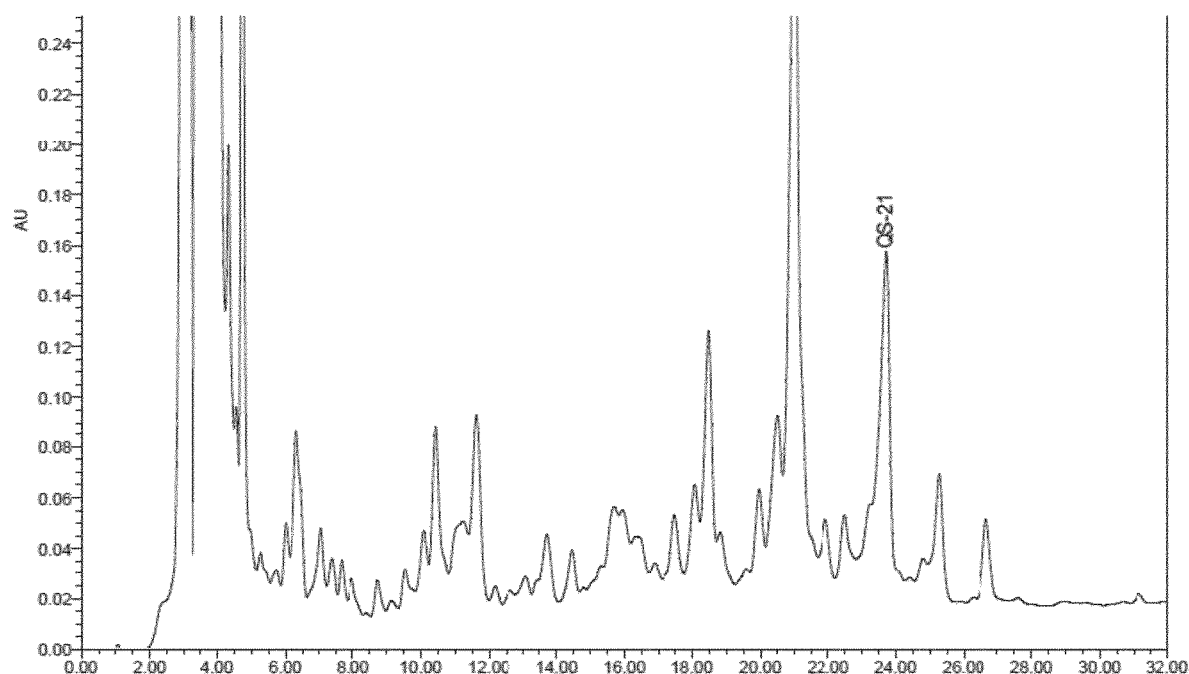
FIG. 1 HPLC chromatogram of a crude aqueous *Quillaja saponaria* Molina bark extract FIG. 2 HPLC-UV chromatogram of a crude aqueous *Quillaja saponaria* Molina bark extract FIG. 3 UPLC-UV chromatogram of a crude aqueous *Quillaja saponaria* Molina bark extract FIG. 4 UPLC-UV chromatogram of a polystyrene purified saponin extract FIG. 5 UPLC-UV/MS chromatogram of a purified *Quillaja saponaria* Molina saponin extract FIG. 6 UPLC-UV/MS chromatogram detail of a purified *Quillaja saponaria* Molina saponin extract FIG. 7 Extracted mass chromatograms for 1988 and 2002 molecular weight ions of a purified *Quillaja saponaria* Molina saponin extract FIG. 8 Combined centroid spectrum of purified *Quillaja saponaria* Molina saponin extract FIG. 9 CD4 T-cell responses at day 21 in gE AS01 vaccinated mice FIG. 10 Antibody responses at day 21 in gE AS01 vaccinated mice FIG. 11 Antibody responses at day 28 in gE AS01 vaccinated mice

SEQ ID No. 1: RTS polypeptide sequence
SEQ ID No. 2: *M. tuberculosis* H37Rv strain Rv1196 polypeptide sequence
SEQ ID No. 3: *M. tuberculosis* H37Rv strain Rv0125 polypeptide sequence
SEQ ID No. 4: M72 fusion polypeptide sequence
SEQ ID No. 5: M72-2his fusion polypeptide sequence
SEQ ID No. 6: *Varicella zoster* virus truncated gE polypeptide sequence
SEQ ID No. 7: Conformationally constrained RSV PreF antigen polypeptide sequence
SEQ ID No. 8: HIV TV1 gp120 polypeptide sequence

DETAILED DESCRIPTION OF THE INVENTION

As mentioned previously, any component of a product which is authorised as a human medicament requires the use of approved manufacturing processes and careful control of final composition to ensure that it meets the required specification. Deviations from specification result in waste. However, safety and efficacy investigation relies upon the testing of defined compositions, therefore adaptation of component specifications introduces risk. Modification of existing processes requires costly and time consuming re-validation.

The present inventors have found that crude aqueous extract of *Quillaja saponaria* Molina varies in composition, in particular with respect to a component referred to herein as the 2018 component, and that it is difficult to separate excess 2018 component by applying existing approved manufacturing processes. Consequently, the present invention provides methods for achieving a consistent purified extract by the use of a crude aqueous extract of a defined composition.

The present invention provides a saponin extract containing at least 93% QS-21 main peak and 0.25-3% 2018 component by UV absorbance at 214 nm, in particular, wherein the monoisotope of the most abundant species is 1987.9 m/z. Suitably the saponin extract contains at least 98% QS-21 group by UV absorbance at 214 nm. Typically the saponin extract contains 1% or less of lyo impurity, especially 1% or less of the largest peak outside the QS-21 group by UV absorbance at 214 nm.

Of particular interest are saponin extracts containing at least 98% QS-21 group, at least 93% QS-21 main peak, 0.25-3% 2018 component, 1% or less of largest peak outside the QS-21 group by UV absorbance at 214 nm and wherein the monoisotope of the most abundant species is 1987.9 m/z.

Also provided is a saponin extract containing at least 93% triterpenoid glycosides having m/z of 1855.9, 1987.9 or 2001.9, and 0.25-3% triterpenoid glycosides having m/z 2017.9 by UV absorbance at 214 nm, in particular, wherein the monoisotope of the most abundant species is 1987.9 m/z. Desirably the saponin extract contains at least 93% triterpenoid glycosides having m/z of 1855.9, 1987.9 or 2001.9, excluding B-isomer and lyo impurity, and 0.25-3% triterpenoid glycosides having m/z 2017.9 by UV absorbance at 214 nm, in particular, wherein the monoisotope of the most abundant species is 1987.9 m/z. Suitably the saponin extract contains at least 98% triterpenoid glycosides having m/z of 1517.7, 1711.8, 1855.9, 1987.9, 2001.9, 2017.9 or 2118 by UV absorbance at 214 nm. Desirably the saponin extract contains at least 98% triterpenoid glycosides having m/z of 1517.7, 1711.8, 1855.9, 1987.9, 2001.9, 2017.9 or 2118, excluding the lyo impurity, by UV absorbance at 214 nm. Typically the saponin extract contains 1% or less of lyo impurity by UV absorbance at 214 nm. Suitably the saponin extract contains 1% or less of any other peak by UV absorbance at 214 nm.

Of particular interest are saponin extracts containing at least 98% triterpenoid glycosides having m/z of 1517.7, 1711.8, 1855.9, 1987.9, 2001.9, 2017.9 or 2118, at least 93% triterpenoid glycosides having m/z of 1855.9, 1987.9 or 2001.9, 0.25-3% triterpenoid glycosides having m/z 2017.9, 1% or less of any other peak by UV absorbance at 214 nm and wherein the monoisotope of the most abundant species is 1987.9 m/z, especially wherein the saponin extract contains at least 98% triterpenoid glycosides having m/z of 1517.7, 1711.8, 1855.9, 1987.9, 2001.9, 2017.9 or 2118, excluding the lyo impurity, and at least 93% triterpenoid glycosides having m/z of 1855.9, 1987.9 or 2001.9 excluding B-isomer and lyo impurity, 0.25-3% triterpenoid glycosides having m/z 2017.9, 1% or less of any other peak by UV absorbance at 214 nm and wherein the monoisotope of the most abundant species is 1987.9 m/z.

Additionally provided is a saponin extract containing at least 93%:
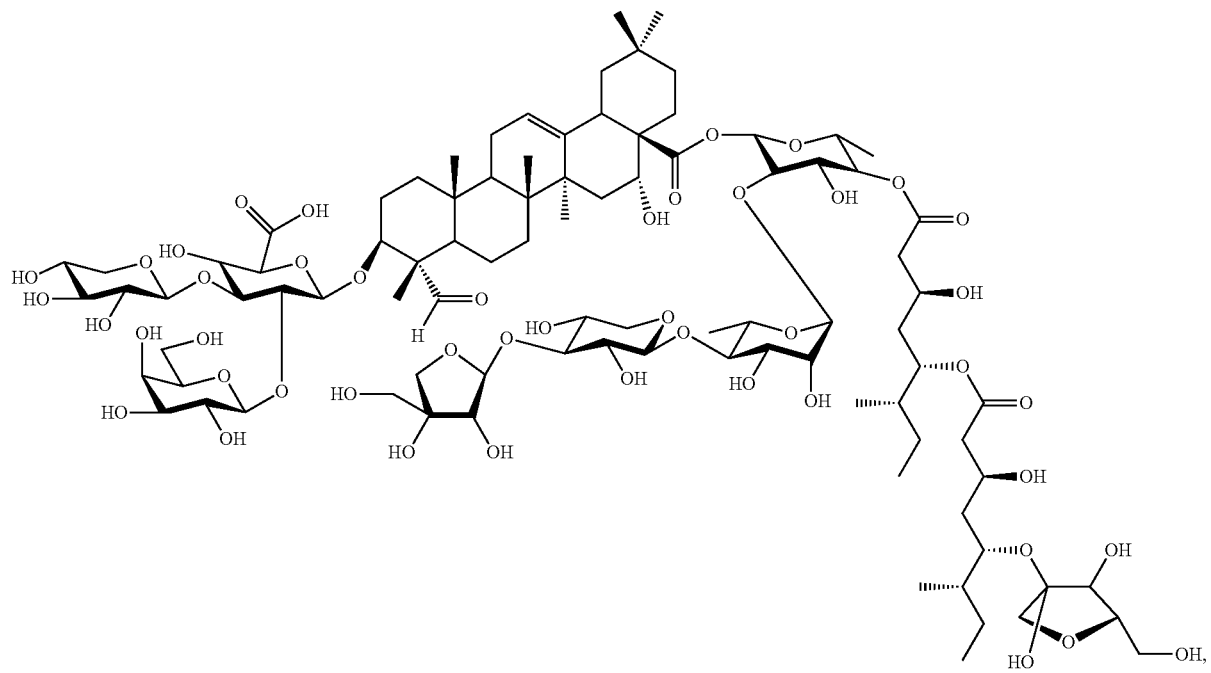
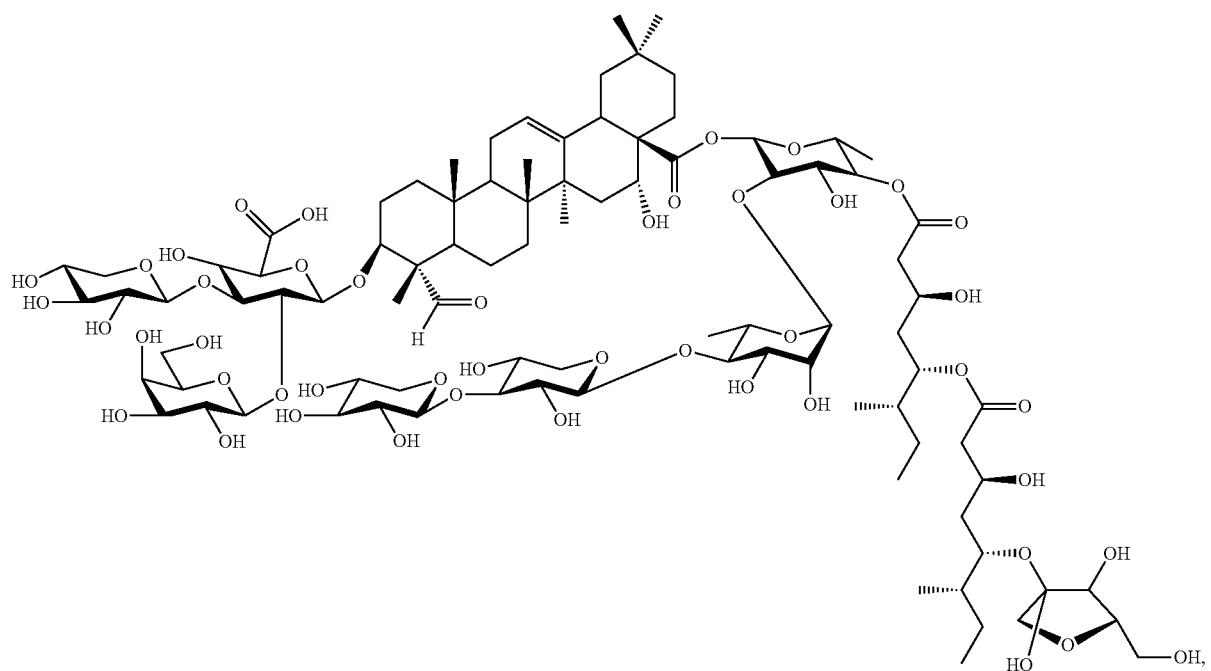

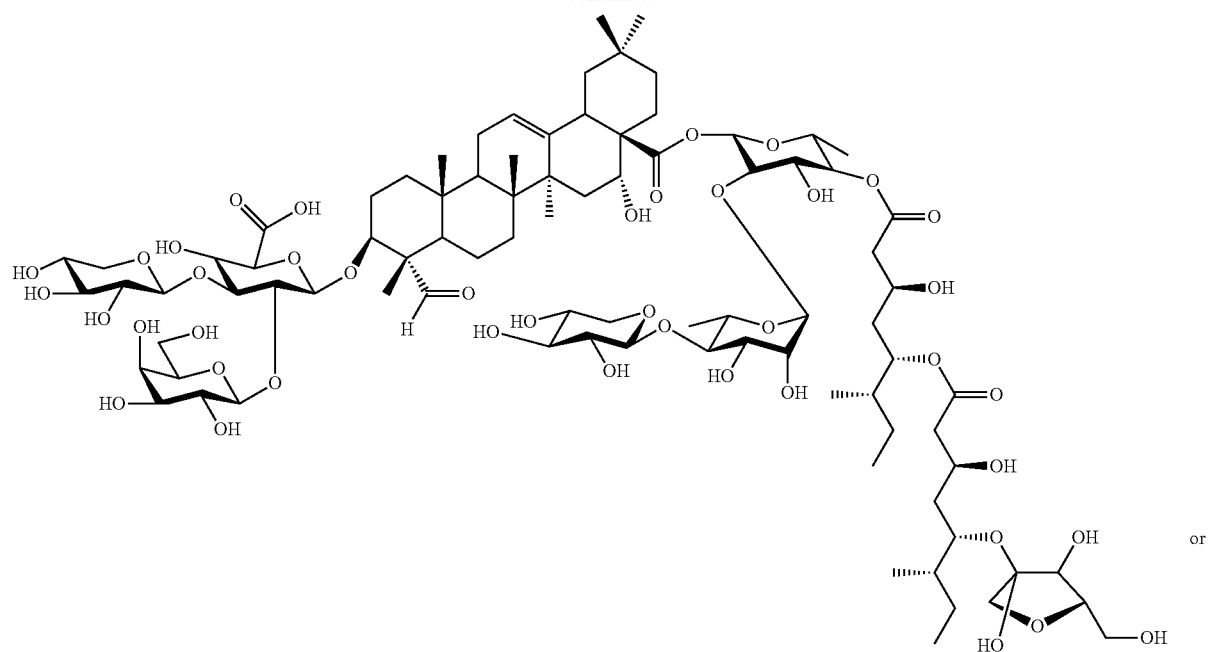
or
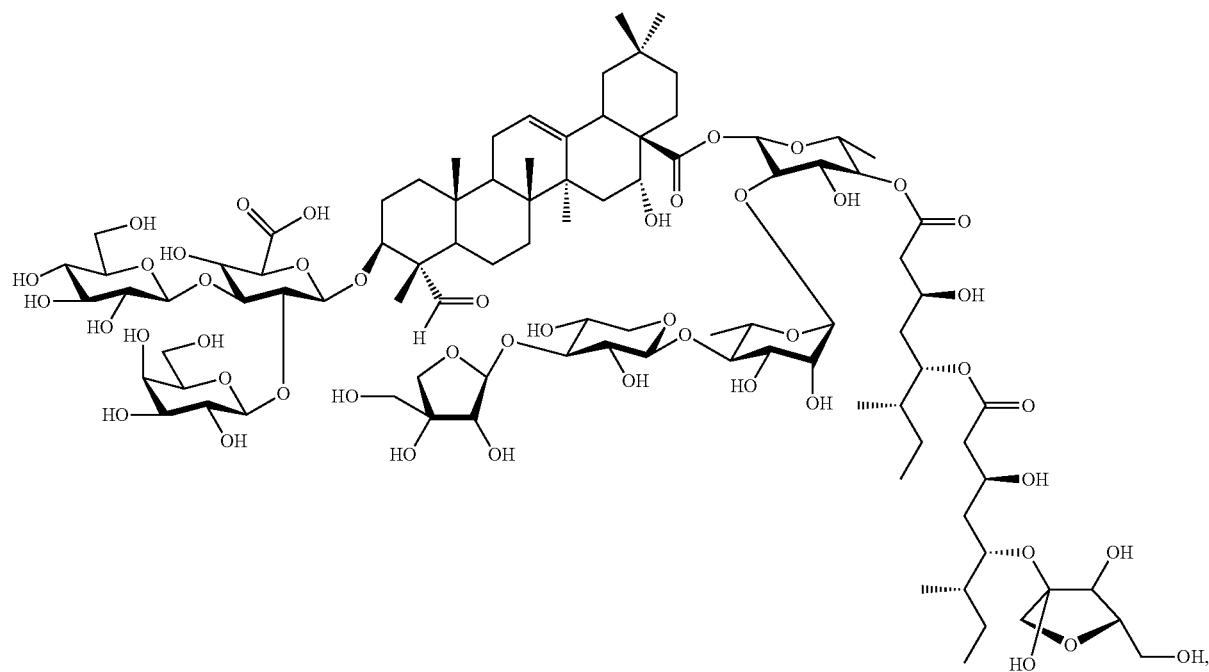

and 0.25-3%:
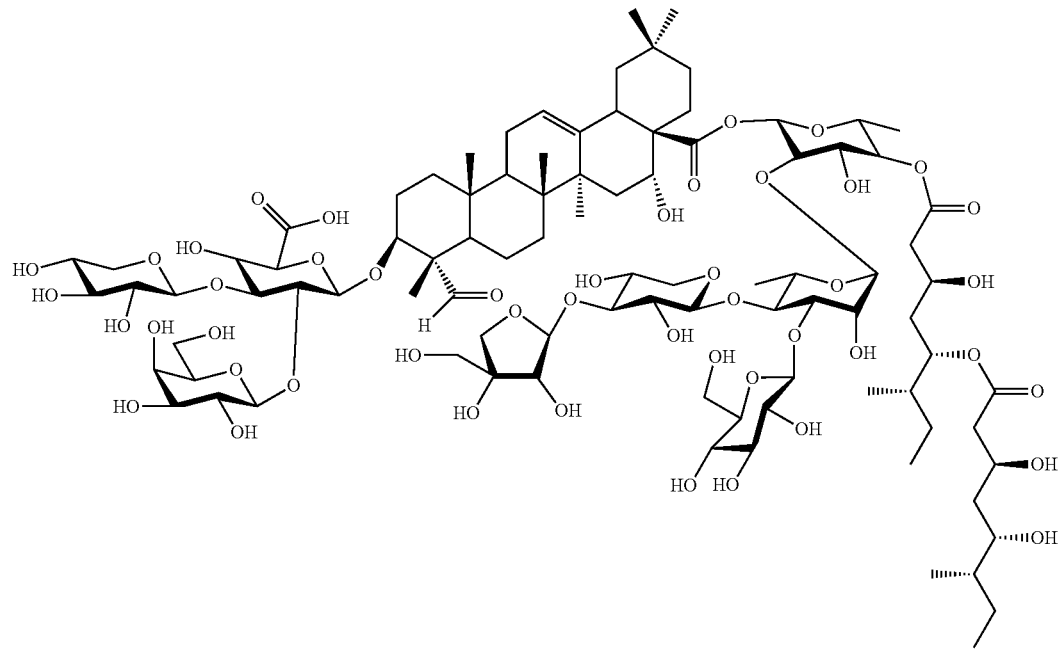
by UV absorbance at 214 nm, in particular, wherein the monoisotope of the most abundant species is 1987.9 m/z. Suitably the saponin extract contains at least 98%:
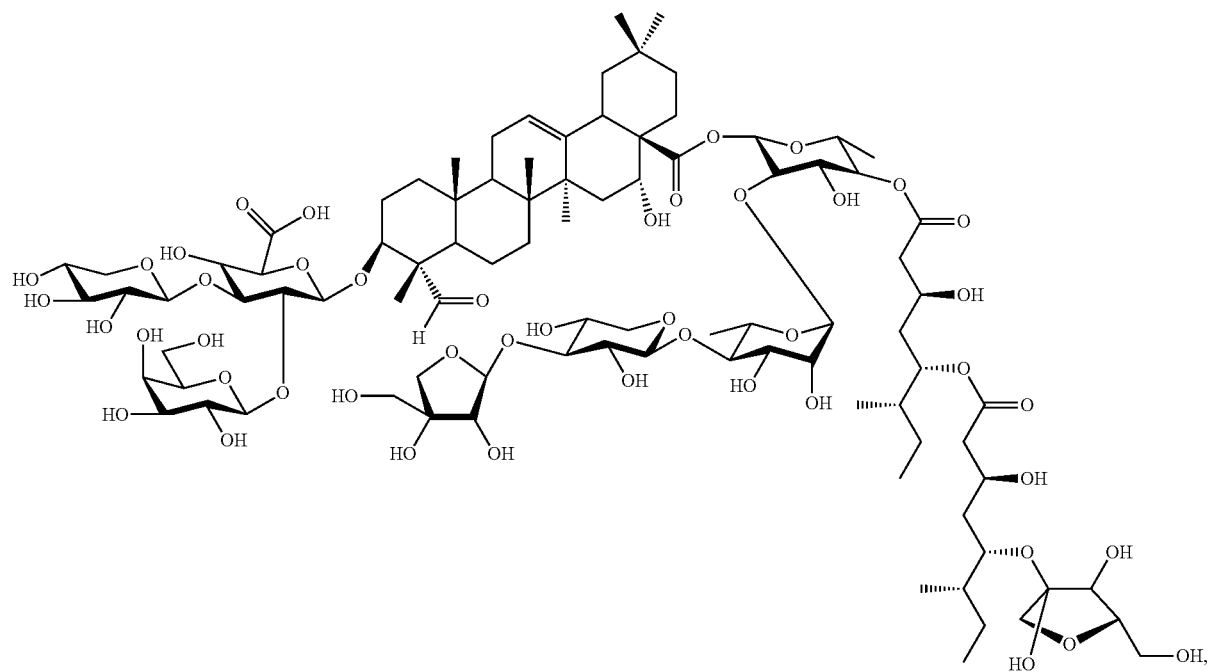

-continued
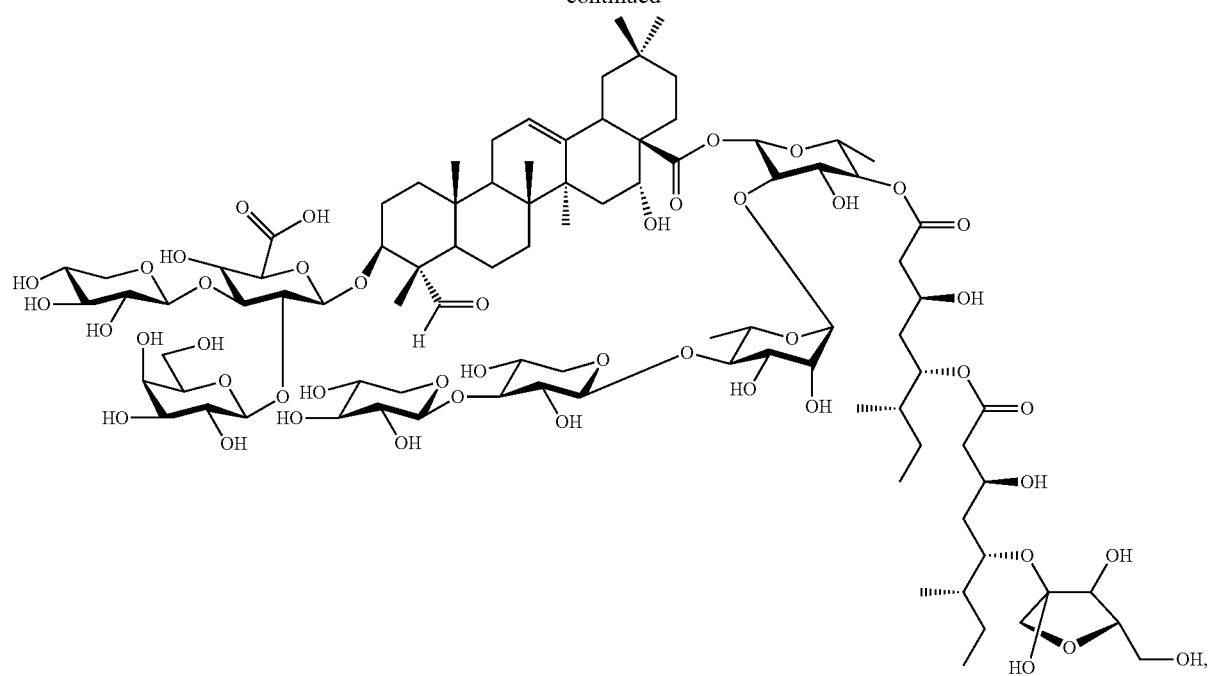
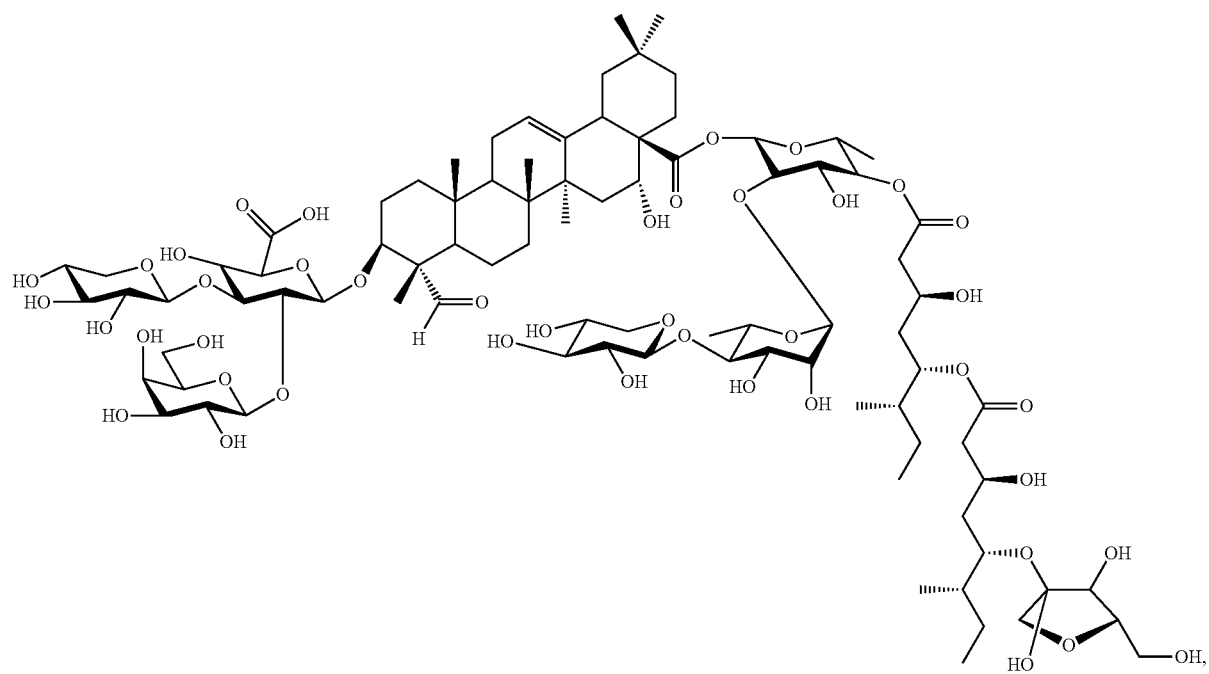

-continued
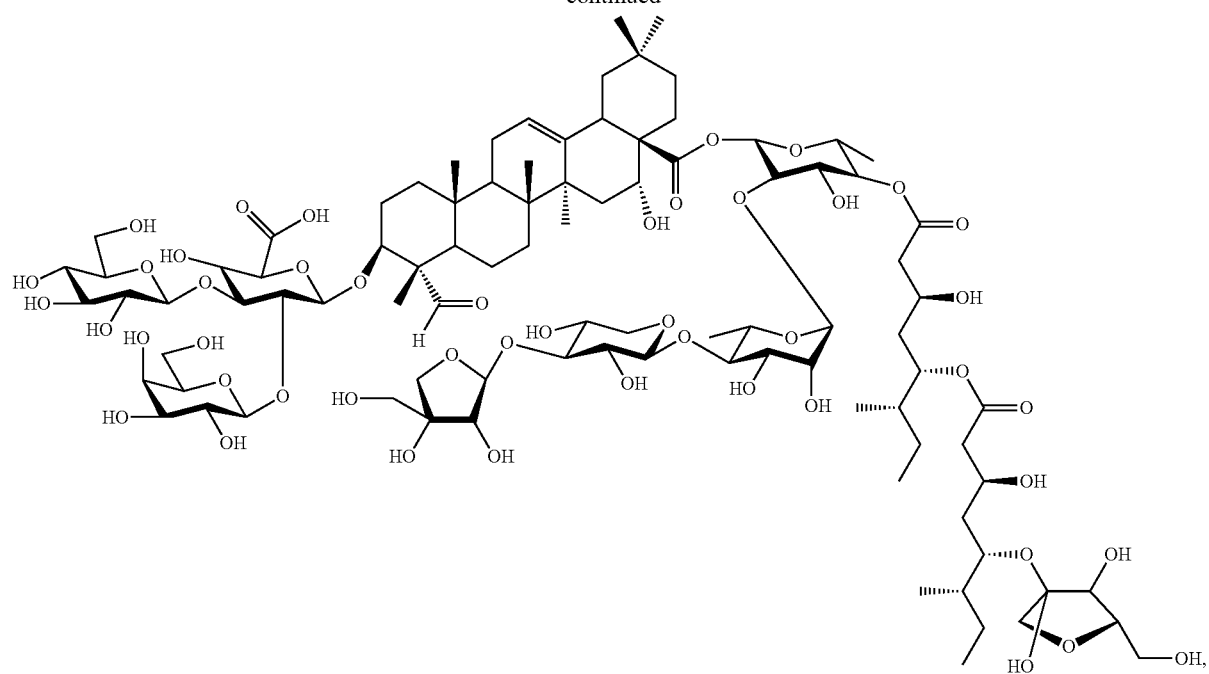
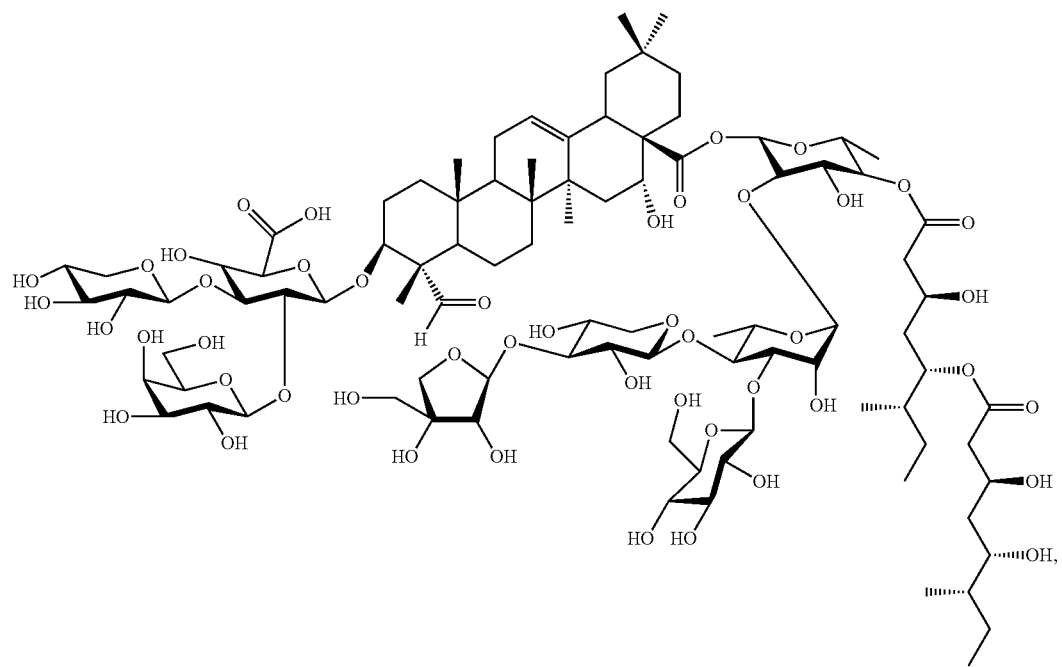

-continued
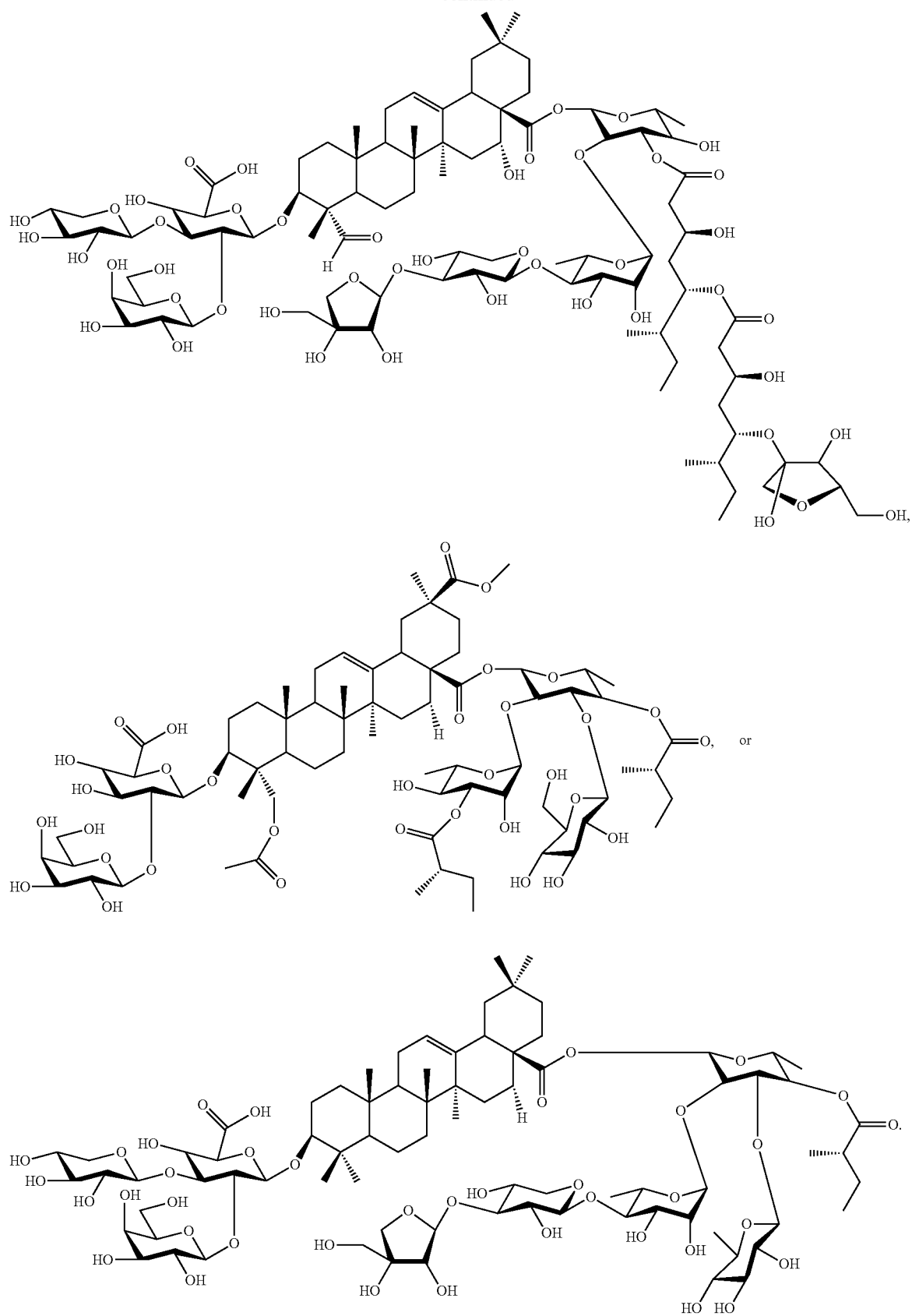

Suitably the saponin extract contains 98% of the aforementioned components and the 2118 component. Typically the saponin extract contains 1% or less:
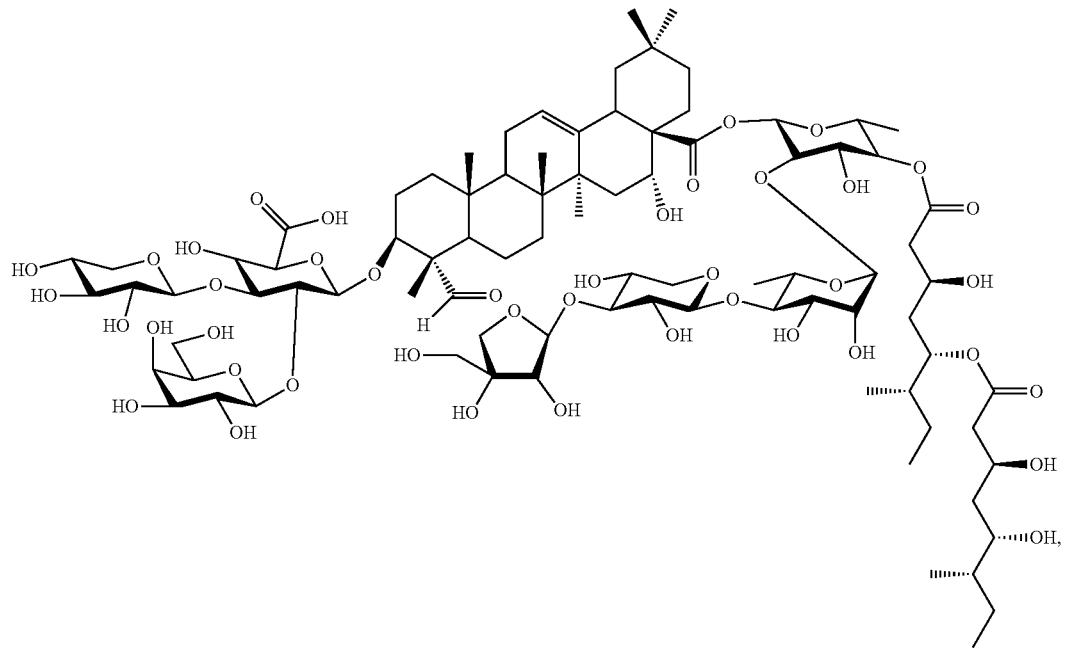
especially 1% or less of any other peak by UV absorbance at 214 nm.
Of particular interest are saponin extracts containing at least 98%:
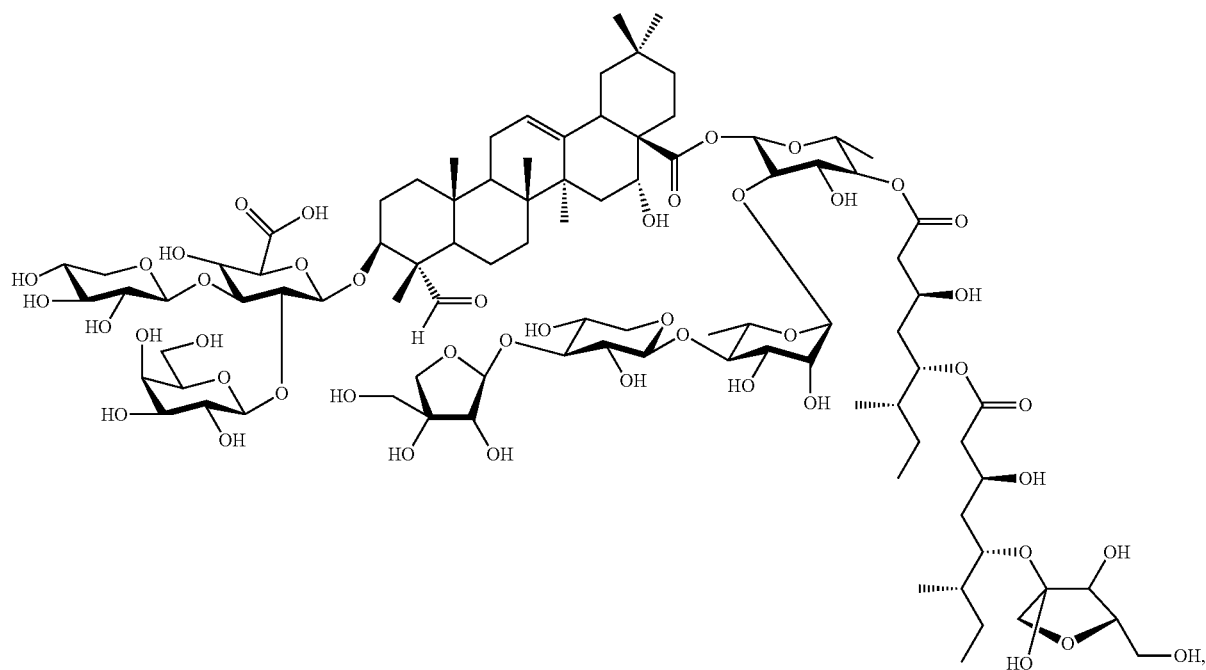

-continued
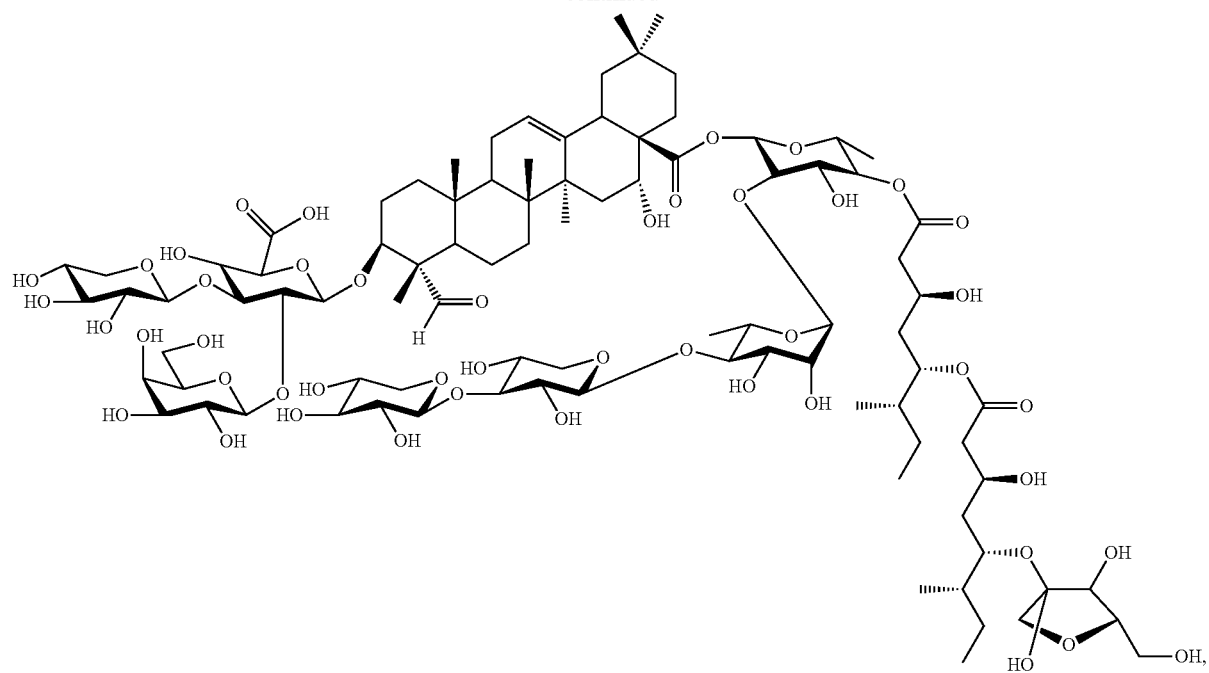
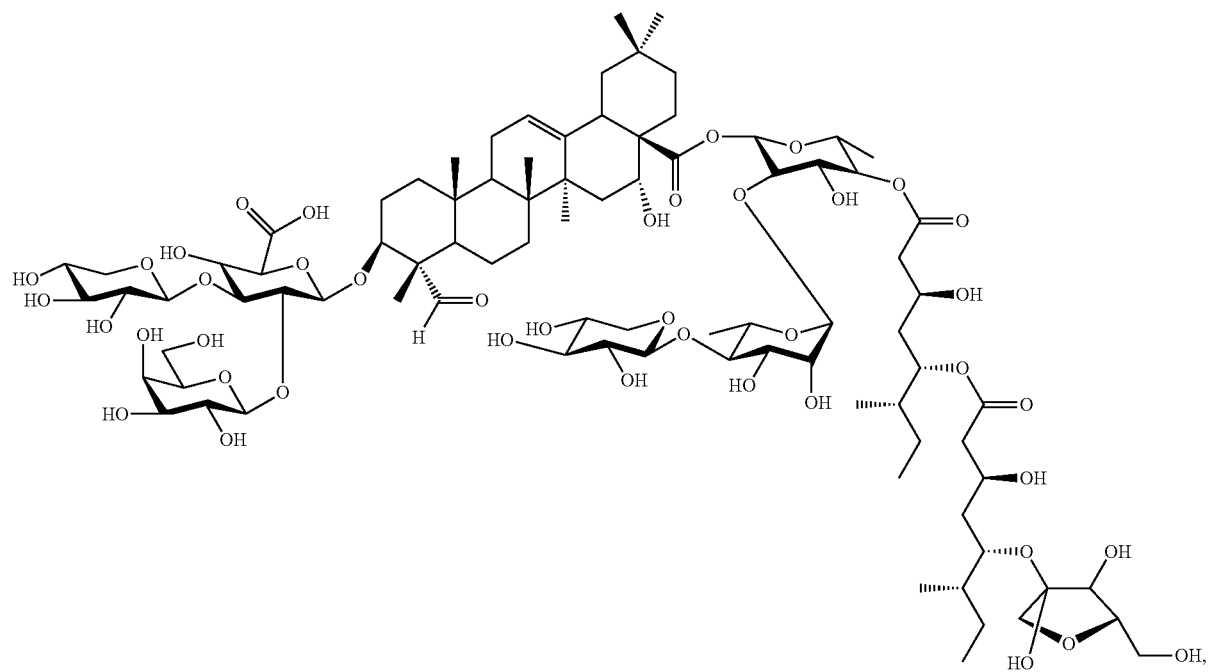

-continued
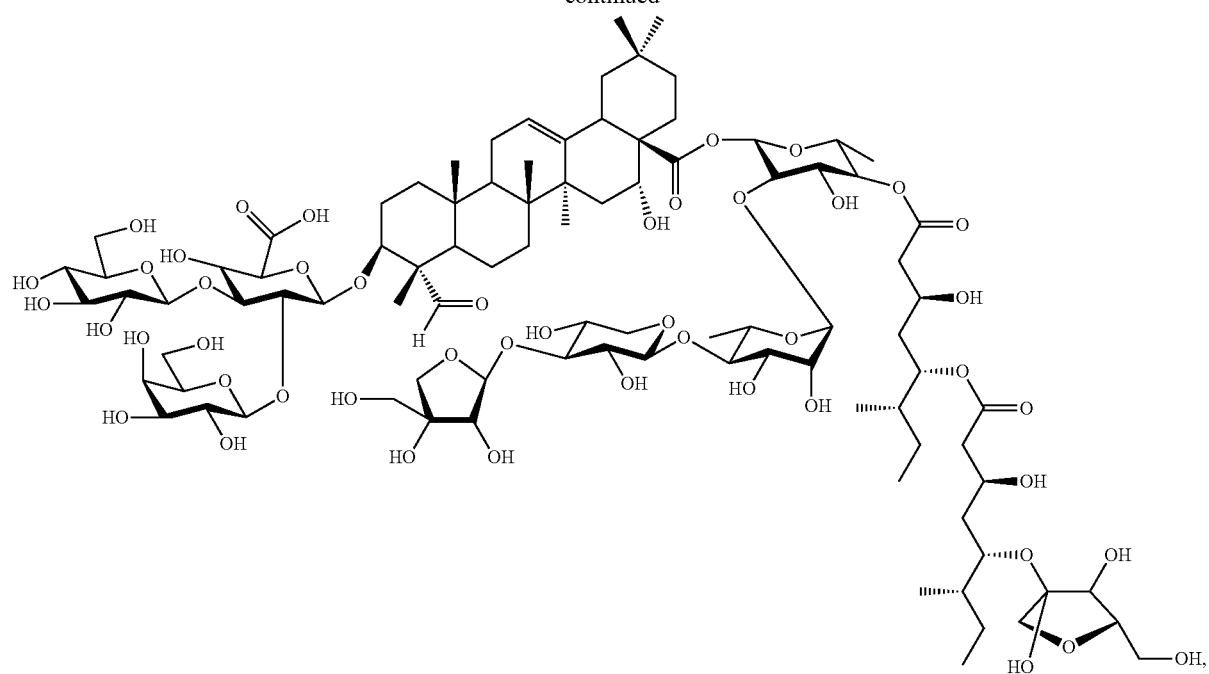
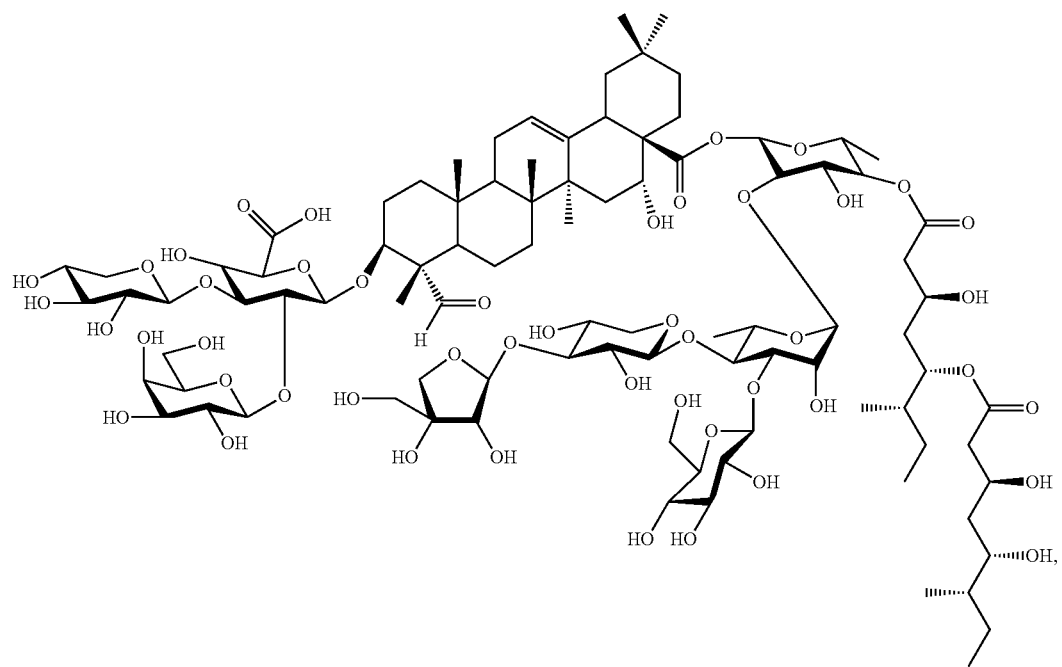

-continued
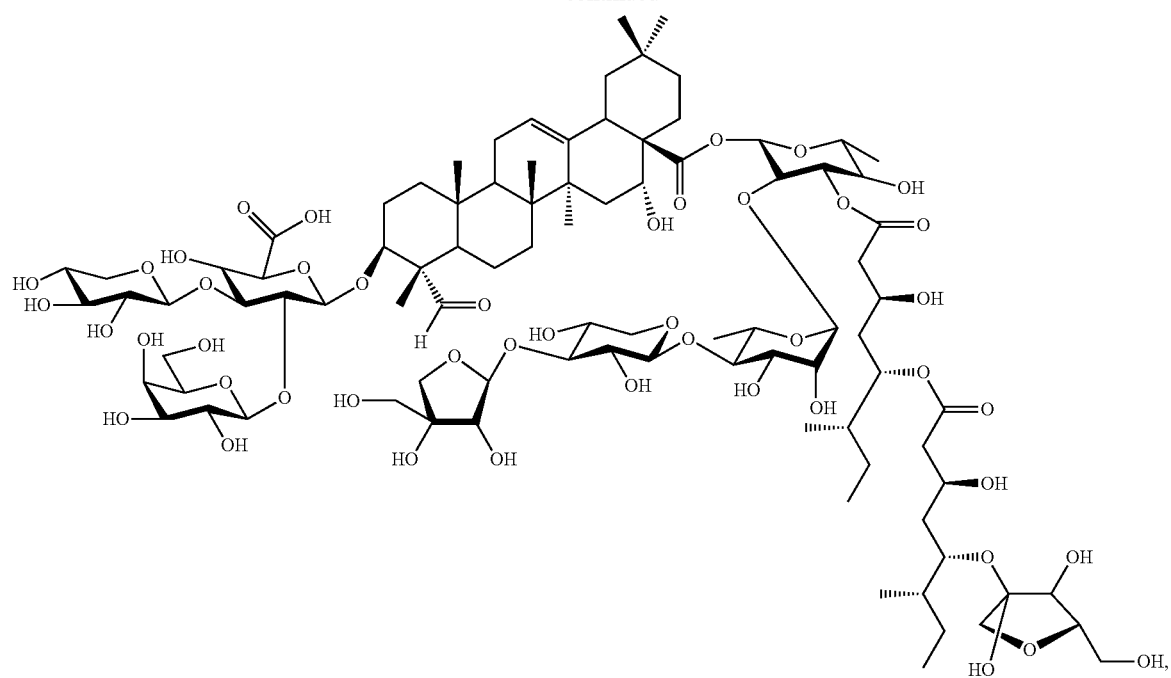
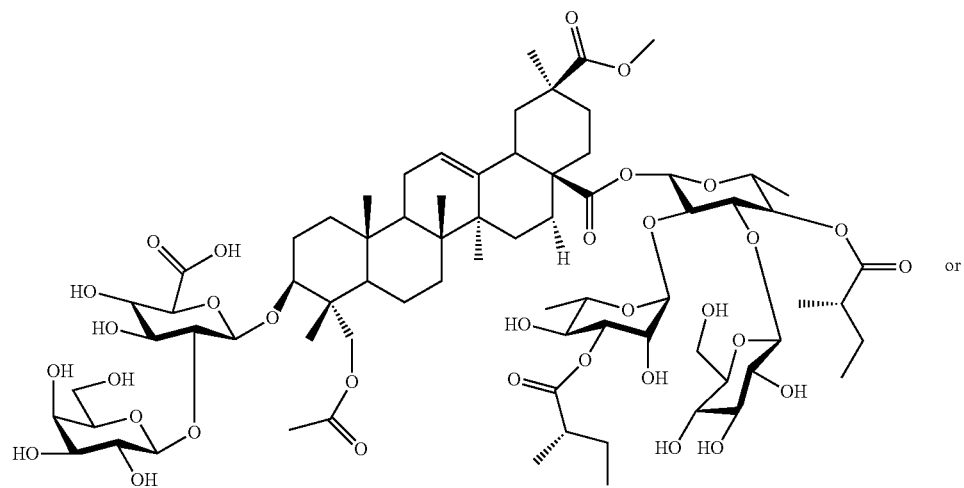
or
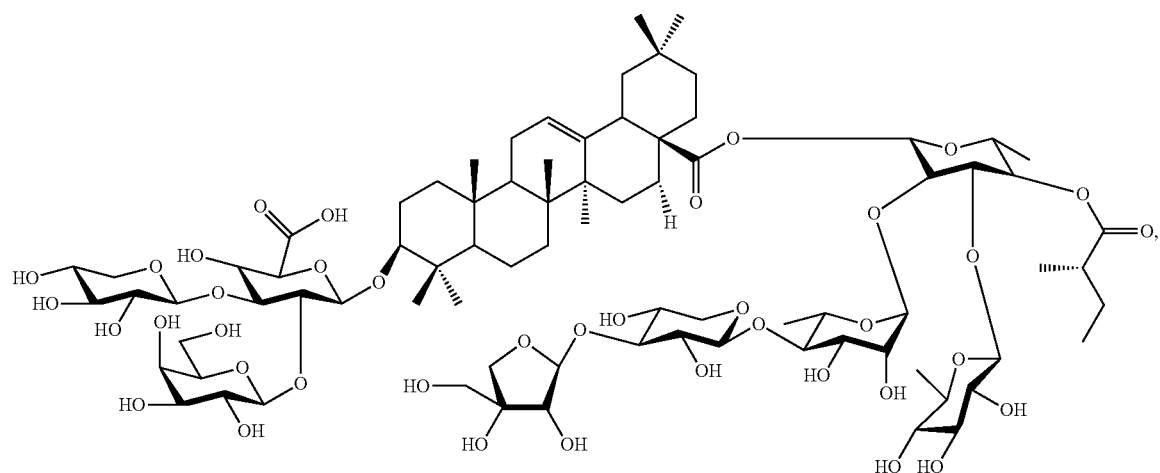

at least 93%:
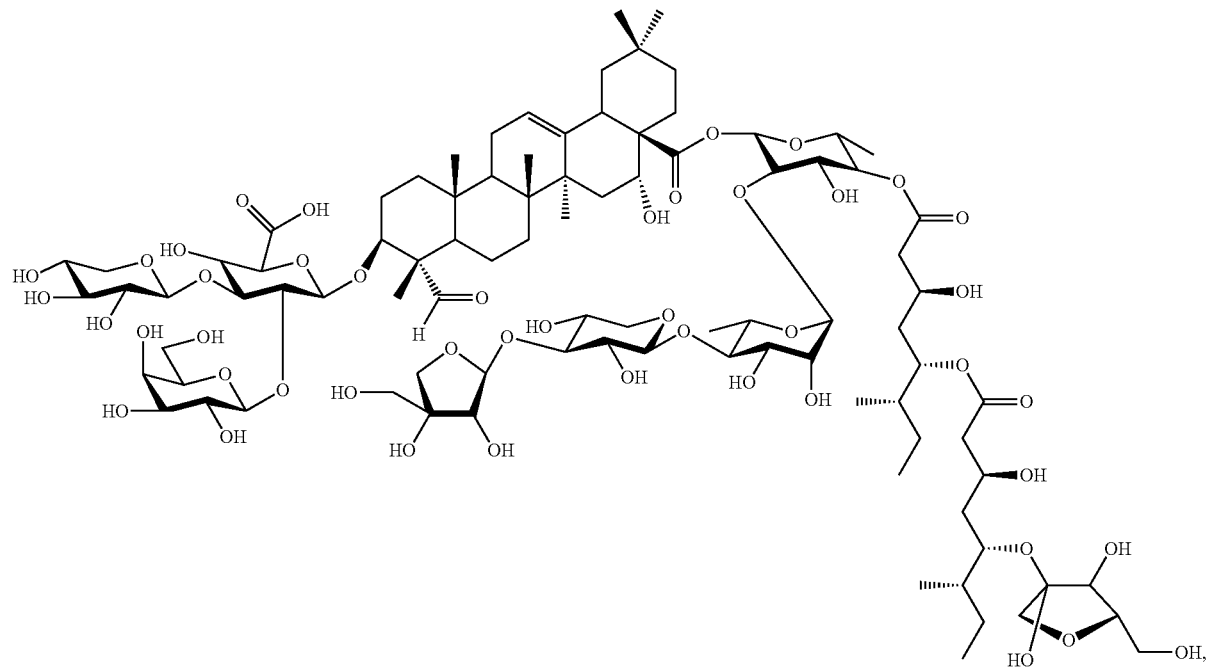
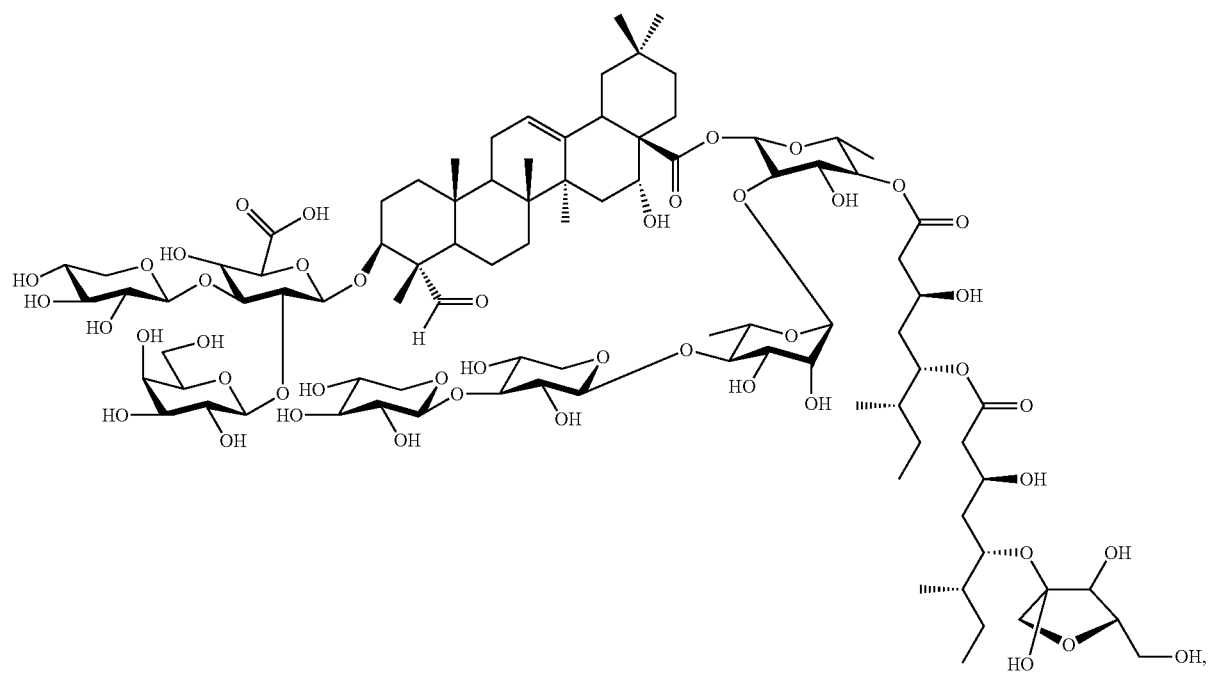

-continued
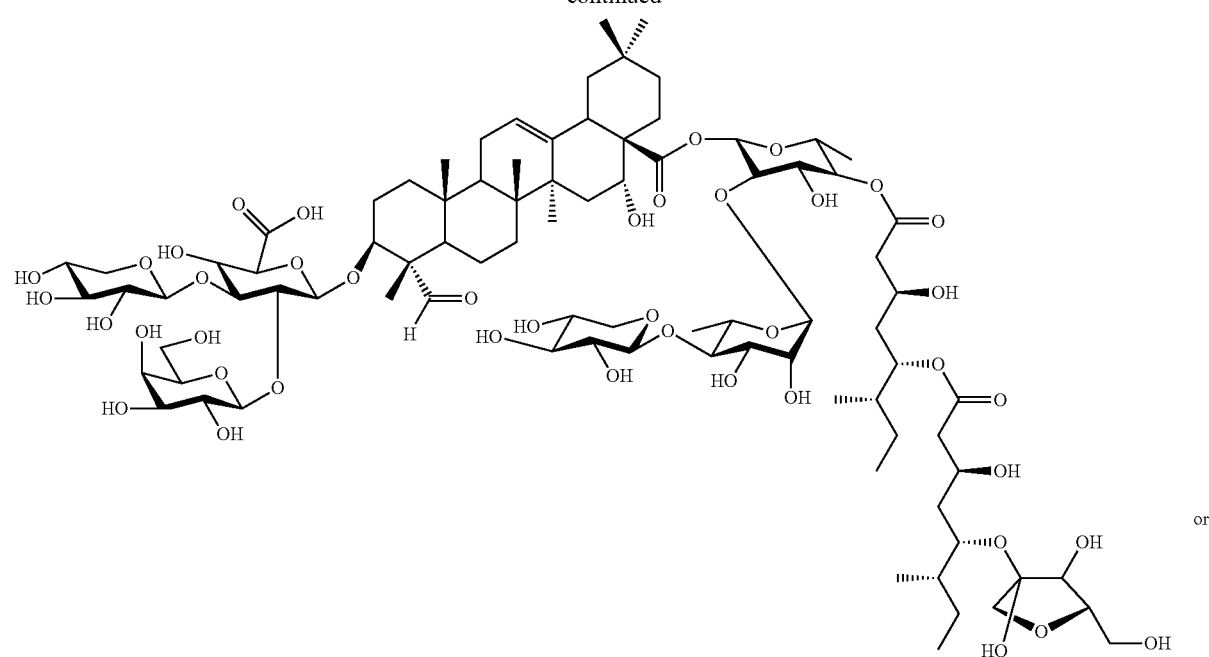
or
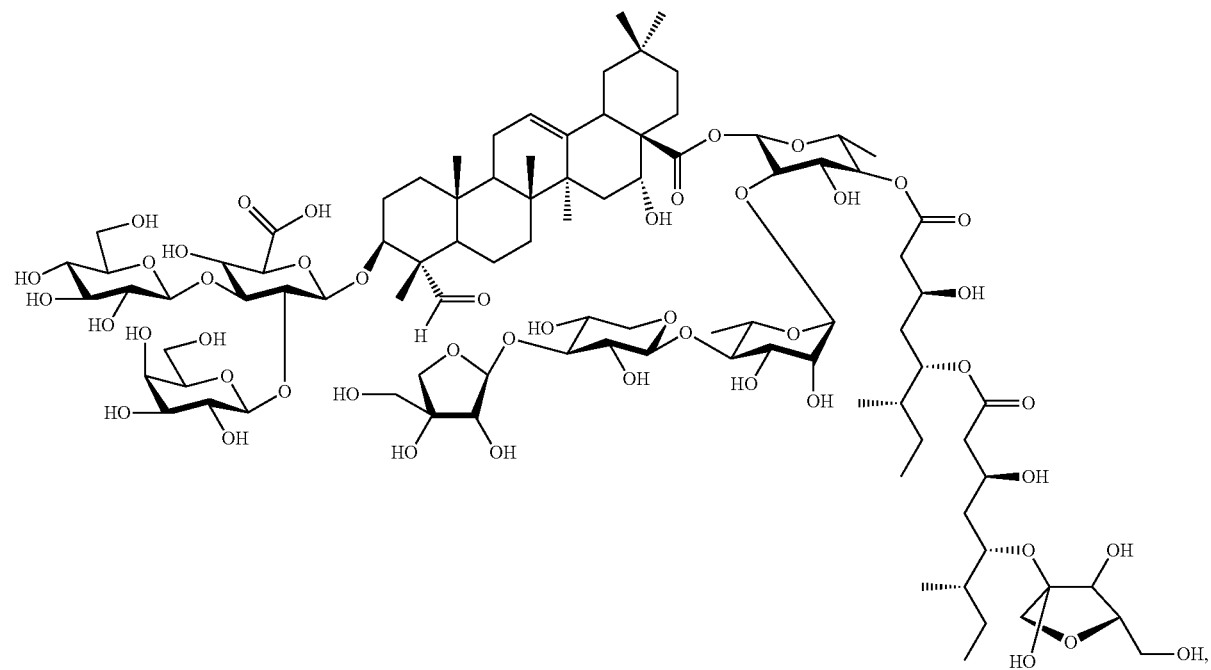

0.25-3%:
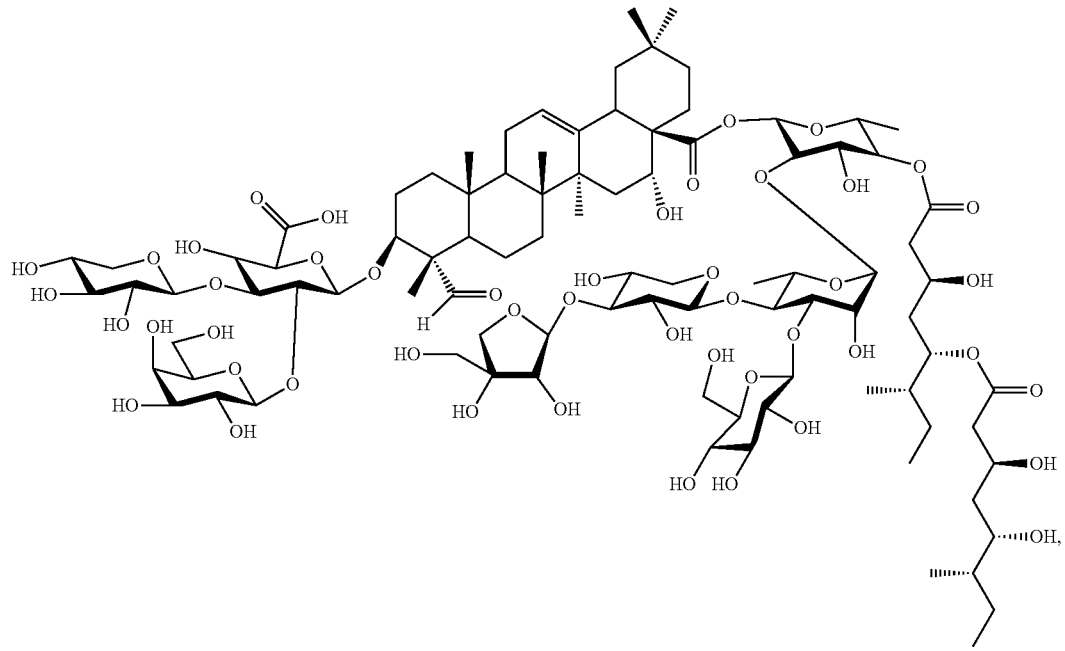
1% or less of any other peak by UV absorbance at 214 nm and wherein the monoisotope of the most abundant species is 1987.9 m/z. Especially of interest are saponin extracts containing at least 98%:
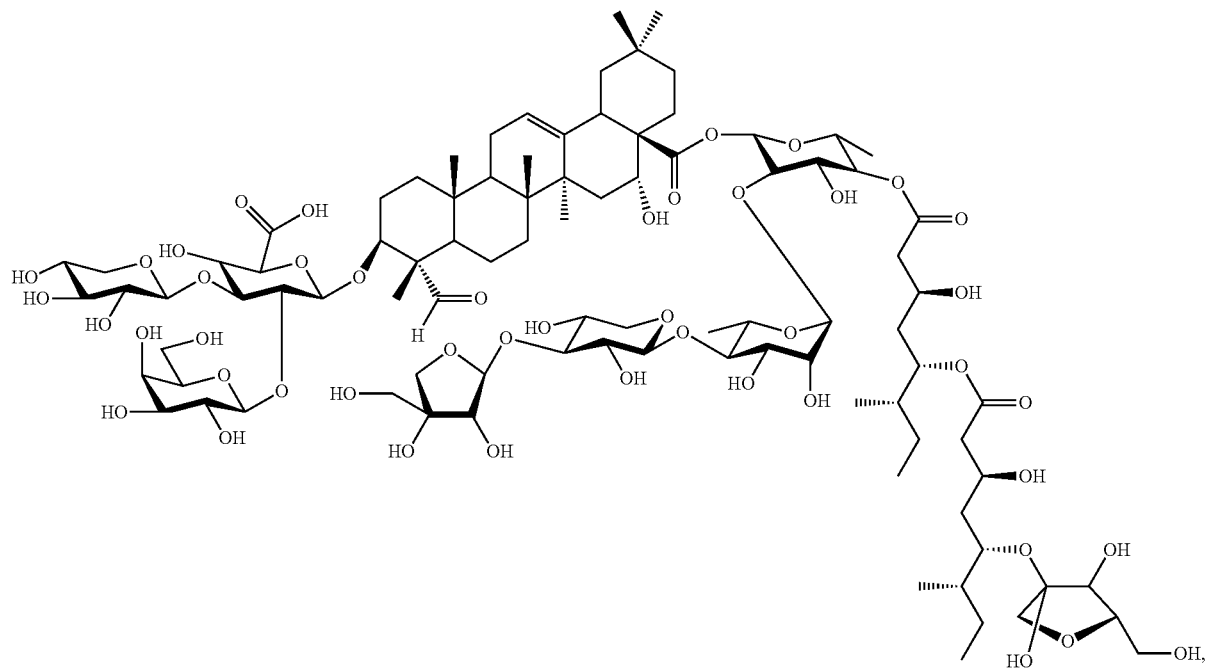

-continued
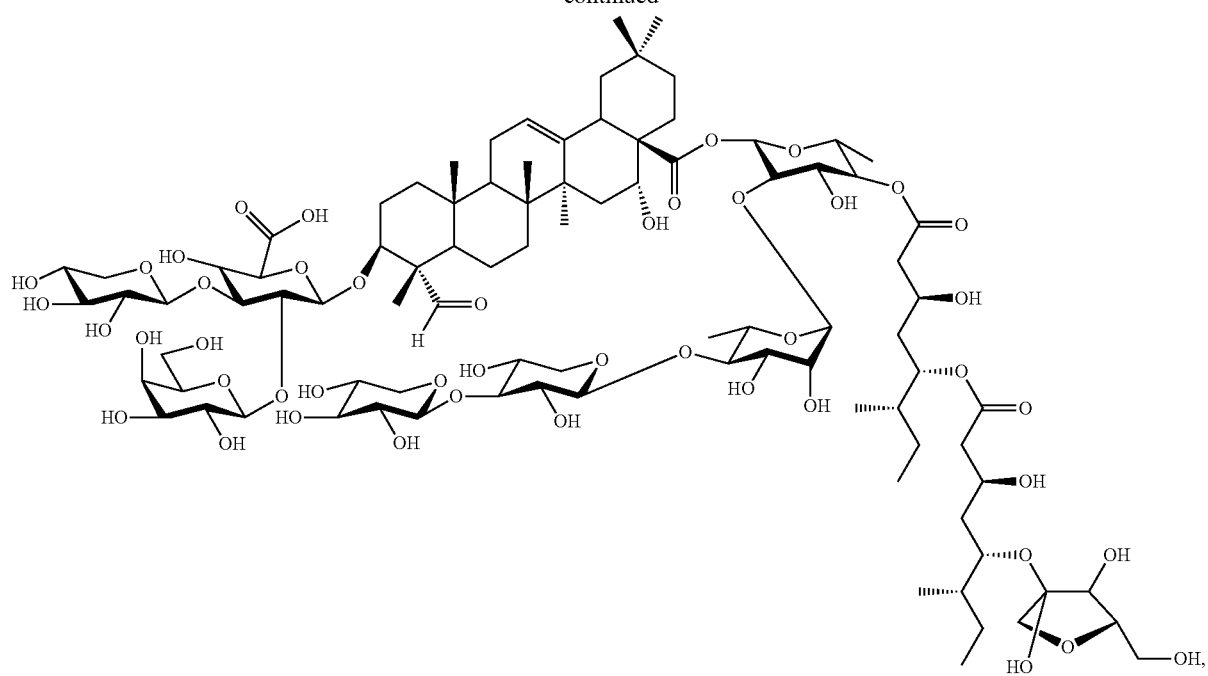
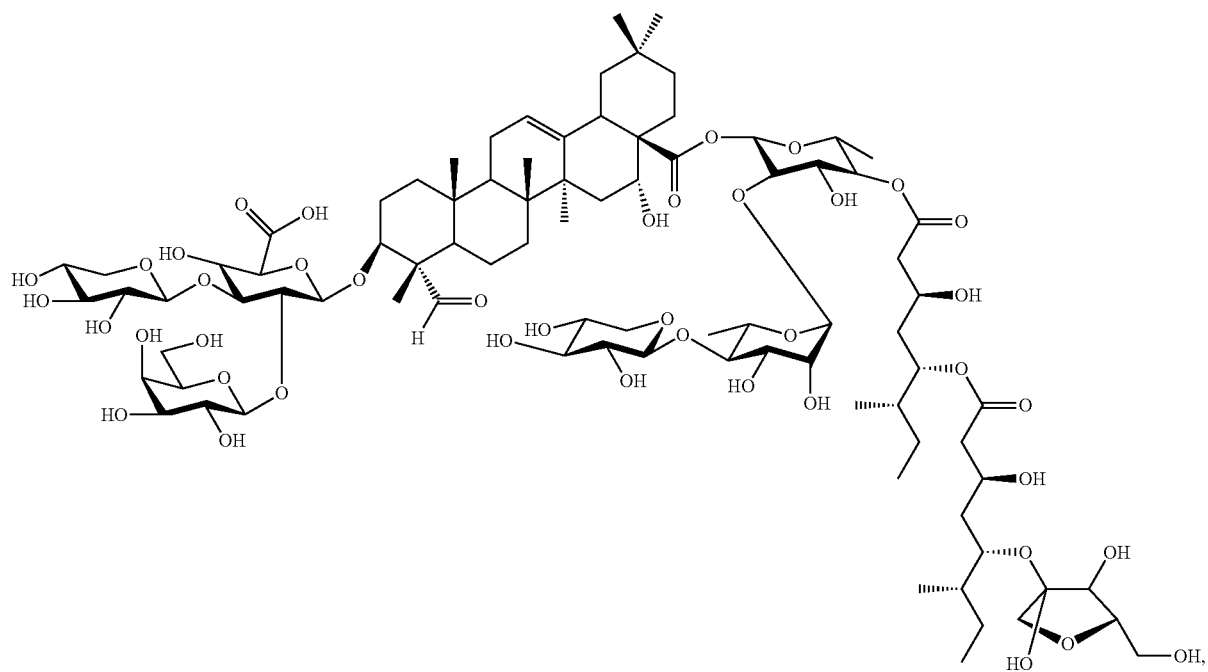

-continued
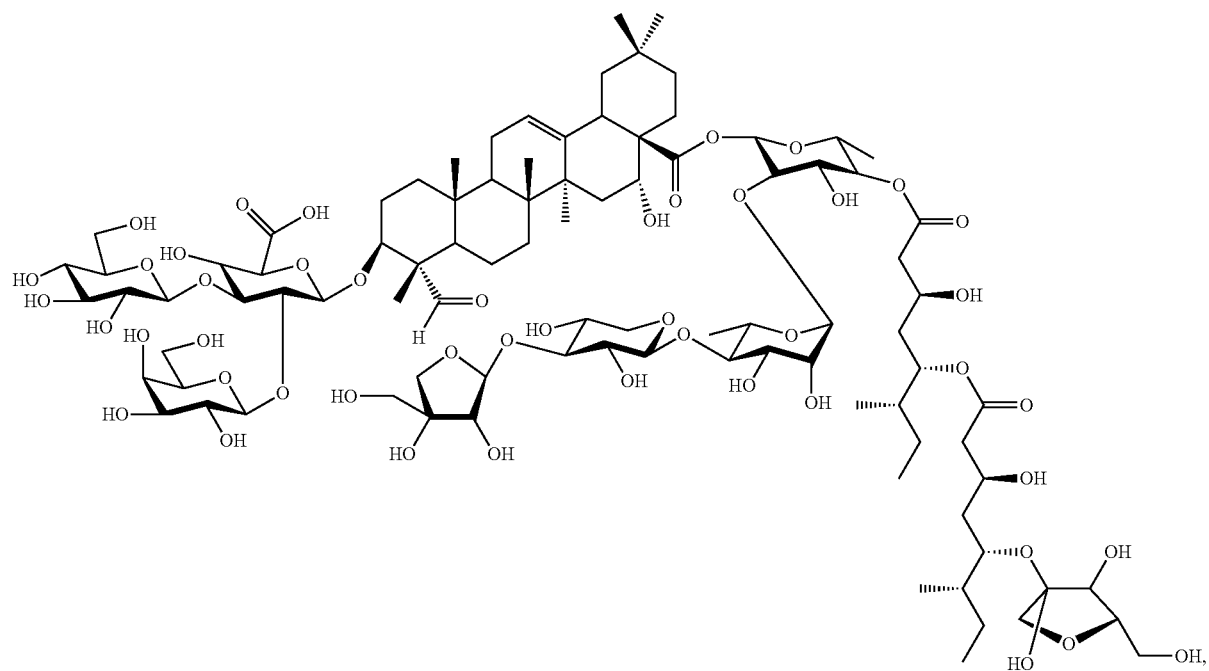
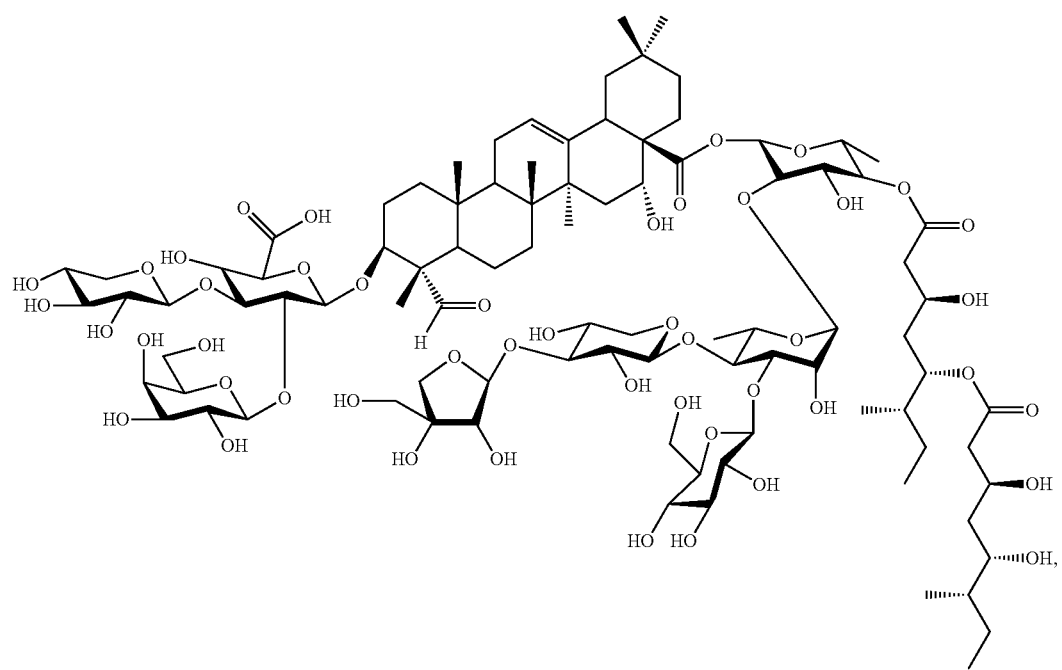

-continued
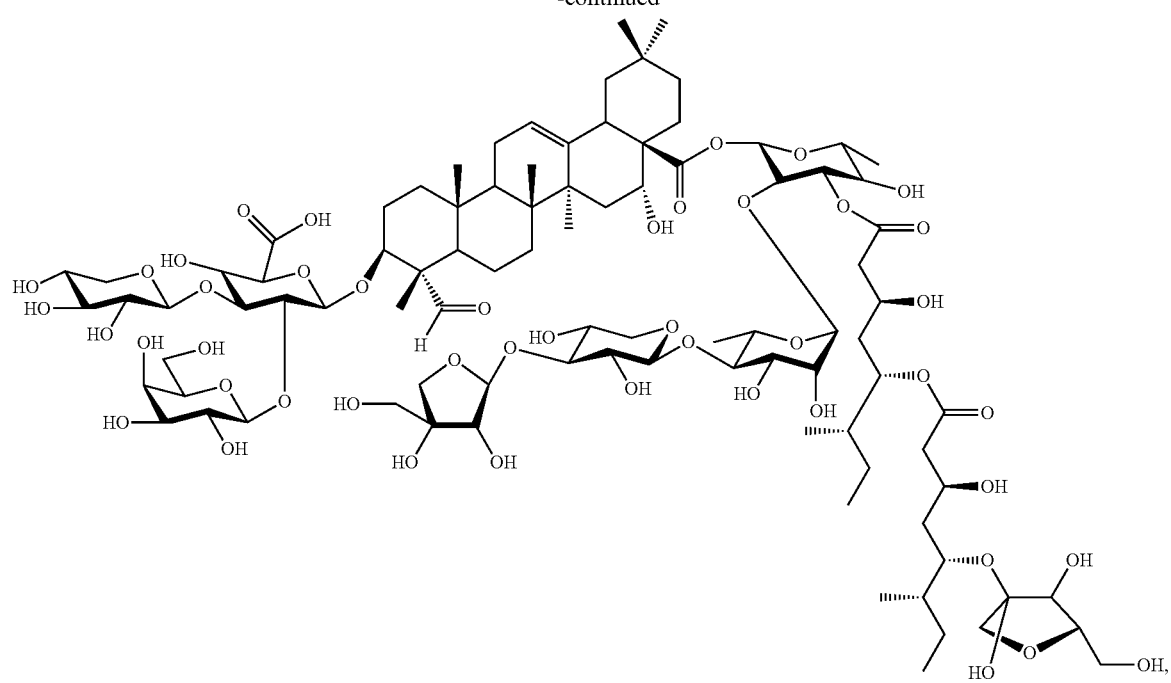
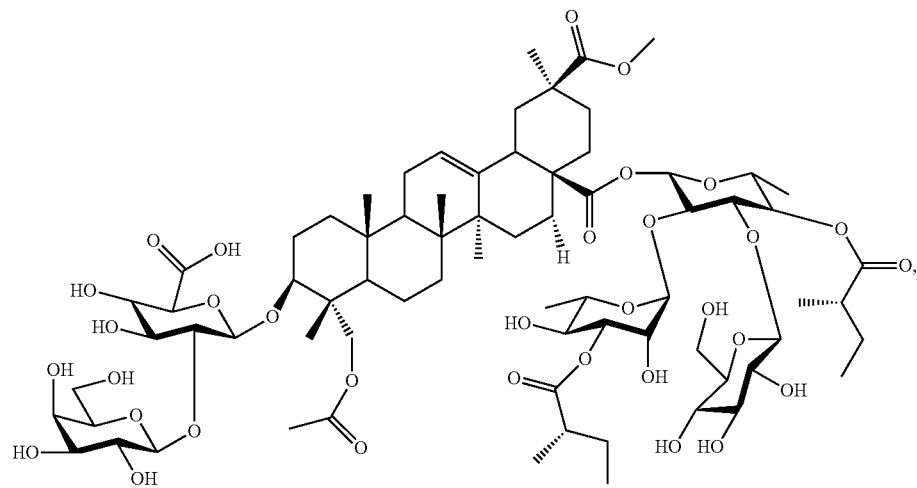
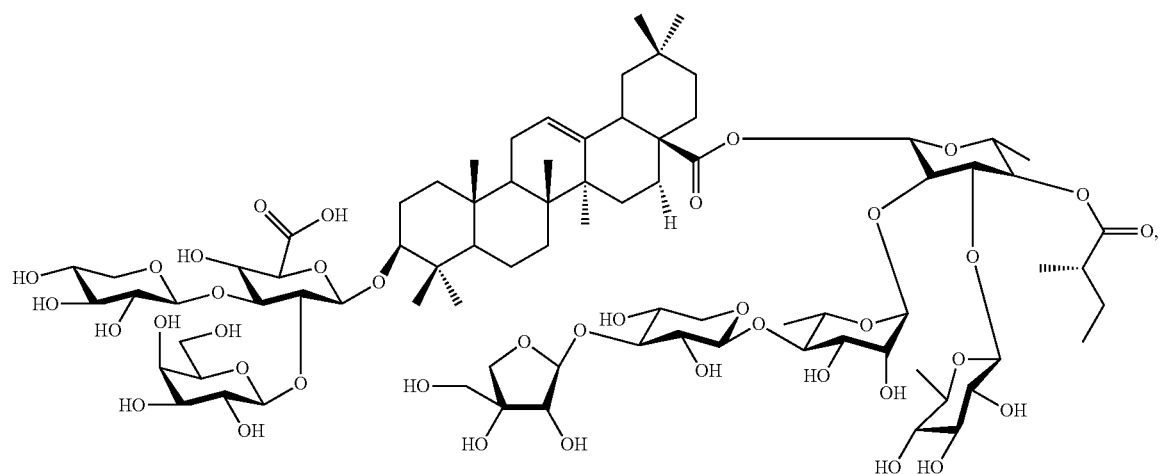

or 2118 component, at least 93%:
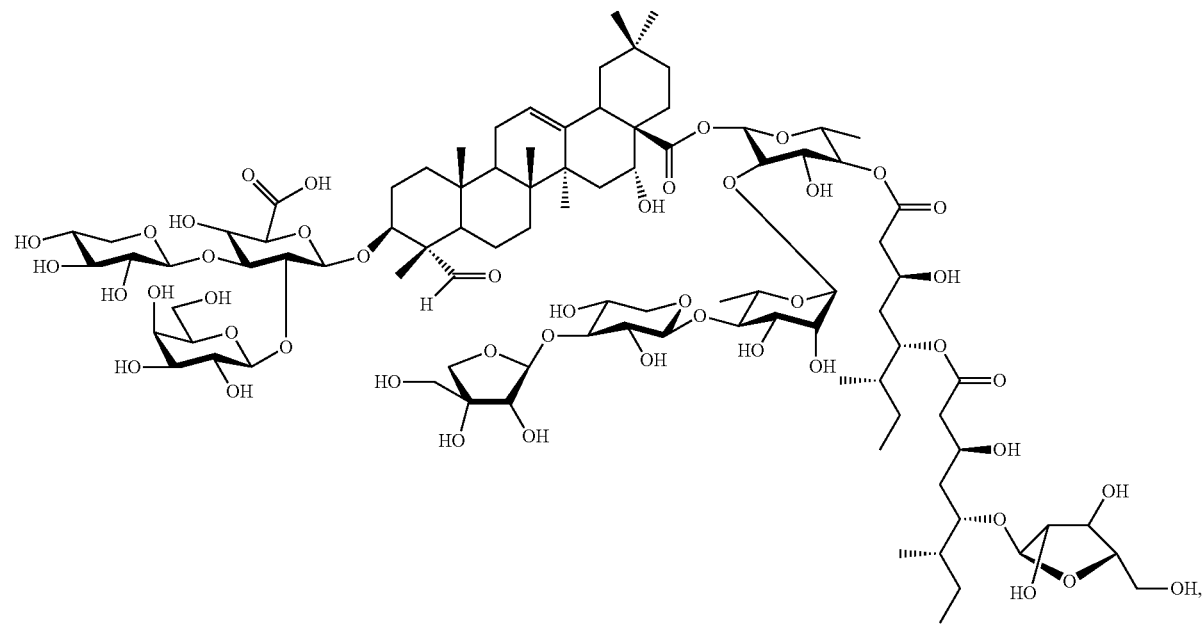
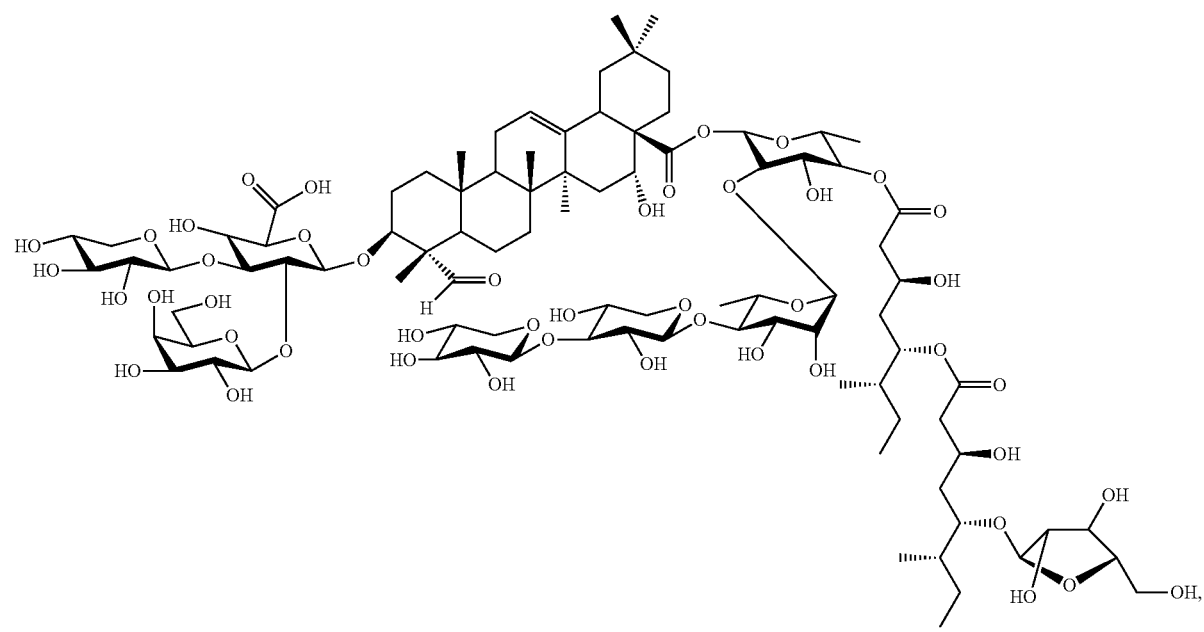

-continued
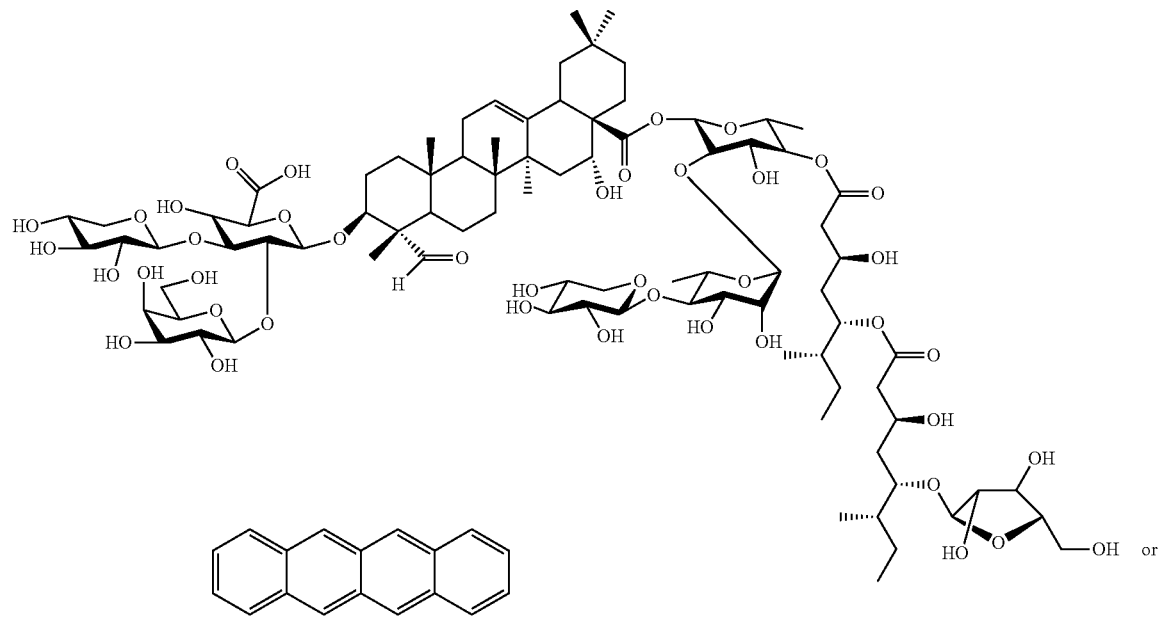
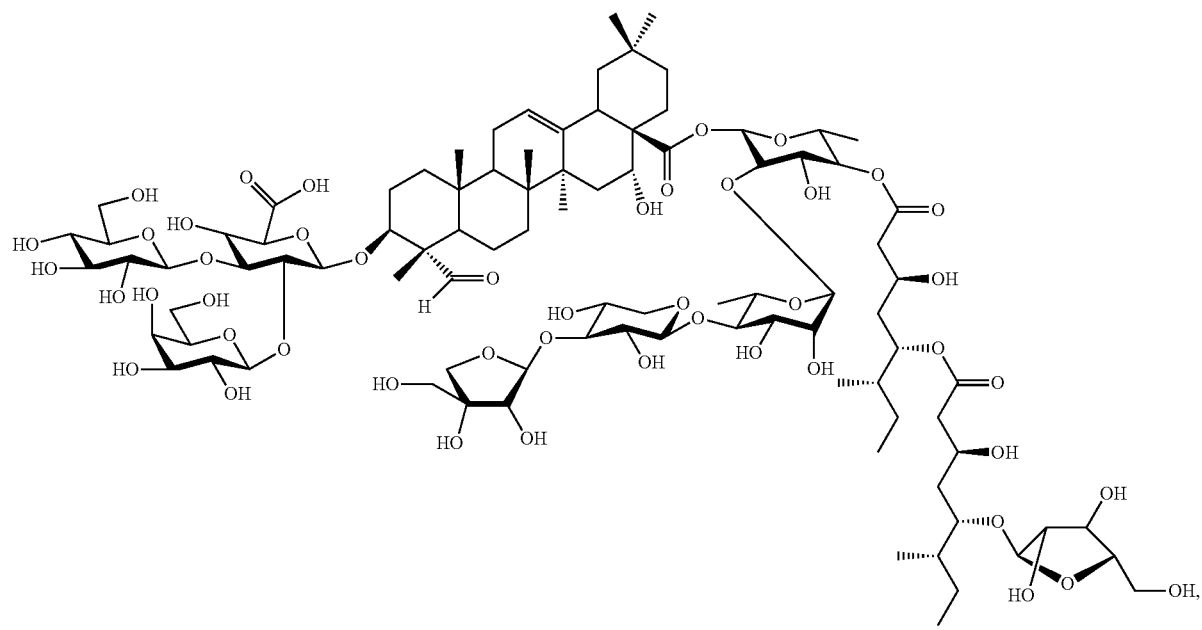

0.25-3%:

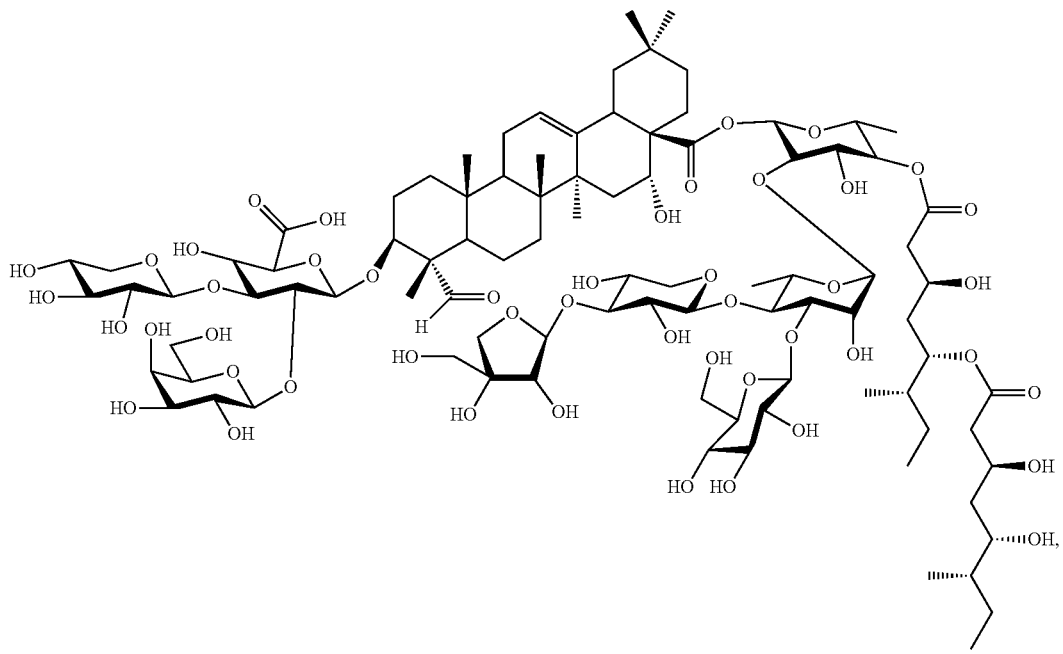

1% or less of any other peak by UV absorbance at 214 nm and wherein the monoisotope of the most abundant species is 1987.9 m/z.

In certain embodiments the saponin extracts contain at least 65%, such as at least 70%, 1988 component as determined by UV absorbance at 214 nm and by relative ion abundance. In certain embodiments the saponin extracts contain 85% or less, such as 80% or less, 1988 component as determined by UV absorbance at 214 nm and by relative ion abundance.

In certain embodiments the saponin extracts contain 30% or less, such as 25% or less, 1856 component by UV absorbance at 214 nm and by relative ion abundance. In certain embodiments the saponin extracts contain at least 5%, such as at least 10%, especially at least 15% 1856 component by UV absorbance at 214 nm and by relative ion abundance.

In certain embodiments the saponin extracts contain 6% or less, such as 4% or less, 2002 component by UV absorbance at 214 nm and by relative ion abundance. In certain embodiments the saponin extracts contain at least 0.5%, such as at least 1%, 2002 component by UV absorbance at 214 nm and by relative ion abundance.

In certain embodiments the saponin extracts contain at least 0.5%, such as at least 1%, or at least 2% 2018 component by UV absorbance at 214 nm and by relative ion abundance. In certain embodiments the saponin extracts contain at least 65%, such as at least 70%:

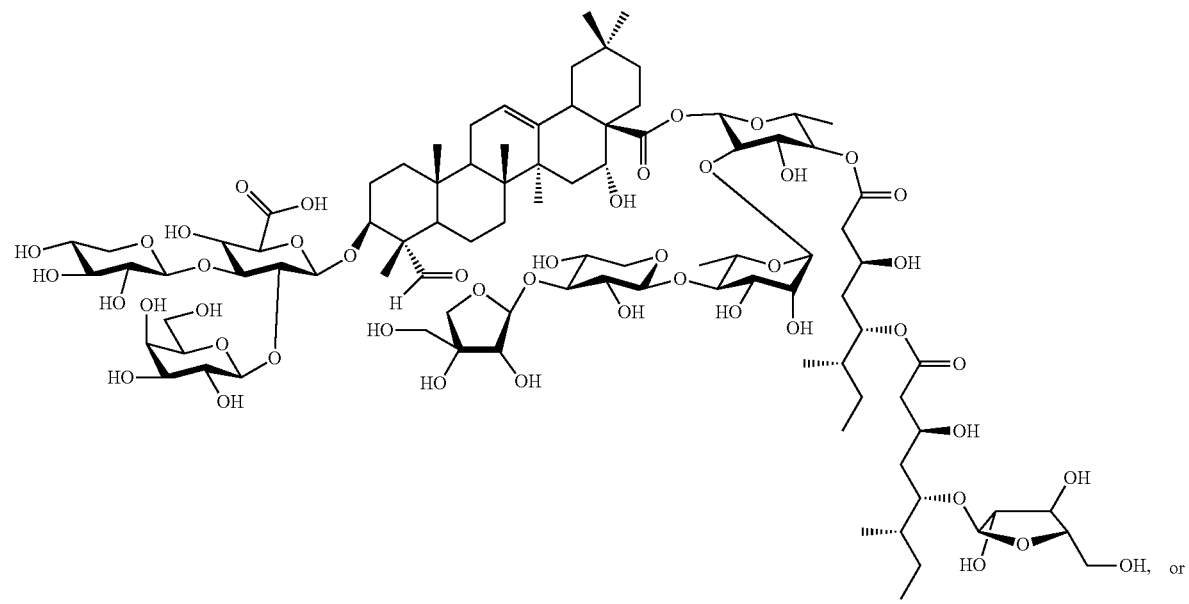

-continued
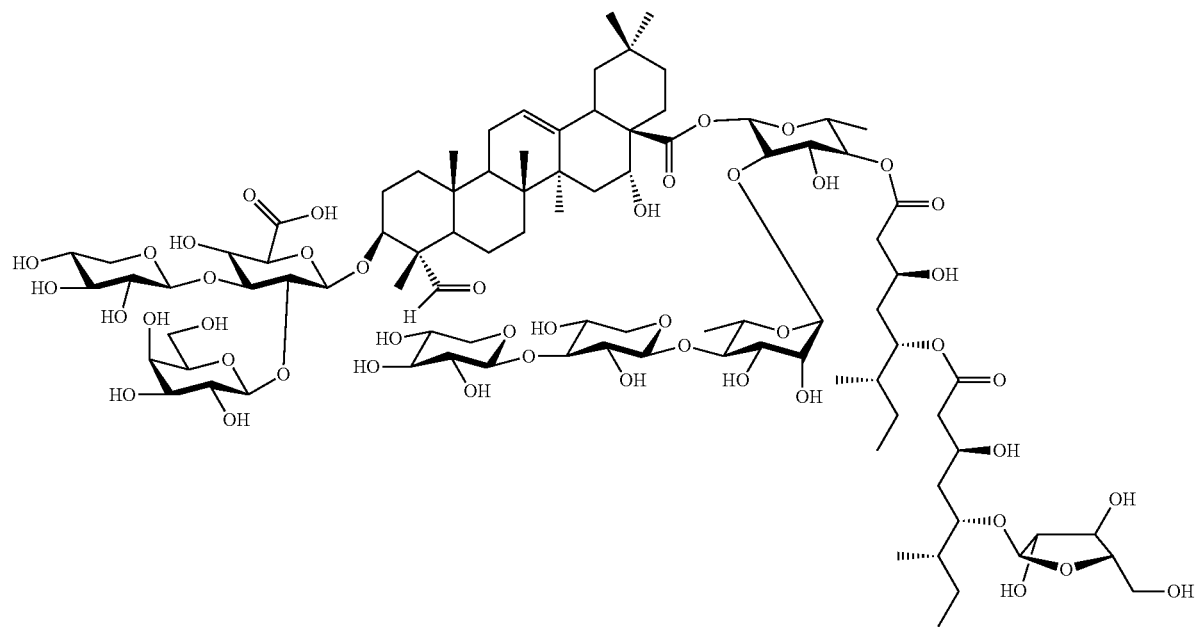
by UV absorbance at 214 nm and by relative ion abundance.
In certain embodiments the saponin extracts contain 30% or less, such as 25% or less:
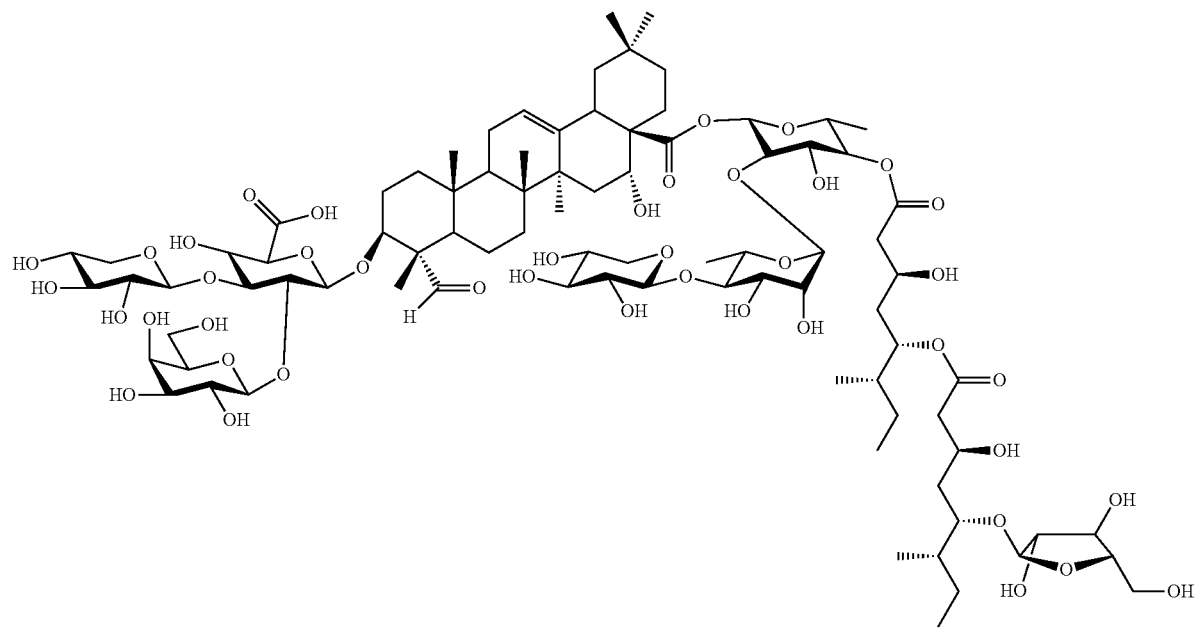

by UV absorbance at 214 nm and by relative ion abundance. In certain embodiments the saponin extracts contain at least 5%, such as at least 10%, especially at least 15%:
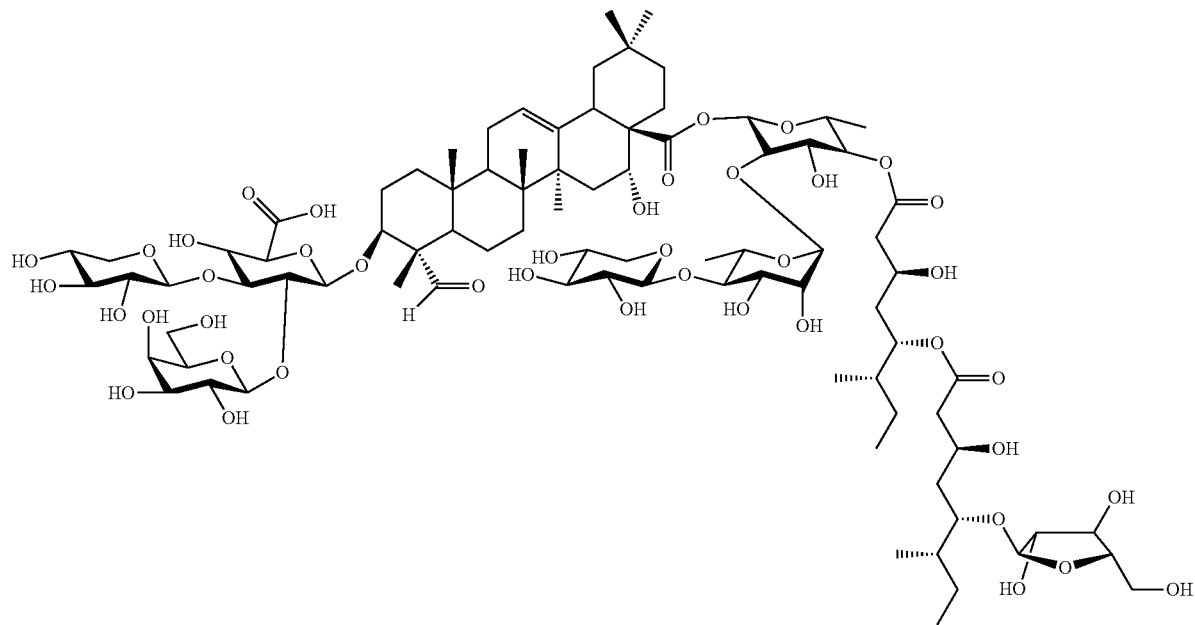
by UV absorbance at 214 nm and by relative ion abundance.
In certain embodiments the saponin extracts contain 10% or less, such as 5% or less:
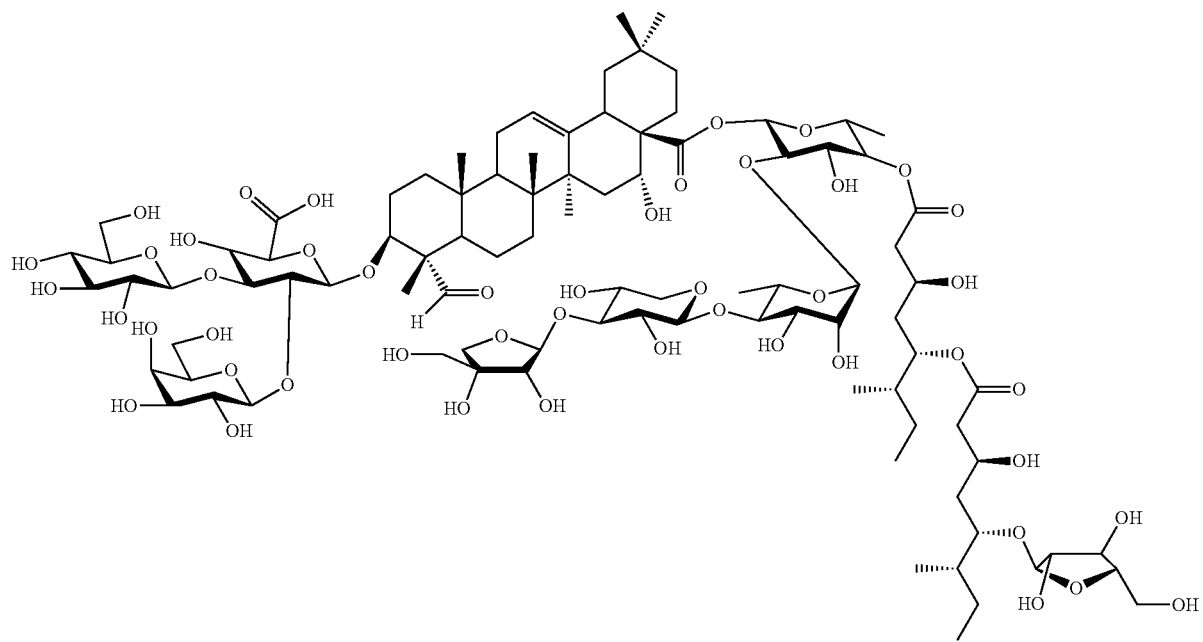

by UV absorbance at 214 nm and by relative ion abundance. In certain embodiments the saponin extracts contain at least 0.5%, such as at least 1%,

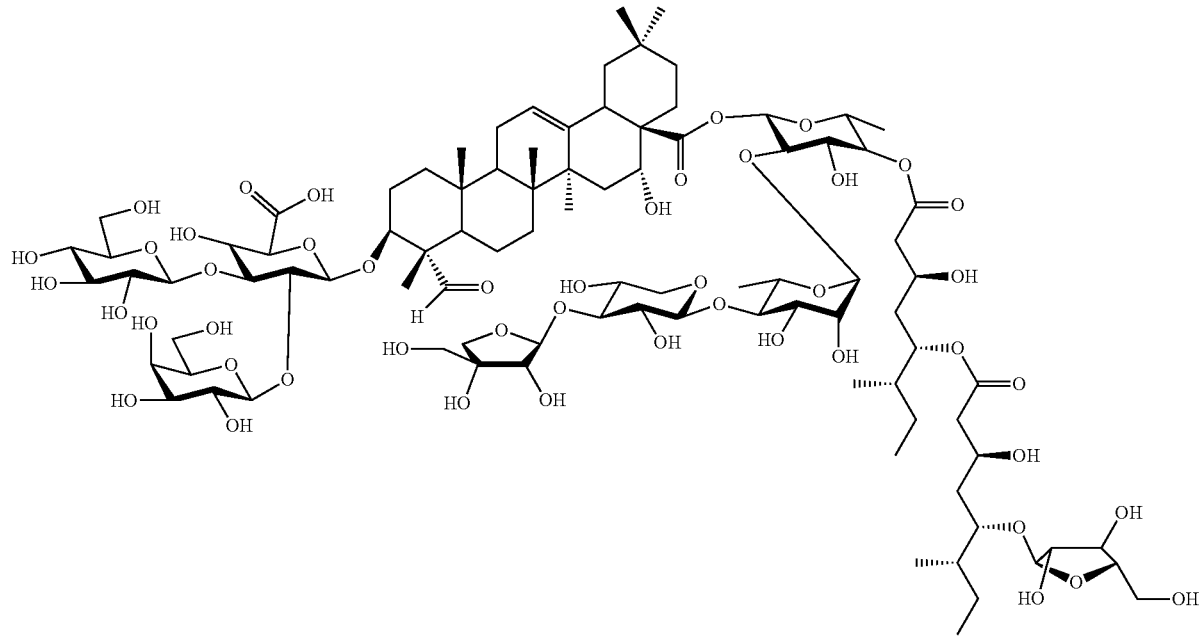

by ion abundance by UV absorbance at 214 nm and by relative ion abundance.

In certain embodiments the saponin extracts contain at least 0.5%, such as at least 1%, or at least 2%,

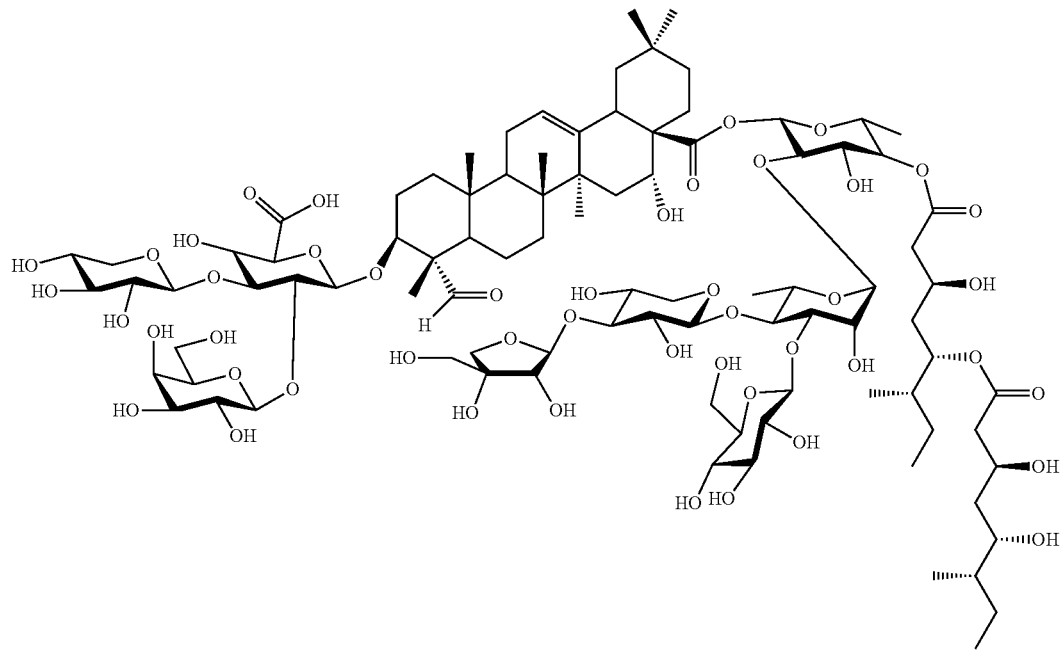

by UV absorbance at 214 nm and by relative ion abundance.

Quil A is a saponin preparation isolated from the South American tree *Quillaja saponaria* Molina and was first described as having adjuvant activity by Dalsgaard et al. in 1974 ("Saponin adjuvants", Archiv. für die gesamte Virusforschung, Vol. 44, Springer Verlag, Berlin, p 243-254). Purified fractions of Quil A have been isolated by HPLC which retain adjuvant activity without the toxicity associated with Quil A (see, for example, EP03622789). Various fractions have been found to have adjuvant activity, such as QS-7, QS-17, QS-18 and QS-21, although their toxicity varies considerably.

By the term 'saponin extract' as used herein is meant an extract of *Quillaja saponaria* Molina.

By the term 'triterpenoid glycosides' as used herein is meant an entity or entities having a triterpenoid core derivatised by sugars which are attached via glycosidic bonds.

Certain structures herein have been determined by MS/MS, limitations of the technique in differentiating certain branching, stereochemistry and isomeric sugar species (e.g. apiose and xylose) means that some structures are putative and based on an assumed conserved core. Putative structures should therefore be taken to mean the actual structure of the component which has otherwise been identified, in the event the putative structure is incorrect for any reason.

Figure 6:
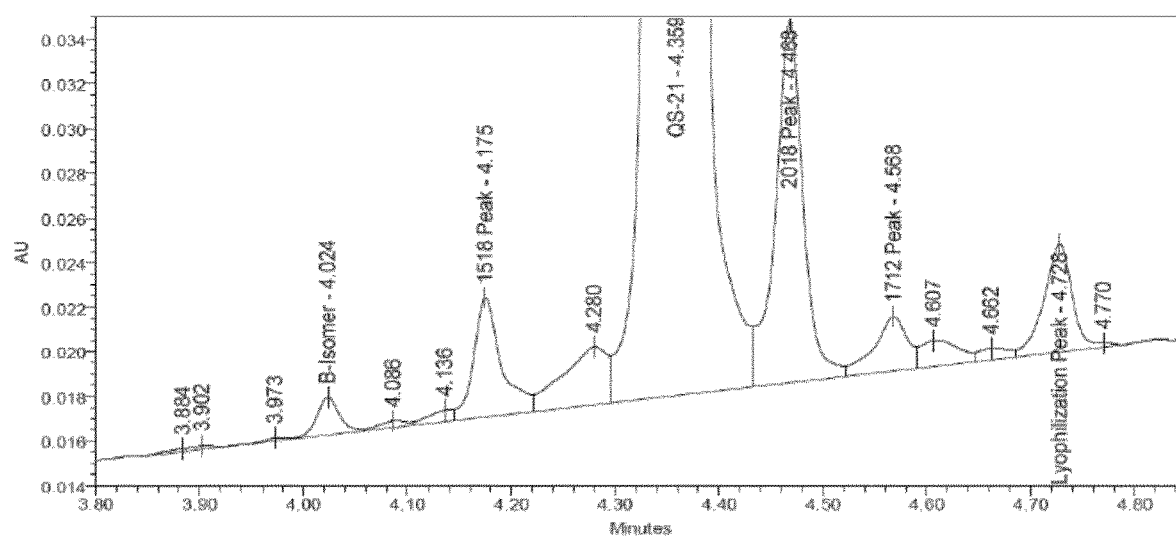

By the term '2018 component' is meant the triterpenoid glycosides identified as '2018 Peak' in FIG. 6. Suitably the 2018 component in the UPLC-UV/MS methods described herein has a retention time of approximately 4.5 min, the primary component of the peak having a monoisotopic molecular weight of 2017.9. The 2018 component may also be identified in the UPLC-UV methods described herein with a retention time of approximately 5.8 min. The primary 2018 component has been identified as having the putative structure.

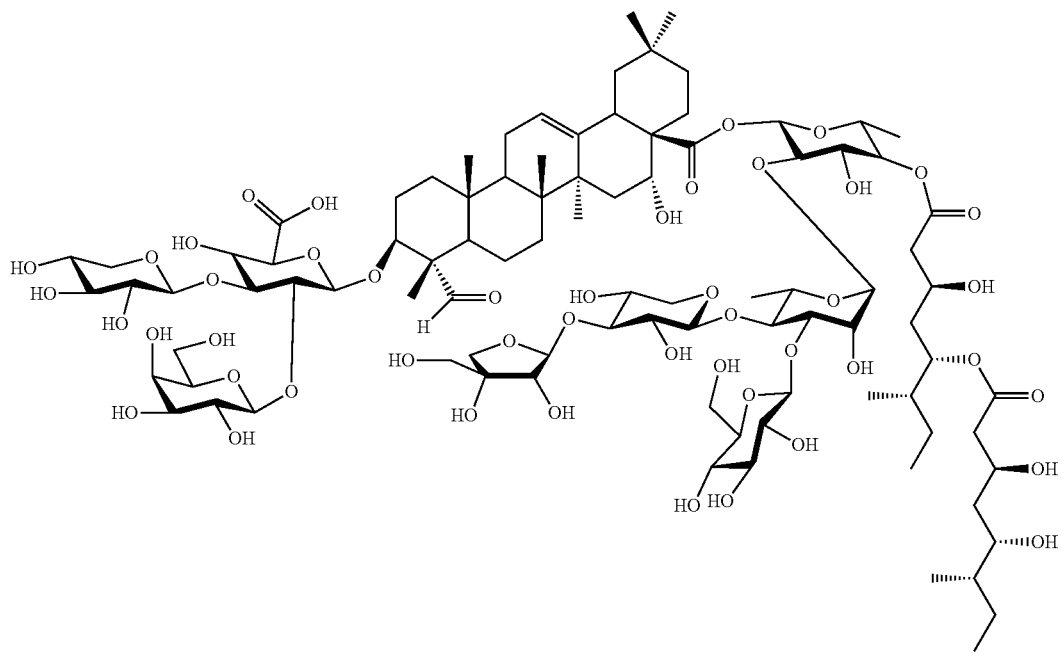

by MS/MS.

By the term '1988 component' is meant the triterpenoid glycosides identified as part of the QS-21 main peak in FIG. 6 and having a monoisotopic molecular weight of 1987.9. Suitably the 1988 component in the UPLC-UV/MS methods described herein has a retention time of approximately 4.4 min and a monoisotopic molecular weight of 1987.9. The 1988 component may consist of QS-21A V1:

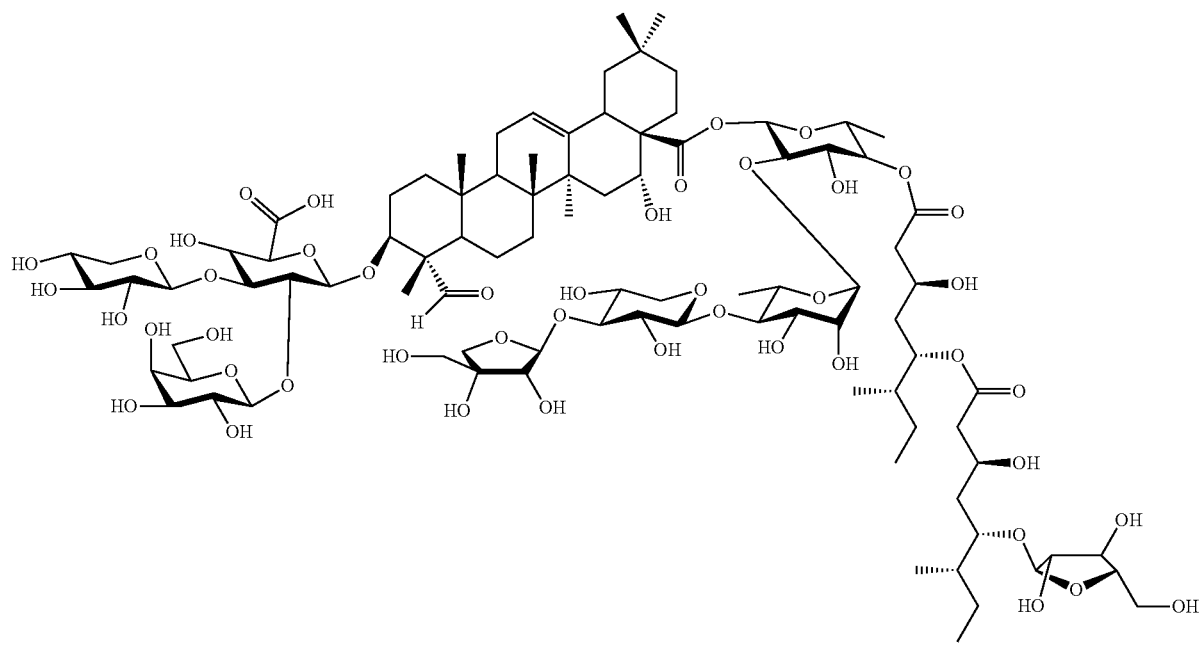
and QS-21A V2
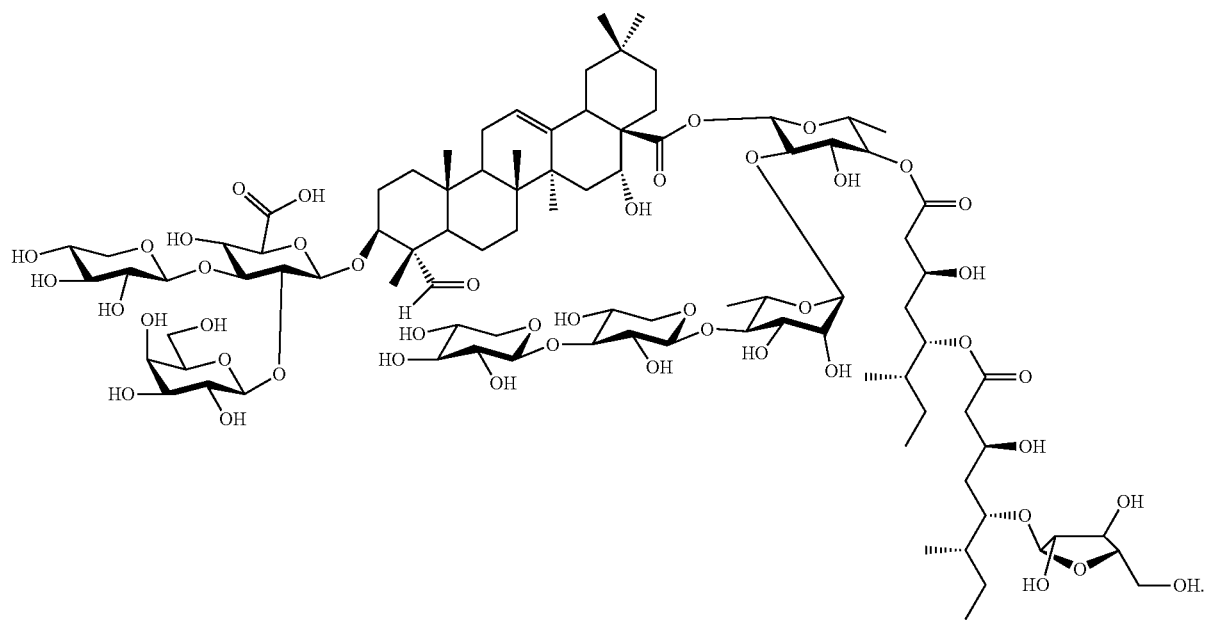
By the term '1856 component' is meant the triterpenoid glycosides identified as part of the QS-21 main peak in FIG. 6 and having a monoisotopic molecular weight of 1855.9. Suitably the 1856 component in the UPLC-UV/MS methods described herein has a retention time of approximately 4.4 min and a monoisotopic molecular weight of 1855.9. The 1856 component may consist of:

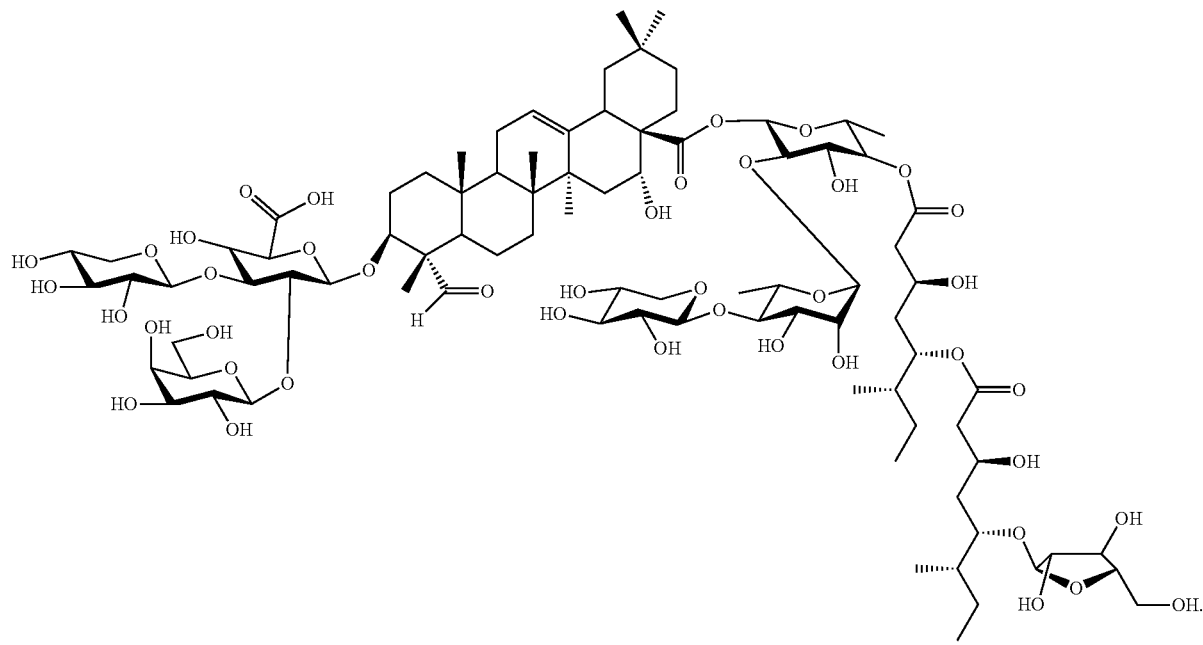

By the term '2002 component' is meant the triterpenoid glycosides identified as part of the QS-21 main peak in FIG. 6 and having a monoisotopic molecular weight of 2001.9. Suitably the 2002 component in the UPLC-UV/MS methods described herein has a retention time of approximately 4.4 min and a monoisotopic molecular weight of 2001.9. The 2002 component has been identified as having the putative structure:

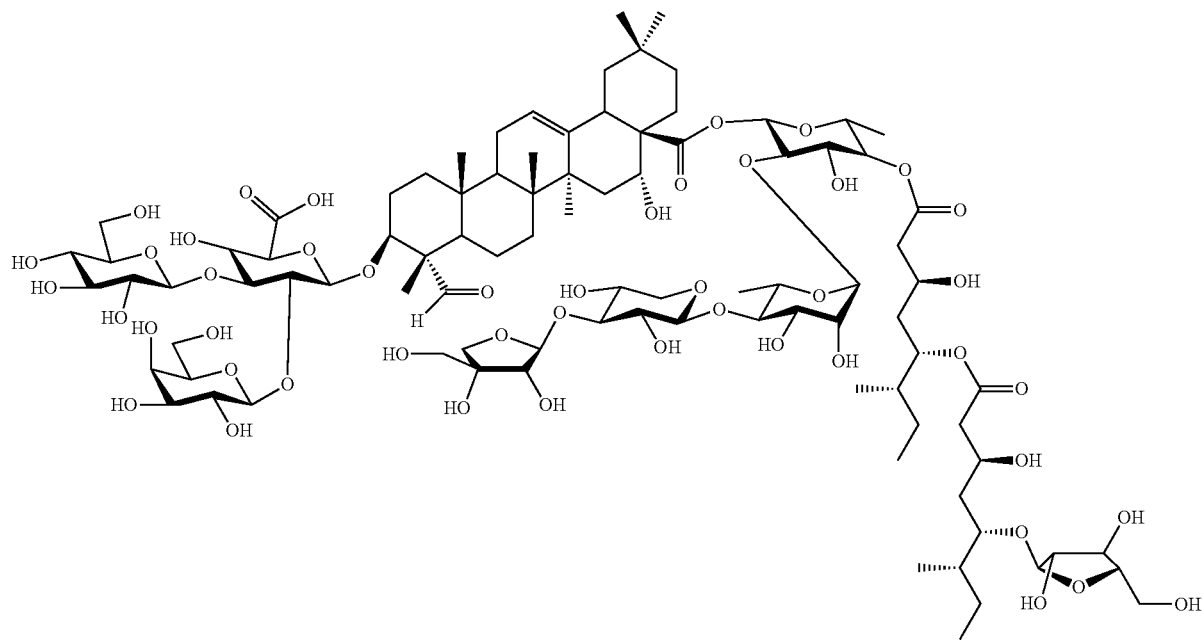

by MS/MS.

By the term 'lyo impurity' is meant the triterpenoid glycosides identified as 'Lyophilization Peak' in FIG. 6. Suitably the lyo impurity in the UPLC-UV/MS methods described herein has a retention time of approximately 4.7 min and the primary component of the peak having a monoisotopic molecular weight of 1855.9. The primary lyo impurity has been identified as having the putative structure:

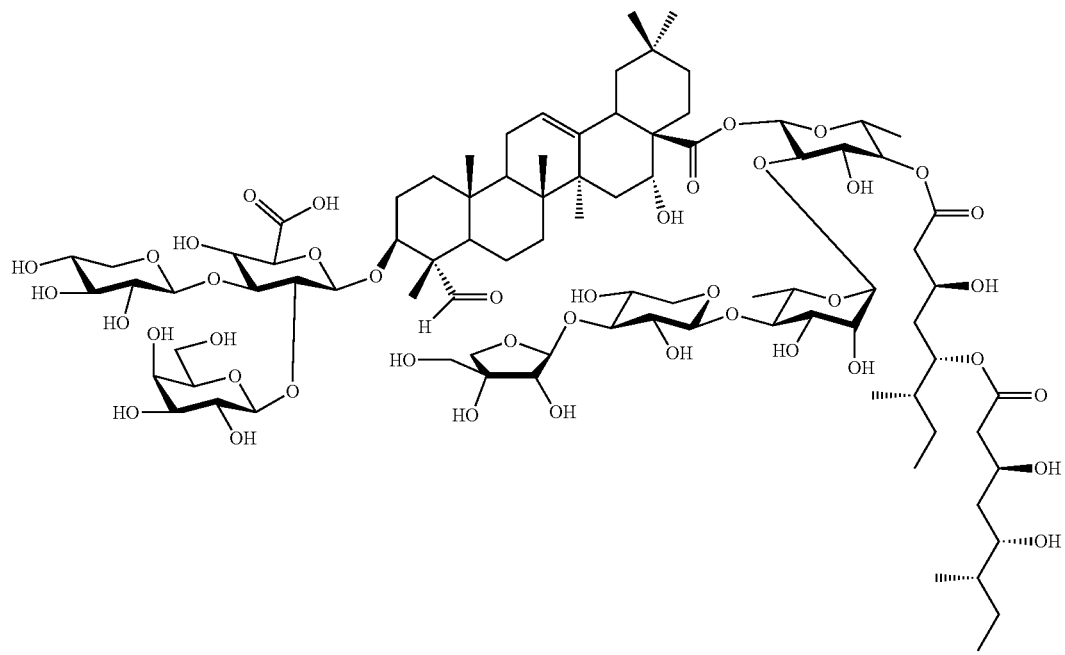

by MS/MS.

By the term 'B-isomer' is meant the triterpenoid glycosides identified as 'B-isomer' in FIG. 6. Suitably the B-isomer in the UPLC-UV/MS methods described herein has a retention time of approximately 4.0 min and the primary component of the peak having a monoisotopic molecular weight of 1987.9. The primary B-isomer component has been identified as having the putative structure:

by MS/MS.

By the term '1518 component' is meant the triterpenoid glycosides identified as '1518 Peak' in FIG. 6. Suitably the 1518 component in the UPLC-UV/MS methods described herein has a retention time of approximately 4.2 min and the primary component of the peak having a monoisotopic molecular weight of 1517.7. The primary 1518 component has been identified as having the putative structure:

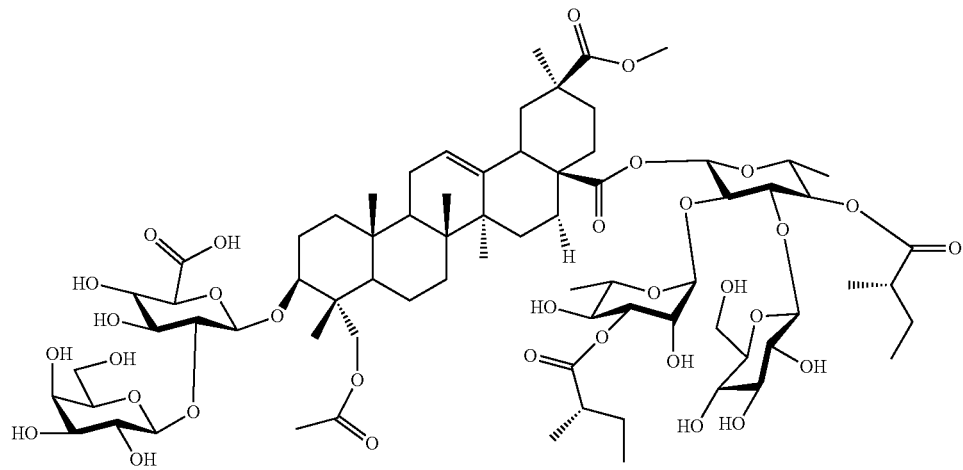

by MS/MS.

By the term '1712 component' is meant the triterpenoid glycosides identified as '1712 Peak' in FIG. 6. Suitably the 1712 component in the U PLC-UV/MS methods described herein has a retention time of approximately 4.6 min and the primary component of the peak having a monoisotopic molecular weight of 1711.8. The primary 1712 component has been identified as having the putative structure:

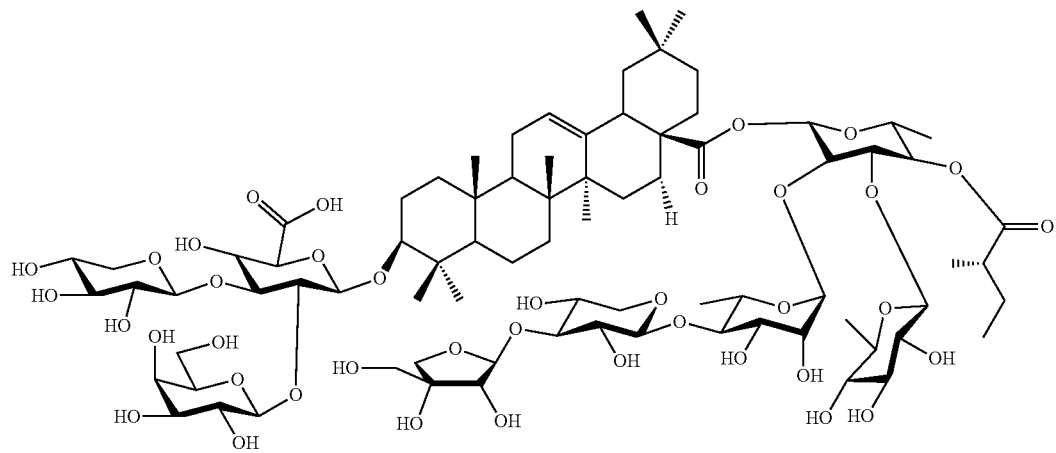

by MS/MS.

By the term '2118 component' is meant the triterpenoid glycosides identified as '4.607' in FIG. 6. Suitably the 2118 component in the UPLC-UV/MS methods described herein has a retention time of approximately 4.6 and the primary component of the peak having a monoisotopic molecular weight of 2118.

By the term 'QS-21 main peak' is meant the triterpenoid glycosides identified as 'QS-21' in FIG. 6. Suitably QS-21 main peak in the UPLC-UV/MS methods described herein has a retention time of approximately 4.4 min and molecular weight components of 1855.9, 1987.9 and 2001.9 m/z. The QS-21 main peak may consist of QS-21A V1:

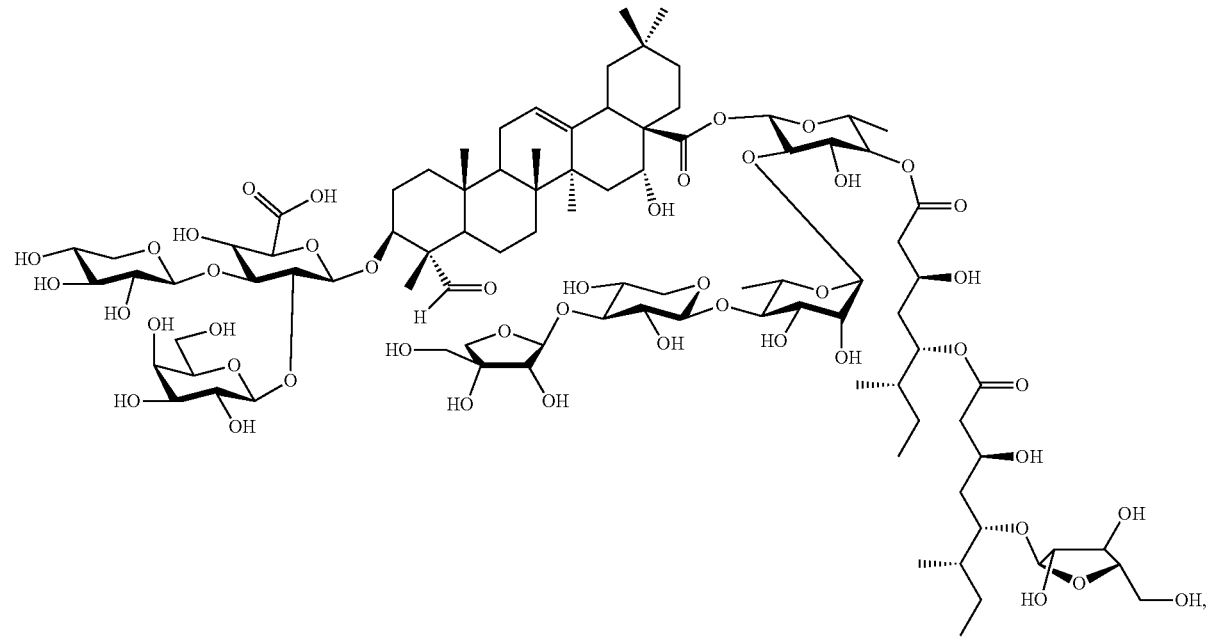
QS-21A V2:
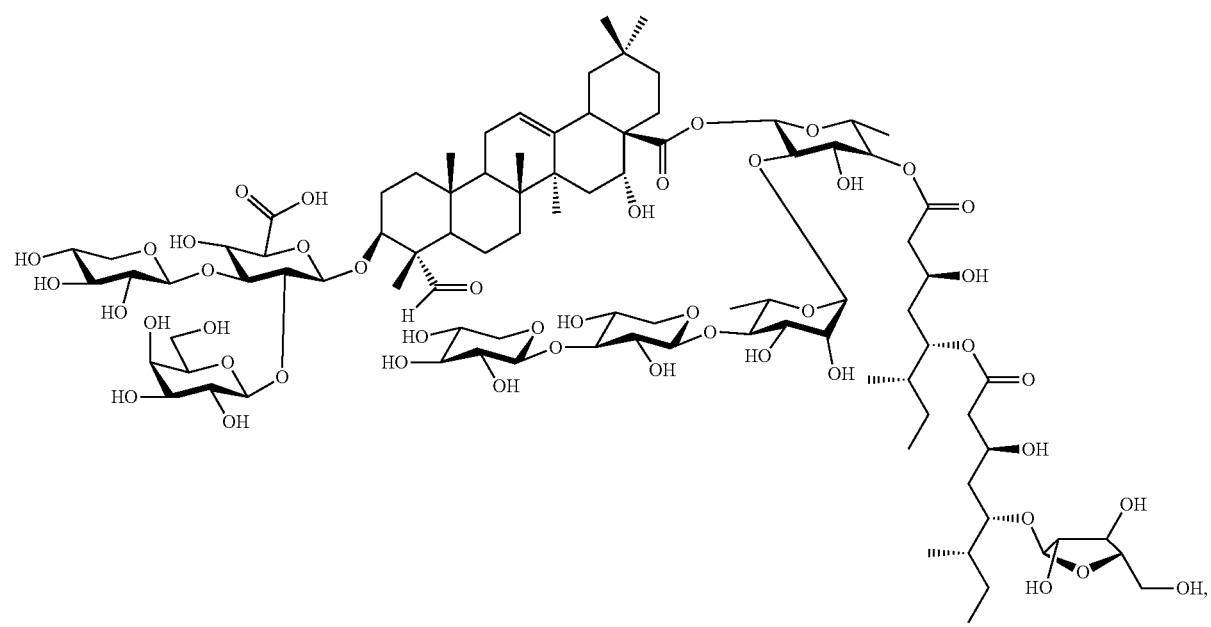

1856 component:
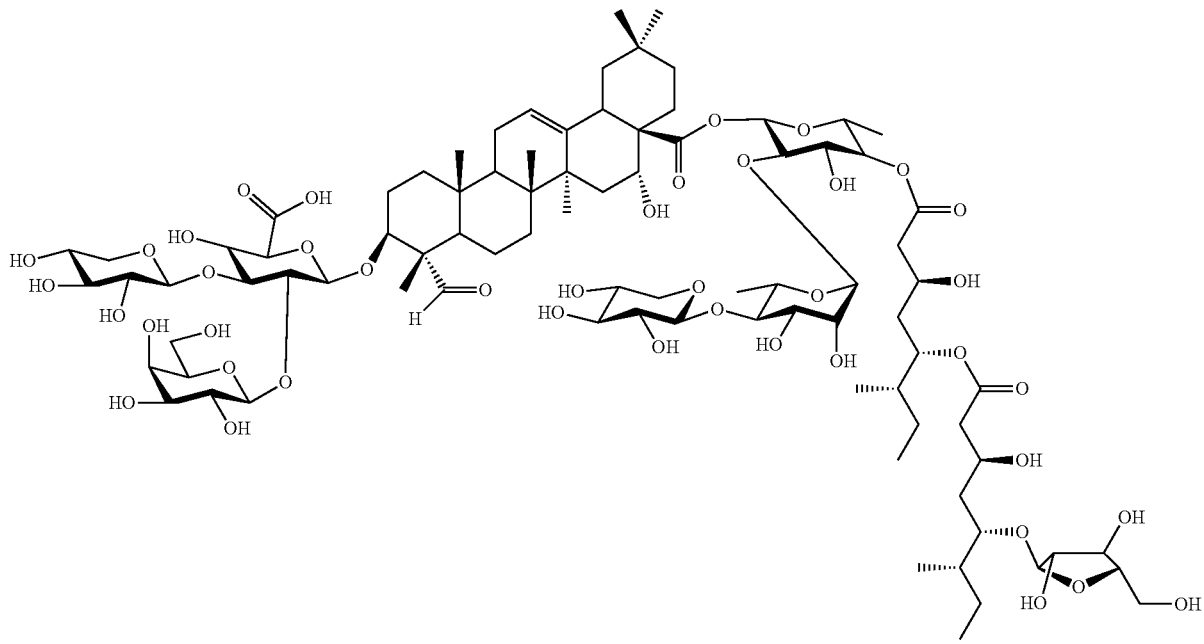
and 2002 component:
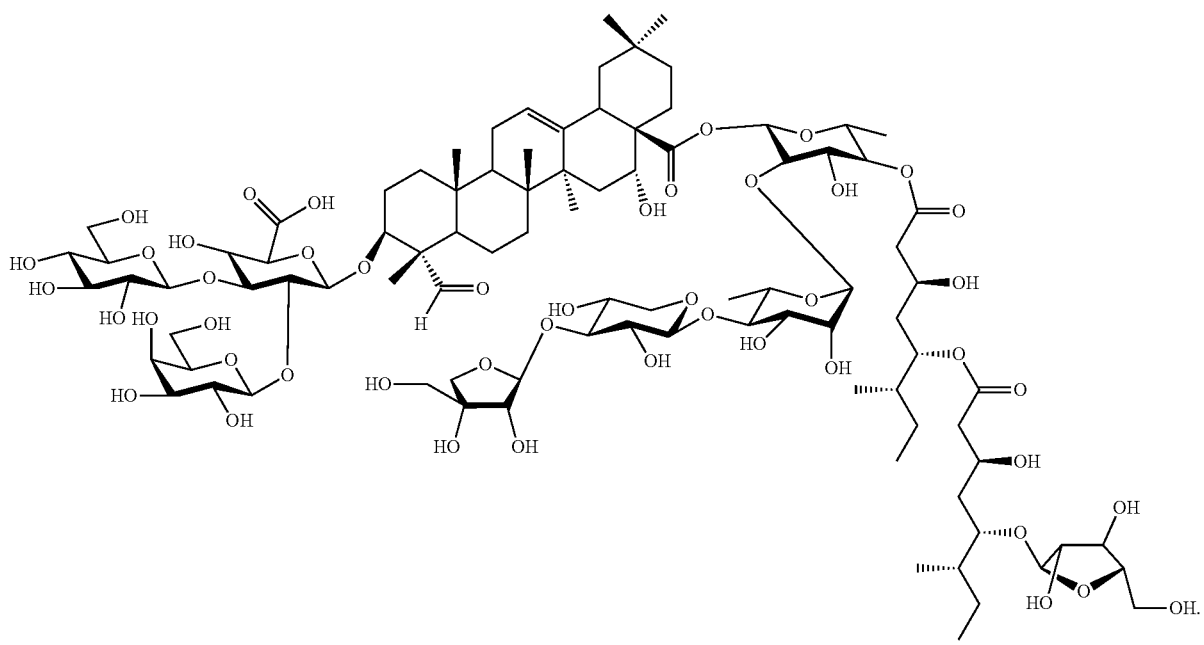
By the term 'QS-21 group' is meant the triterpenoid glycosides identified from the B-isomer to the peak preceding the lyo impurity in the UPLC-UV/MS methods described herein as having a retention time from approximately 4.0 min to approximately 4.7 min and having primary monoisotopic molecular weights of 1517.7, 1711.8, 1855.9, 1987.9, 2001.9, 2017.9 or 2118. The QS-21 group may consist of QS-21A V1:

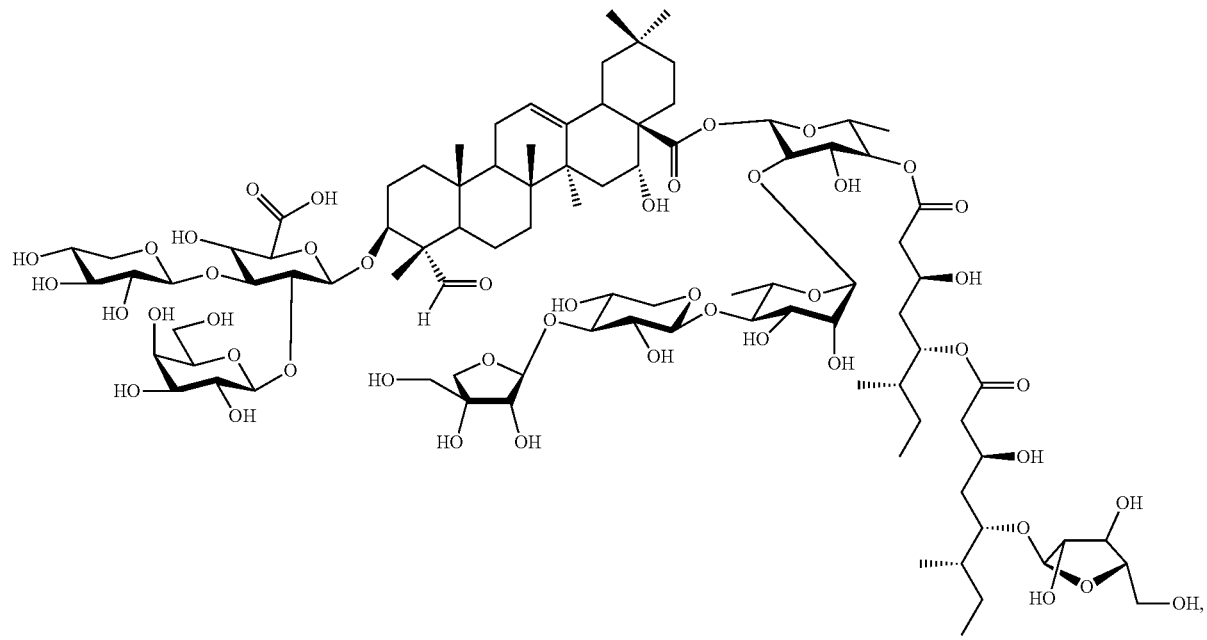
QS-21A V2:
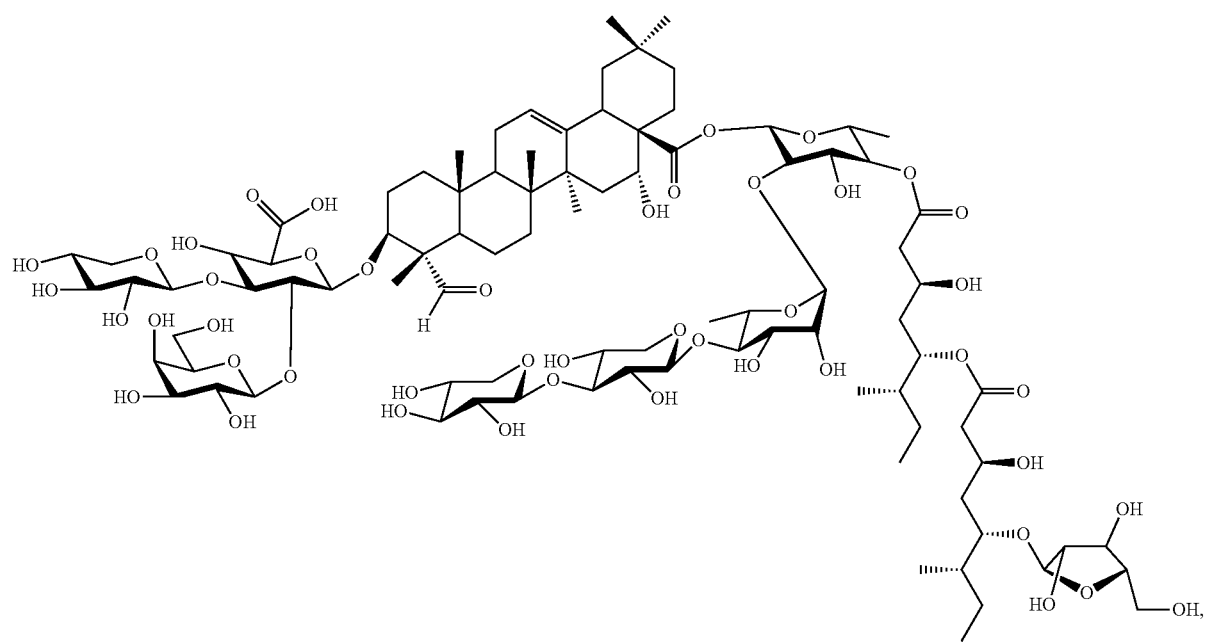

1856 component:
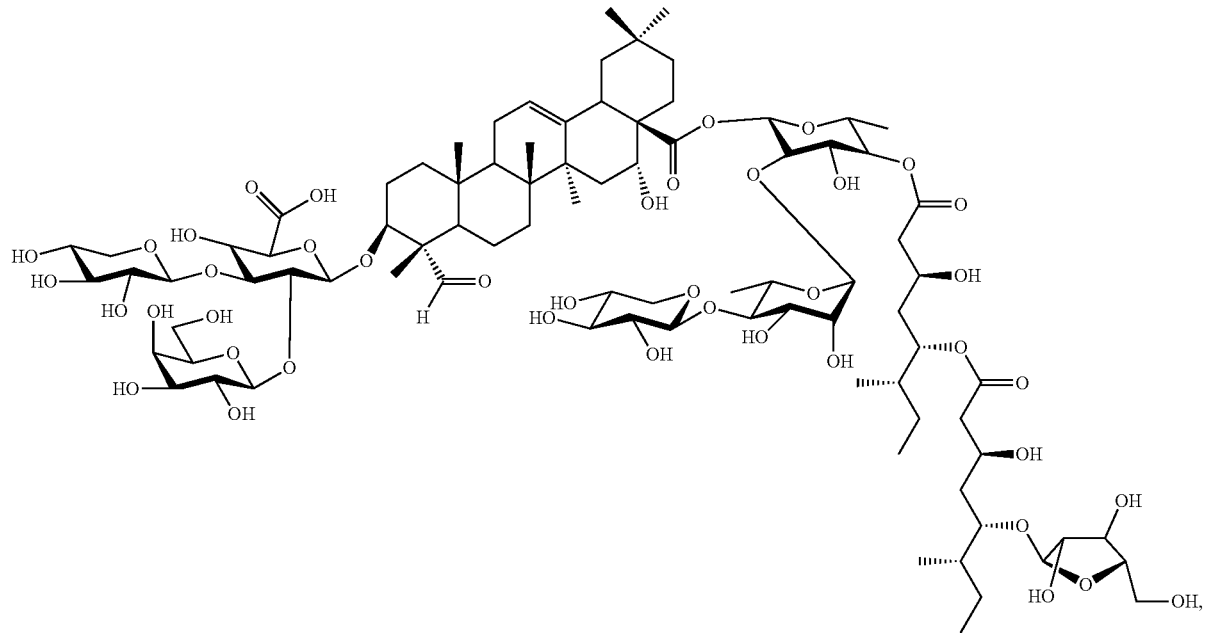
2002 component:
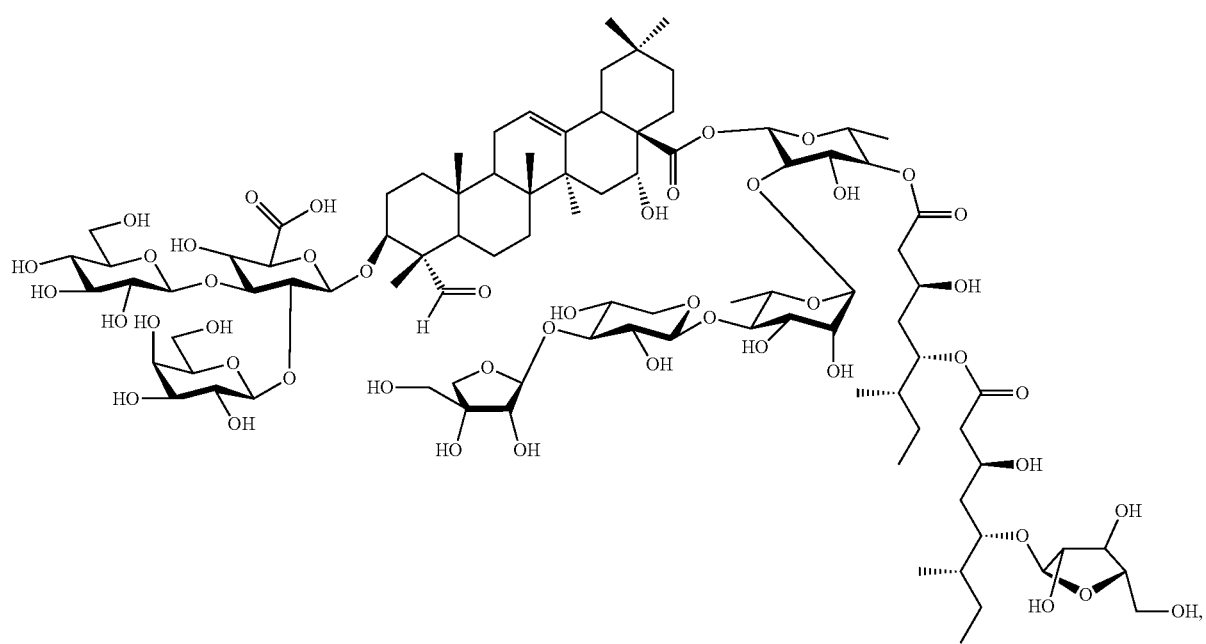

2018 component:
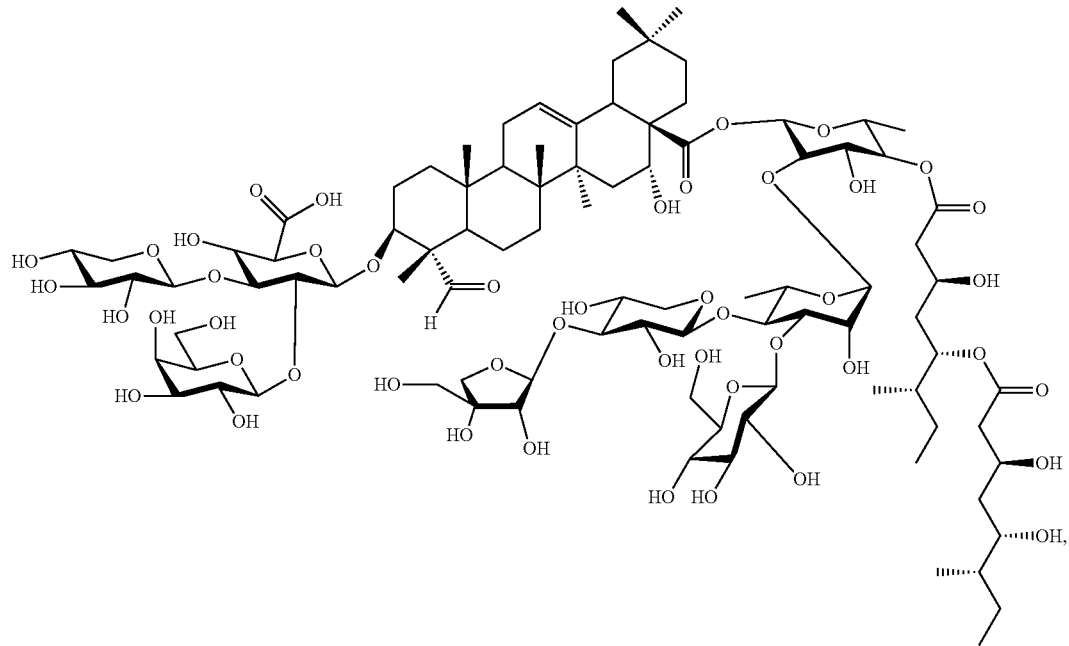
B-isomer:
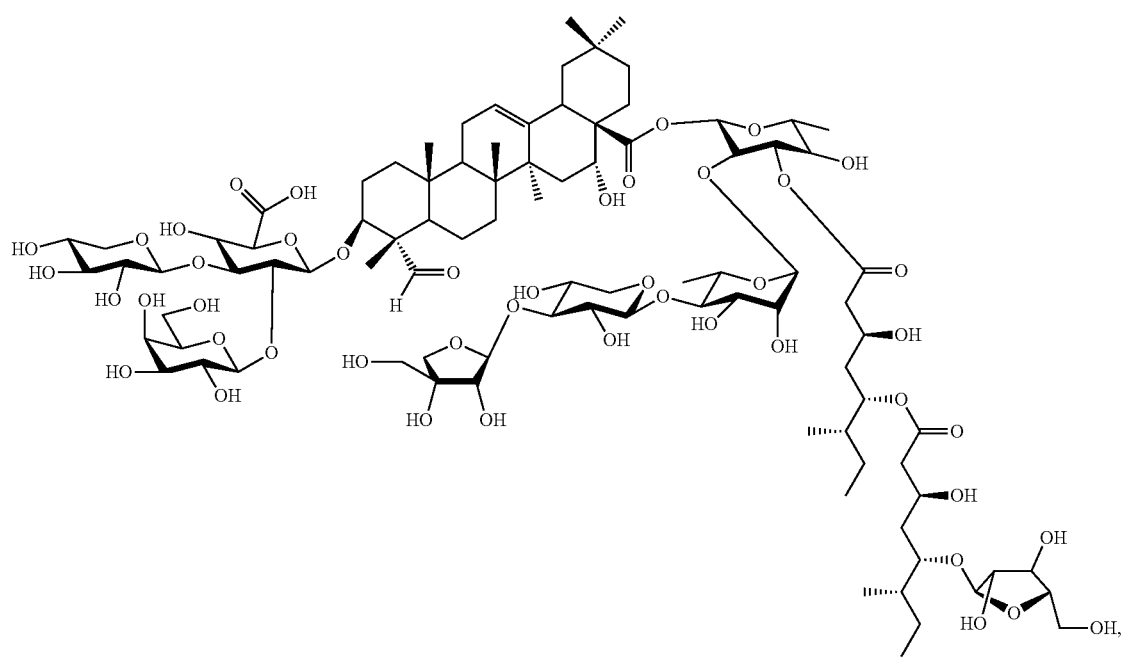

1518 component:

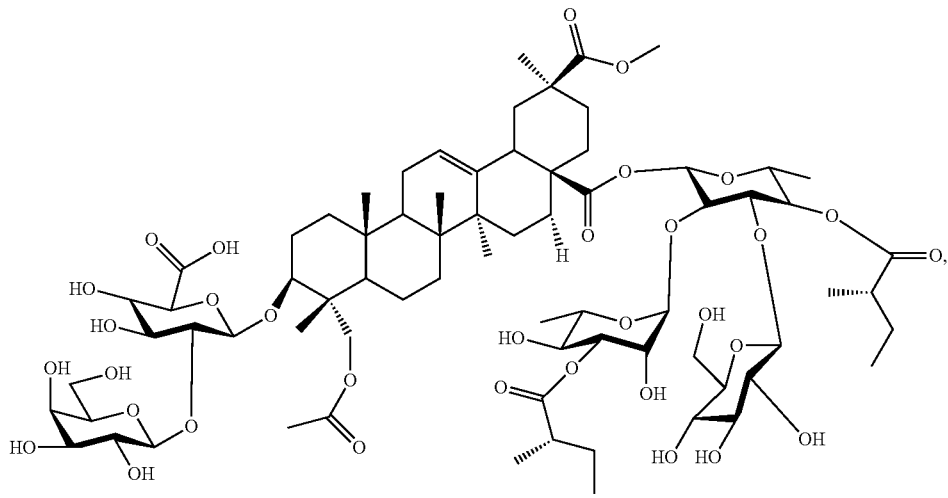

1712 component:

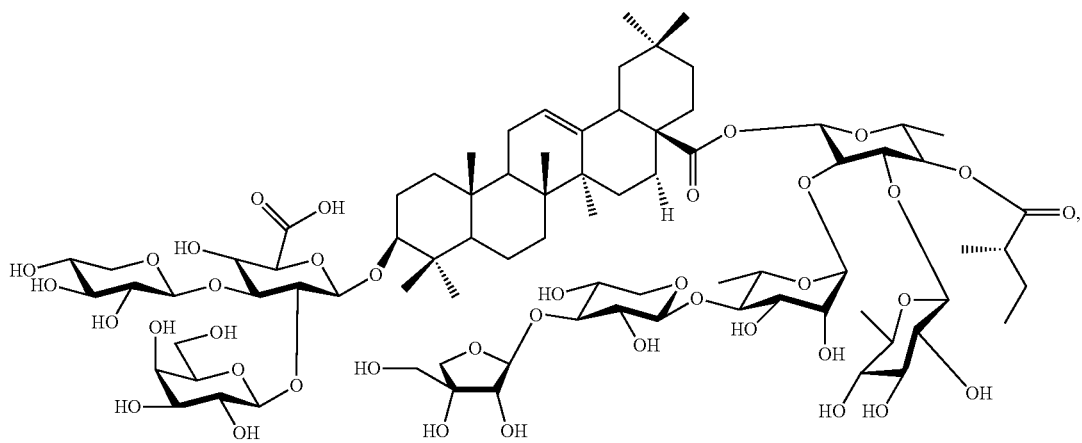

and 2118 component.

By the term 'largest peak outside QS-21 group' is meant the largest peak by UV, detectable in the UPLC-UV/MS methods described herein which is not part of the QS-21 group.

Figure 2:
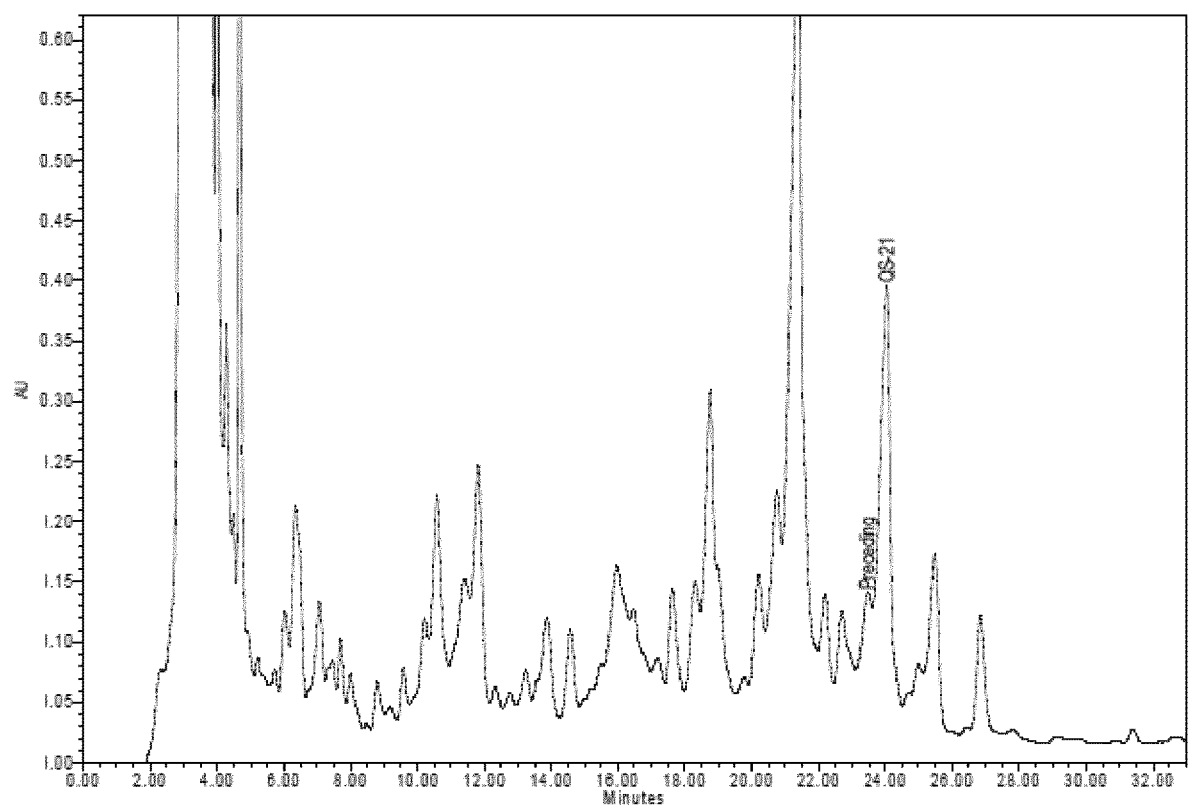

By the term 'Preceding peak' is meant the peak immediately preceding the QS-21 main peak in the HPLC-UV methods described herein (see FIG. 2).

By the term 'm/z' is meant the mass to charge ratio of the monoisotope peak. Unless otherwise specified, 'm/z' is determined by negative ion electrospray mass spectrometry.

By the term 'ion abundance' is meant the amount of a specified m/z measured in the sample, or in a given peak as required by the context. The mass chromatogram for the specified m/z may be extracted from the MS total ion chromatogram in the UPLC-UV/MS methods described herein. The mass chromatogram plots the signal intensity versus time. Ion abundance is measured as the area of the integrated peak. The area for a specified m/z/area for a relative reference m/z=relative abundance.

By the term 'UV absorbance at 214 nm' is meant the area of an integrated peak in the UV absorbance chromatogram. The (area for a specified peak)/(area of all integrated peaks in the chromatogram)×100=percentage area for the specified peak.

By the term 'UV absorbance at 214 nm and relative ion abundance' is meant an estimate for the percentage of a given m/z for co-eluting species. (Percentage area for given UV peak)×(relative ion abundance for m/z of interest in given peak)/(sum of all relative ion abundance for given peak)=percentage of m/z of interest in the given UV peak, assumes relative ion abundance included for all coeluting species.

By the term 'wherein the monoisotope of the most abundant species is 1988 m/z' is meant the monoisotope of the most abundant species, first peak in the isotopic group with highest response per m/z should be m/z 1987.9. The most abundant species may be determined by creating a combined spectrum across the entire total ion chromatogram using the UPLC-UV/MS method (negative ion electrospray) as described herein.

By the term 'dried' is meant that substantially all solvent has been removed. A dried extract will typically contain less than 5% solvent w/w (such as less than 5% water w/w).

Suitably the dried extract will contain 100 ppm or less acetonitrile (w/w).

Further, there is provided a method for the manufacture of a saponin extract comprising the steps of:
(i) selecting a crude aqueous extract of *Quillaja saponaria* Molina having a suitable 2018 component composition;
(ii) purifying the extract by reverse phase chromatography using a polystyrene resin; and
(iii) purifying the extract by reverse phase chromatography using a phenyl resin.

Desirably the process comprises the steps of:
(i) selecting a crude aqueous extract of *Quillaja saponaria* Molina having a suitable 2018 component composition;
(ii) purifying the extract by polyvinylpyrollidone adsorption;
(iii) purifying the extract by diafiltration, ultrafiltration or dialysis;
(iv) purifying the extract by reverse phase chromatography using a polystyrene resin; and
(v) purifying the extract by reverse phase chromatography using a phenyl resin;
wherein step (ii) and (iii) may optionally be in reverse order or undertaken concurrently, though are typically in the order shown.

The crude aqueous extract of *Quillaja saponaria* Molina is obtained by aqueous extraction (but need not be in aqueous form, e.g. it may subsequently have been dried, subjected to solvent exchange or reconstituted into a different solvent). By the term 'crude aqueous extract of *Quillaja saponaria* Molina having a suitable 2018 component composition' is meant an extract having a 2018 component to QS-21 main peak ratio of 0.075 or lower, in particular 0.064 or lower (as determined by UPLC-UV absorbance at 214 nm). Desirably the ratio of 2018 component/QS-21 main peak is at least 0.005, such as at least 0.01 as measured by UV absorbance at 214 nm.

Suitably the Preceding peak to QS-21 main peak ratio is 0.45 or lower, in particular 0.4 or lower (as determined by HPLC-UV absorbance at 214 nm). The Preceding peak to QS-21 main peak ratio may be 0.05 or higher, in particular 0.1 or higher (as determined by HPLC-UV absorbance at 214 nm).

Typically the crude aqueous extract is a bark extract. Suitably the QS-21 main peak content in an aqueous solution of crude aqueous extract of *Quillaja saponaria* Molina is at least 1 g/L, such as at least 2 g/L, especially at least 2.5 g/L and in particular at least 2.8 g/L (e.g. as determined by UV absorbance relative to a control sample of known concentration).

Suitably the step of selecting a crude aqueous extract of *Quillaja saponaria* Molina having a suitable 2018 component composition, includes testing the composition to determine the 2018 component content.

The step of purifying the extract by polyvinylpyrollidone adsorption involves treatment of the extract with polyvinylpyrollidone resin. Typically the extract is agitated with the polyvinylpyrollidone resin. The extract may subsequently be separated from the polyvinylpyrollidone resin with adsorbed impurities by filtration. This step of the process generally removes polyphenolic impurities such as tannins.

The step of purifying the extract by diafiltration, ultrafiltration or dialysis, is suitably purification by diafiltration, typically using tangential flow. An appropriate example of a membrane is a 30 kDa cut-off. This step of the process generally removes salts, sugars and other low molecular weight materials.

The step of purifying the extract by reverse phase chromatography using a polystyrene resin typically uses acetonitrile and water as solvent, usually acidified with a suitable acid such as acetic acid. An example of a suitable resin is Amberchrom XT20. Chromatography may be undertaken using isocratic conditions, though is typically operated under a solvent gradient (continuous, such as linear, or stepped), such as those provided in the Examples. This step of the process generally removes non-saponin material and enriches the desired saponins. Selected fractions may be pooled to maximise yield of material matching the required criteria (typically % QS-21$\geq$18%, as determined by UV absorbance following HPLC-UV and 2018/QS-21 Ratio$\leq$0.054, as determined by UV absorbance following UPLC-UV). Each polystyrene chromatography run is typically at a scale of between 25-200 g of QS-21, such as between 50-150 g and in particular between 70-110 g (amounts being based on QS-21 main peak content in the material by UV).

Purifying the extract by reverse phase chromatography using a phenyl resin typically uses acetonitrile and water as solvent, usually acidified with a suitable acid such as acetic acid. Chromatography may be undertaken using a solvent gradient (continuous, such as linear, or stepped), though is typically operated under isocratic conditions. This step of the process provides the final purification of the desired saponins. Selected fractions may be pooled to maximise yield of material matching the required criteria (typically % QS-21 group$\geq$98.5, % QS-21 main peak$\geq$94.5, 2002/1988$\leq$0.027, % 2018$\leq$2.7%, main peak outside of the QS-21 group 1%, as determined by UPLC-UV/MS). Each phenyl chromatography run is typically at a scale of between 4-40 g of QS-21, such as between 10-30 g and in particular between 13-21 g (amounts being based on QS-21 main peak content in the material by UV).

The method may comprise the further step of removing solvent to provide a dried saponin extract. Consequently, the invention provides a method for the manufacture of a saponin extract comprising the steps of:
(i) selecting a crude aqueous extract of *Quillaja saponaria* Molina having a suitable 2018 component composition;
(ii) purifying the extract by reverse phase chromatography using a polystyrene resin;
(iii) purifying the extract by reverse phase chromatography using a phenyl resin; and
(iv) removing solvent to provide a dried saponin extract.

The invention also provides a method for the manufacture of a saponin extract comprising the steps of:
(i) selecting a crude aqueous extract of *Quillaja saponaria* Molina having a suitable 2018 component composition;
(ii) purifying the extract by polyvinylpyrollidone adsorption;
(iii) purifying the extract by diafiltration, ultrafiltration or dialysis;
(iv) purifying the extract by reverse phase chromatography using a polystyrene resin;
(v) purifying the extract by reverse phase chromatography using a phenyl resin; and
(vi) removing solvent to provide a dried saponin extract.
wherein step (ii) and (iii) may optionally be in reverse order or undertaken concurrently, though are typically in the order shown.

In order to improve drying efficiency, it may be desirable to undertake further steps of concentrating the extract, such as by capture and release using an appropriate technique, for example reverse phase chromatography (e.g. using a C8 resin), and/or exchanging the solvent in advance of the drying step.

Also provided is a method for the manufacture of a saponin extract comprising the steps:
(i) selecting a crude aqueous extract of *Quillaja saponaria* Molina having a suitable 2018 component composition;
(ii) purifying the extract by polyvinylpyrollidone adsorption;
(iii) purifying the extract by diafiltration, ultrafiltration or dialysis;
(iv) purifying the extract by reverse phase chromatography using a polystyrene resin;
(v) purifying the extract by reverse phase chromatography using a phenyl resin;
(vi) optionally concentrating the extract;
(vii) optionally exchanging the solvent; and
(viii) removing the remaining solvent to provide a dried saponin extract;
wherein steps (vi) and (vii) may be optionally be in reverse order or undertaken concurrently, though are typically in the order shown.

Also provided is a method for the manufacture of a saponin extract comprising the steps:
(i) selecting a crude aqueous extract of *Quillaja saponaria* Molina having a suitable 2018 component composition;
(ii) purifying the extract by polyvinylpyrollidone adsorption;
(iii) purifying the extract by diafiltration, ultrafiltration or dialysis;
(iv) purifying the extract by reverse phase chromatography using a polystyrene resin;
(v) purifying the extract by reverse phase chromatography using a phenyl resin;
(vi) concentrating the extract by reverse phase chromatography using a C8 resin;
(vii) exchanging the solvent; and
(viii) removing the remaining solvent to provide a dried saponin extract.

Concentration of the extract may be performed using any suitable technique. For example, concentration may be performed using a capture and release methodology, such as reverse phase chromatography, in particular using a C8 resin. The reverse phase chromatography typically uses acetonitrile and water as solvent, usually acidified with a suitable acid such as acetic acid. Chromatography is typically operated under a solvent gradient, with the saponin extract captured in low organic solvent and eluted in high organic solvent, in particular a stepped solvent gradient.

Exchanging the solvent may be performed using any suitable technique, in particular diafiltration, ultrafiltration or dialysis, especially diafiltration. Solvent exchange may be useful, for example, in reducing the acetonitrile content such as described in WO2014016374. A suitable membrane may be selected to allow solvent exchange while retaining the saponin extract, such as a 1 kDa membrane.

Drying, by removing the solvent, may be undertaken by any suitable means, in particular by lyophilisation. During drying, degradation of the saponin extract can occur, leading to the formation of lyo impurity. Consequently, it is desirable to dry under conditions which limit formation of lyo impurity, such as by limiting the drying temperature and/or drying time. Suitably removal of solvent is undertaken by a single lyophilisation process. The extent of drying required will depend on the nature of the solvent, for example non-pharmaceutically acceptable solvents will desirably be removed to a high degree, whereas some pharmaceutically acceptable solvents (such as water) may be removed to a lesser degree.

Suitably the methods of the present invention are undertaken at a scale of between 25-1000 g of QS-21, such as between 50-500 g and in particular between 100-500 g (amounts being based on QS-21 main peak content in the material by UV).

Also provided is a method for identifying a crude aqueous extract of *Quillaja saponaria* Molina for use in the manufacture of a purified saponin extract, such as the saponin extracts of the invention, said method comprising the steps of:
(i) determining the 2018 component to QS-21 main peak ratio by UPLC-UV absorbance at 214 nm;
(ii) selecting a crude extract having a 2018 component to QS-21 main peak ratio of 0.075 or lower.

In one embodiment, the crude aqueous extract selected in step (ii) has a 2018 component to QS-21 main peak ratio of 0.064 or lower.

The invention also provides a method for the determining the 2018 component to QS-21 main peak ratio in a crude aqueous extract of *Quillaja saponaria* Molina, said method comprising the steps of:
(i) determining the 2018 component content in the crude aqueous extract of *Quillaja saponaria* Molina by UPLC-UV absorbance at 214 nm;
(ii) determining the QS-21 main peak content in the crude aqueous extract of *Quillaja saponaria* Molina by UPLC-UV absorbance at 214 nm; and
(iii) comparing the 2018 component content to the QS-21 main peak content to determine the 2018 component to QS-21 main peak ratio.

There is provided the use of a saponin extract of the present invention in the manufacture of a medicament. Additionally provided is a saponin extract of the present invention for use as a medicament, in particular as an adjuvant. Also provided is an adjuvant composition comprising a saponin extract of the present invention.

The saponin extracts of the present invention may be combined with further adjuvants, such as a TLR4 agonist, in particular lipopolysaccharide TLR4 agonists, such as lipid A derivatives, especially a monophosphoryl lipid A e.g. 3-de-O-acylated monophosphoryl lipid A (3D-MPL). monophosphoryl lipid A (3D-MPL). 3D-MPL is sold under the name 'MPL' by GlaxoSmithKline Biologicals N.A. and is referred throughout the document as 3D-MPL. See, for example, U.S. Pat. Nos. 4,436,727; 4,877,611; 4,866,034 and 4,912, 094. 3D-MPL can be produced according to the methods described in GB 2 220 211 A. Chemically it is a mixture of 3-deacylated monophosphoryl lipid A with 4, 5 or 6 acylated chains.

Other TLR4 agonists which may be of use in the present invention include Glucopyranosyl Lipid Adjuvant (GLA) such as described in WO2008/153541 or WO2009/143457 or the literature articles Coler R N et al. (2011) Development and Characterization of Synthetic Glucopyranosyl Lipid Adjuvant System as a Vaccine Adjuvant. PLoS ONE 6(1): e16333. doi: 10.1371/journal.pone.0016333 and Arias M A et al. (2012) Glucopyranosyl Lipid Adjuvant (GLA), a Synthetic TLR4 Agonist, Promotes Potent Systemic and Mucosal Responses to Intranasal Immunization with HIVgp140. PLoS ONE 7(7): e41144. doi:10.1371/journal- .pone.0041144. WO2008/153541 or WO2009/143457 are incorporated herein by reference for the purpose of defining TLR4 agonists which may be of use in the present invention.

A typical adult human dose of adjuvant will comprise a saponin extract at amounts between 1 and 100 ug per human dose. The saponin extract may be used at a level of about 50 ug. Examples of suitable ranges are 40-60 ug, suitably 45-55 ug or 49-51 ug, such as 50 ug. In a further embodiment, the human dose comprises saponin extract at a level of about 25 ug. Examples of lower ranges include 20-30 ug, suitably 22-28 ug or 24-26 ug, such as 25 ug. Human doses intended for children may be reduced compared to those intended for an adult (e.g. reduction by 50%).

The TLR4 agonists, such as a lipopolysaccharide, such as 3D-MPL, can be used at amounts between 1 and 100 ug per human dose. 3D-MPL may be used at a level of about 50 ug. Examples of suitable ranges are 40-60 ug, suitably 45-55 ug or 49-51 ug, such as 50 ug. In a further embodiment, the human dose comprises 3D-MPL at a level of about 25 ug. Examples of lower ranges include 20-30 ug, suitably 22-28 ug or 24-26 ug, such as 25 ug. Human doses intended for children may be reduced compared to those intended for an adult (e.g. reduction by 50%).

When both a TLR4 agonist and a saponin extract are present in the adjuvant, then the weight ratio of TLR4 agonist to saponin is suitably between 1:5 to 5:1, suitably 1:1. For example, where 3D-MPL is present at an amount of 50 ug or 25 ug, then suitably QS-21 may also be present at an amount of 50 ug or 25 ug per human dose.

Adjuvants may also comprise a suitable carrier, such as an emulsion (e.g. and oil in water emulsion) or liposomes.

Liposomes

The term 'liposome' is well known in the art and defines a general category of vesicles which comprise one or more lipid bilayers surrounding an aqueous space. Liposomes thus consist of one or more lipid and/or phospholipid bilayers and can contain other molecules, such as proteins or carbohydrates, in their structure. Because both lipid and aqueous phases are present, liposomes can encapsulate or entrap water-soluble material, lipid-soluble material, and/or amphiphilic compounds.

Liposome size may vary from 30 nm to several um depending on the phospholipid composition and the method used for their preparation.

The liposomes of use in the present invention suitably contain DOPC, or, consist essentially of DOPC and sterol (with saponin and optionally TLR4 agonist).

In the present invention, the liposome size will be in the range of 50 nm to 200 nm, especially 60 nm to 180 nm, such as 70-165 nm. Optimally, the liposomes should be stable and have a diameter of ~100 nm to allow convenient sterilization by filtration.

Structural integrity of the liposomes may be assessed by methods such as dynamic light scattering (DLS) measuring the size (Z-average diameter, Zav) and polydispersity of the liposomes, or, by electron microscopy for analysis of the structure of the liposomes. In one embodiment the average particle size is between 95 and 120 nm, and/or, the polydispersity (PdI) index is not more than 0.3 (such as not more than 0.2).

Further Excipients

In a further embodiment, a buffer is added to the composition. The pH of a liquid preparation is adjusted in view of the components of the composition and necessary suitability for administration to the subject. Suitably, the pH of a liquid mixture is at least 4, at least 5, at least 5.5, at least 5.8, at least 6. The pH of the liquid mixture may be less than 9, less than 8, less than 7.5 or less than 7. In other embodiments, pH of the liquid mixture is between 4 and 9, between 5 and 8, such as between 5.5 and 8. Consequently, the pH will suitably be between 6-9, such as 6.5-8.5. In a particularly preferred embodiment the pH is between 5.8 and 6.4. An appropriate buffer may be selected from acetate, citrate, histidine, maleate, phosphate, succinate, tartrate and TRIS. In one embodiment, the buffer is a phosphate buffer such as $Na/Na_2PO_4$, $Na/K_2PO_4$ or $K/K_2PO_4$.

The buffer can be present in the liquid mixture in an amount of at least 6 mM, at least 10 mM or at least 40 mM. The buffer can be present in the liquid mixture in an amount of less than 100 mM, less than 60 mM or less than 40 mM.

It is well known that for parenteral administration solutions should have a pharmaceutically acceptable osmolality to avoid cell distortion or lysis. A pharmaceutically acceptable osmolality will generally mean that solutions will have an osmolality which is approximately isotonic or mildly hypertonic. Suitably the compositions (when reconstituted, if presented in dried form) will have an osmolality in the range of 250 to 750 mOsm/kg, for example, the osmolality may be in the range of 250 to 550 mOsm/kg, such as in the range of 280 to 500 mOsm/kg. In a particularly preferred embodiment the osmolality may be in the range of 280 to 310 mOsm/kg. Osmolality may be measured according to techniques known in the art, such as by the use of a commercially available osmometer, for example the Advanced® Model 2020 available from Advanced Instruments Inc. (USA).

An "isotonicity agent" is a compound that is physiologically tolerated and imparts a suitable tonicity to a formulation to prevent the net flow of water across cell membranes that are in contact with the formulation. In some embodiments, the isotonicity agent used for the composition is a salt (or mixtures of salts), conveniently the salt is sodium chloride, suitably at a concentration of approximately 150 nM. In other embodiments, however, the composition comprises a non-ionic isotonicity agent and the concentration of sodium chloride in the composition is less than 100 mM, such as less than 80 mM, e.g. less than 50 mM, such as less 40 mM, less than 30 mM and especially less than 20 mM. The ionic strength in the composition may be less than 100 mM, such as less than 80 mM, e.g. less than 50 mM, such as less than 40 mM or less than 30 mM.

In a particular embodiment, the non-ionic isotonicity agent is a polyol, such as sucrose and/or sorbitol. The concentration of sorbitol may e.g. between about 3% and about 15% (w/v), such as between about 4% and about 10% (w/v). Adjuvants comprising an immunologically active saponin fraction and a TLR4 agonist wherein the isotonicity agent is salt or a polyol have been described in WO2012/080369.

Suitably, a human dose volume of between 0.05 ml and 1 ml, such as between 0.1 and 0.5 ml, in particular a dose volume of about 0.5 ml, or 0.7 ml. The volumes of the compositions used may depend on the delivery route and location, with smaller doses being given by the intradermal route. A unit dose container may contain an overage to allow for proper manipulation of materials during administration of the unit dose.

The ratio of saponin:DOPC will typically be in the order of 1:50 to 1:10 (w/w), suitably between 1:25 to 1:15 (w/w), and preferably 1:22 to 1:18 (w/w), such as 1:20 (w/w).

Suitably the saponin is presented in a less reactogenic composition where it is quenched with an exogenous sterol, such as cholesterol. Cholesterol is disclosed in the Merck Index, 13th Edn., page 381, as a naturally occurring sterol found in animal fat. Cholesterol has the formula ($C_{27}H_{46}O$) and is also known as (3β)-cholest-5-en-3-ol.

The ratio of saponin:sterol will typically be in the order of 1:100 to 1:1 (w/w), suitably between 1:10 to 1:1 (w/w), and preferably 1:5 to 1:1 (w/w). Suitably excess sterol is present, the ratio of saponin:sterol being at least 1:2 (w/w). In one embodiment, the ratio of saponin:sterol is 1:5 (w/w). In one embodiment, the sterol is cholesterol.

The amount of liposome (weight of lipid and sterol) will typically be in the range of 0.1 mg to 10 mg per human dose of a composition, in particular 0.5 mg to 2 mg per human dose of a composition.

In a particularly suitable embodiment, liposomes used in the invention comprise DOPC and a sterol, in particular cholesterol. Thus, in a particular embodiment, a composition used in the invention comprises saponin extract in the form of a liposome, wherein said liposome comprises DOPC and a sterol, in particular cholesterol.

Antigens

The adjuvants prepared according to the present invention may be utilised in conjunction with an immunogen or antigen. In some embodiments a polynucleotide encoding the immunogen or antigen is provided.

The adjuvant may be administered separately from an immunogen or antigen may be combined, either during manufacturing or extemporaneously, with an immunogen or antigen as an immunogenic composition for combined administration.

Consequently, there is provided a method for the preparation of an immunogenic composition comprising an immunogen or antigen, or a polynucleotide encoding the immunogen or antigen, said method comprising the steps of:
(i) preparing an adjuvant composition comprising a saponin extract of the present invention;
(ii) mixing the adjuvant with an immunogen or antigen, or a polynucleotide encoding the immunogen or antigen.

There is also provided the use of an adjuvant comprising a saponin extract of the present invention in the manufacture of a medicament. Suitably the medicament comprises an immunogen or antigen, or a polynucleotide encoding the immunogen or antigen. Further provided is an adjuvant comprising a saponin extract of the present invention for use as a medicament. Suitably the medicament comprises an immunogen or antigen, or a polynucleotide encoding the immunogen or antigen.

By the term immunogen is meant a polypeptide which is capable of eliciting an immune response. Suitably the immunogen is an antigen which comprises at least one B or T cell epitope. The elicited immune response may be an antigen specific B cell response, which produces neutralizing antibodies. The elicited immune response may be an antigen specific T cell response, which may be a systemic and/or a local response. The antigen specific T cell response may comprise a CD4+ T cell response, such as a response involving CD4+ T cells expressing a plurality of cytokines, e.g. IFNgamma, TNFalpha and/or IL2. Alternatively, or additionally, the antigen specific T cell response comprises a CD8+ T cell response, such as a response involving CD8+ T cells expressing a plurality of cytokines, e.g., IFNgamma, TNFalpha and/or IL2.

The antigen may be derived (such as obtained from) from a human or non-human pathogen including, e.g., bacteria, fungi, parasitic microorganisms or multicellular parasites which infect human and non-human vertebrates, or from a cancer cell or tumor cell.

In one embodiment the antigen is a recombinant protein, such as a recombinant prokaryotic protein.

In one embodiment, the antigen is derived from *Plasmodium* spp. (such as *Plasmodium falciparum*), *Mycobacterium* spp. (such as *Mycobacterium tuberculosis* (TB)), *Varicella Zoster* Virus (VZV), human respiratory syncytial virus, Human Immunodeficiency Virus (HIV), *Moraxella* spp. (such as *Moraxella catarrhalis*) or nontypable *Haemophilus influenzae* (ntHi). The antigen may comprise or consist of preparations derived from parasites that cause malaria such as *Plasmodium falciparum* or *Plasmodium vivax*.

In one embodiment, the antigen may be the *Plasmodium falciparum* circumsporozoite (CS) protein or a variant thereof. A suitable variant of the CS protein may be a variant wherein parts of the CS protein are in the form of a hybrid protein with the surface antigen S from hepatitis B (HBsAg). The CS variant antigen may e.g. be in the form of a hybrid protein comprising substantially all the C-terminal portion of the CS protein, four or more tandem repeats of the CS protein immunodominant region, and HBsAg. The hybrid protein may comprise a sequence which contains at least 160 amino acids and which is substantially homologous to the C-terminal portion of the CS protein, but devoid of the hydrophobic anchor sequence. The CS protein may be devoid of the last 12 amino-acids from the C terminal. Further, it may contain 4 or more e.g. 10 or more Asn-Ala-Asn-Pro tetrapeptide (NANP) repeat motifs.

The hybrid protein for use in the invention may be a protein which comprises a portion of the CS protein of *P. falciparum* substantially as corresponding to amino acids 207-395 of *P. falciparum* clone 3D7, derived from the strain NF54 fused in frame via a linear linker to the N-terminus of HBsAg. The linker may comprise a portion of preS2 from HBsAg. CS constructs suitable for use in the present invention are outlined in WO93/10152, which granted in the US as U.S. Pat. Nos. 5,928,902 and 6,169,171, both of which are incorporated by reference for the purpose of describing suitable proteins for use in the present invention.

A particular hybrid protein for use in the invention is the hybrid protein known as RTS (SEQ ID No. 1, also described in WO2015/150568, WO93/10152 (wherein it is denoted RTS*) and in WO98/05355, which consists of:
a methionine residue
three amino acid residues, Met Ala Pro
a stretch of 189 amino acids representing amino acids 207 to 395 of the CS protein of *P. falciparum* strain 3D7
an glycine residue
four amino acid residues, Pro Val Thr Asn, representing the four carboxy terminal residues of the hepatitis B virus (adw serotype) preS2 protein, and
a stretch of 226 amino acids, encoded by nucleotides 1653 to 2330, and specifying the S protein of hepatitis B virus (adw serotype).
RTS may be in the form of RTS,S mixed particles. RTS,S particles comprise two polypeptides, RTS and S, that may be synthesized simultaneously and spontaneously form composite particulate structures (RTS,S).

The antigen may comprise or consist of preparations derived from *Mycobacterium* spp., such as *Mycobacterium bovis* or *Mycobacterium tuberculosis*, in particular *Mycobacterium tuberculosis*.

Antigens of interest in the field of tuberculosis include Ry1196 and Rv0125. Rv1196 (described, for example, by the name Mtb39a in Dillon et al Infection and Immunity 1999 67(6): 2941-2950) is highly conserved, with 100% sequence identity across H37Rv, C, Haarlem, CDC1551, 94-M4241A, 98-R604INH-RIF-EM, KZN605, KZN1435, KZN4207, KZNR506 strains, the F11 strain having a single point mutation Q30K (most other clinical isolates have in excess of 90% identity to H37Rv). Rv0125 (described, for example, by the name Mtb32a in Skeiky et al Infection and Immunity 1999 67(8): 3998-4007) is also highly conserved, with 100% sequence identity across many strains. Full length Rv0125 includes an N-terminal signal sequence which is cleaved to provide the mature protein.

In one embodiment the antigen is derived from Rv1196, such as comprise, such as consist of, a sequence having at least 70% identity to SEQ ID No: 2, such as at least 80%, in particular at least 90%, especially at least 95%, for example at least 98%, such as at least 99%. Typical Rv1196 related antigens will comprise (such as consist of) a derivative of SEQ ID No: 2 having a small number of deletions, insertions and/or substitutions. Examples are those having deletions of up to 5 residues at 0-5 locations, insertions of up to 5 residues at 0-5 five locations and substitution of up to 20 residues. Other derivatives of Rv1196 are those comprising (such as consisting of) a fragment of SEQ ID No: 2 which is at least 200 amino acids in length, such as at least 250 amino acids in length, in particular at least 300 amino acids in length, especially at least 350 amino acids in length.

In one embodiment the antigen is derived from Rv0125, such as comprise, such as consist of, a sequence having at least 70% identity to SEQ ID No: 3, such as at least 80%, in particular at least 90%, especially at least 95%, for example at least 98%, such as at least 99%. Typical Rv0125 related antigens will comprise (such as consist of) a derivative of SEQ ID No: 3 having a small number of deletions, insertions and/or substitutions. Examples are those having deletions of up to 5 residues at 0-5 locations, insertions of up to 5 residues at 0-5 five locations and substitution of up to 20 residues. Other derivatives of Rv0125 are those comprising (such as consisting of) a fragment of SEQ ID No: 3 which is at least 150 amino acids in length, such as at least 200 amino acids in length, in particular at least 250 amino acids in length, especially at least 300 amino acids in length. Particular derivatives of Rv0125 are those comprising (such as consisting of) the fragment of SEQ ID No: 3 corresponding to residues 1-195 of SEQ ID No: 3. Further immunogenic derivatives of Rv0125 are those comprising (such as consisting of) the fragment of SEQ ID No: 3 corresponding to residues 192-323 of SEQ ID No: 3. Particularly preferred Rv0125 related antigens are derivatives of SEQ ID No: 3 wherein at least one (for example one, two or even all three) of the catalytic triad have been substituted or deleted, such that the protease activity has been reduced and the protein more easily produced—the catalytic serine residue may be deleted or substituted (e.g. substituted with alanine) and/or the catalytic histidine residue may be deleted or substituted and/or substituted the catalytic aspartic acid residue may be deleted or substituted. Especially of interest are derivatives of SEQ ID No: 3 wherein the catalytic serine residue has been substituted (e.g. substituted with alanine). Also of interest are Rv0125 related antigens which comprise, such as consist of, a sequence having at least 70% identity to SEQ ID No: 3, such as at least 80%, in particular at least 90%, especially at least 95%, for example at least 98%, such as at least 99% and wherein at least one of the catalytic triad have been substituted or deleted or those comprising, such as consisting of, a fragment of SEQ ID No: 3 which is at least 150 amino acids in length, such as at least 200 amino acids in length, in particular at least 250 amino acids in length, especially at least 300 amino acids in length and wherein at least one of the catalytic triad have been substituted or deleted. Further immunogenic derivatives of Rv0125 are those comprising (such as consisting of) the fragment of SEQ ID No: 3 corresponding to residues 192-323 of SEQ ID No: 3 wherein at least one (for example one, two or even all three) of the catalytic triad have been substituted or deleted. Particular immunogenic derivatives of Rv0125 are those comprising (such as consisting of) the fragment of SEQ ID No: 3 corresponding to residues 1-195 of SEQ ID No: 3 wherein the catalytic serine residue (position 176 of SEQ ID No: 3) has been substituted (e.g. substituted with alanine).

Suitably the antigen will comprise, such as consist of, a sequence having at least 70% identity to SEQ ID No. 4, such as at least 80%, in particular at least 90%, especially at least 95%, such as at least 98%, for example at least 99%. Typical M72 related antigens will comprise, such as consist of, a derivative of SEQ ID No: 4 having a small number of deletions, insertions and/or substitutions. Examples are those having deletions of up to 5 residues at 0-5 locations, insertions of up to 5 residues at 0-5 five locations and substitution of up to 20 residues. Other derivatives of M72 are those comprising, such as consisting of, a fragment of SEQ ID No: 4 which is at least 450 amino acids in length, such as at least 500 amino acids in length, such as at least 550 amino acids in length, such as at least 600 amino acids in length, such as at least 650 amino acids in length or at least 700 amino acids in length. As M72 is a fusion protein derived from the two individual antigens Rv0125 and Rv1196, any fragment of at least 450 residues will comprise a plurality of epitopes from the full length sequence (Skeiky et al J. Immunol. 2004 172: 7618-7628; Skeiky Infect. Immun. 1999 67(8): 3998-4007; Dillon Infect. Immun. 1999 67(6): 2941-2950).

M72 related antigen will comprise, such as consist of, a sequence having at least 70% identity to SEQ ID No. 4, such as at least 80%, in particular at least 90%, especially at least 95%, such as at least 98%, for example at least 99%.

Typical M72 related antigens will comprise, such as consist of, a derivative of SEQ ID No: 4 having a small number of deletions, insertions and/or substitutions. Examples are those having deletions of up to 5 residues at 0-5 locations, insertions of up to 5 residues at 0-5 five locations and substitution of up to 20 residues.

In particular embodiments the M72 related antigen will comprise residues 2-723 of SEQ ID No. 4, for example comprise (or consist of) SEQ ID No. 4 or comprise (or consist) of SEQ ID No. 5.

A further antigen that may be employed in accordance with the present invention is the tuberculosis antigen Rv1753 and variants thereof, such as described in WO2010010180, for example a Rv1753 sequence selected from Seq ID Nos: 1 and 2-7 of WO2010010180, in particular Seq ID No: 1. Another antigen of interest in the field of tuberculosis is Rv2386 and variants thereof, such as described in WO2010010179, for example a Rv2386 sequence selected from Seq ID Nos: 1 and 2-7 of WO2010010179, in particular Seq ID No: 1. Other antigens of interest in the field of tuberculosis include Rv3616 and variants thereof, such as described in WO2011092253, for example a natural Rv3616 sequence selected from Seq ID Nos: 1 and 2-7 of WO2011092253 or a modified Rv3616 sequence such as those selected from Seq ID Nos: 161 to 169, 179 and 180 of WO2011092253, in particular Seq ID No: 167. An additional antigen of interest is HBHA, such as described in WO97044463, WO03044048 and WO2010149657. The aforementioned patent applications WO2010010180, WO2010010179, WO2011092253, WO97044463, WO03044048 and WO2010149657 are incorporated herein by reference in their entirety for the purpose of defining antigens which may be of use in the present invention.

Other antigens of interest are those comprising (or consisting of): Rv1174, also known as DPV, such as described in SEQ ID No 8 of WO2010010177; Rv1793, also known as MTI or Mtb9.9, such as described in SEQ ID No 10 of WO2010010177; Rv2087, also known as MSL or Mtb9.8, such as described in SEQ ID No 9 of WO2010010177; Rv3616, also known as HTCC1 or Mtb40, such as described in SEQ ID Nos 1 and 2-7 WO2010010177 or SEQ ID Nos 161-169, 179 or 180 of WO2011092253; and/or Rv3874, also known as CFP10 or Tb38.1, such as described in SEQ ID No 9 of WO2010010177; or an immunogenic portion (such as at least 20, 50, 75 or 100 residues therefrom) or variant thereof (such as having at least 70%, 80%, 90% or 95% identity thereto). (WO2010010177 and WO2011092253 are incorporated herein by reference in their entirety for the purpose of defining antigens which may be of use in the present invention).

Tuberculosis antigens are most suitably utilised in the form of a polypeptide, but may alternatively be provided in the form of a polynucleotide encoding said polypeptide. A further antigen that may be employed in accordance with the present invention is derived from *Varicella zoster* virus (VZV). The VZV antigen for use in the invention may be any suitable VZV antigen or immunogenic derivative thereof, suitably being a purified VZV antigen. In one embodiment, the VZV antigen is the VZV glycoprotein gE (also known as gp1) or immunogenic derivative hereof. The wild type or full length gE protein consists of 623 amino acids comprising a signal peptide, the main part of the protein, a hydrophobic anchor region (residues 546-558) and a C-terminal tail. In one aspect, a gE C-terminal truncate (also referred to truncated gE or gE truncate) is used whereby the truncation removes 4 to 20 percent of the total amino acid residues at the carboxy terminal end. In a further aspect, the truncated gE lacks the carboxy terminal anchor region (suitably approximately amino acids 547-623 of the wild type sequence). In a further aspect gE is a truncated gE having the sequence of SEQ ID NO. 6. The gE antigen, anchorless derivatives thereof (which are also immunogenic derivatives) and production thereof is described in EP0405867 and references therein [see also Vafai A., Antibody binding sites on truncated forms of varicalla-zoster virus gpl(gE) glycoprotein, Vaccine 1994 12: 1265-9). EP192902 also describes gE and production thereof. Truncated gE is also described by Haumont et al. Virus Research (1996) vol 40, p 199-204, herein incorporated fully by reference. An adjuvanted VZV gE composition suitable for use in accordance of the present invention is described in WO2006/094756, i.e. a carboxyterminal truncated VZV gE in combination with adjuvant comprising QS-21, 3D-MPL and liposomes further containing cholesterol. Leroux-Roels I. et al. (J. Infect. Dis. 2012,206: 1280-1290) reported on a phase I/II clinical trial evaluating the adjuvanted VZV truncated gE subunit vaccine.

The antigen may comprise or consist of preparations derived from human respiratory syncytial virus (RSV). In certain favorable embodiments, a polypeptide antigen is an F protein polypeptide antigen from RSV. Particularly suitable as a polypeptide antigen component in the context of the are conformationally constrained F polypeptide antigens. Conformationally constrained F proteins have previously been described in both the prefusion (PreF) and postfusion (PostF) conformations. Such conformationally constrained F proteins typically comprise an engineered RSV F protein ectodomain. An F protein ectodomain polypeptide is a portion of the RSV F protein that includes all or a portion of the extracellular domain of the RSV F protein and lacks a functional (e.g., by deletion or substitution) transmembrane domain, which can be expressed, e.g., in soluble (not attached to a membrane) form in cell culture. Exemplary F protein antigens conformationally constrained in the prefusion conformation have been described in the art and are disclosed in detail in e.g., U.S. Pat. No. 8,563,002 (WO2009079796); US Published patent application No. US2012/0093847 (WO2010/149745); US2011/0305727 (WO2011/008974); US2014/0141037, WO2012/158613 and WO2014/160463 each of which is incorporated herein by reference for the purpose of illustrating prefusion F polypeptides (and nucleic acids), and methods of their production. Typically, the antigen is in the form of a trimer of polypeptides. Additional publications providing examples of F proteins in the prefusion conformation include: McLellan et al., Science, Vol. 340: 1113-1117; McLellan et al., Science, Vol 342: 592-598, and Rigter et al., PLOS One, Vol. 8: e71072, each of which can also be used in the context of the immunogenic combinations disclosed herein.

For example, an F protein polypeptide stabilized in the prefusion conformation typically includes an ectodomain of an F protein (e.g., a soluble F protein polypeptide) comprising at least one modification that stabilized the prefusion conformation of the F protein. For example, the modification can be selected from an addition of a trimerization domain (typically to the C terminal end), deletion of one or more of the furin cleavage sites (at amino acids ~105-109 and ~133-136), a deletion of the pep27 domain, substitution or addition of a hydrophilic amino acid in a hydrophobic domain (e.g., HRA and/or HRB). In an embodiment, the conformationally constrained PreF antigen comprises an F2 domain (e.g., amino acids 1-105) and an F1 domain (e.g., amino acids 137-516) of an RSV F protein polypeptide with no intervening furin cleavage site wherein the polypeptide further comprises a heterologous trimerization domain positioned C-terminal to the F1 domain. Optionally, the PreF antigen also comprises a modification that alters glycosylation (e.g., increases glycosylation), such as a substitution of one or more amino acids at positions corresponding to amino acids ~500-502 of an RSV F protein. When an oligomerization sequence is present, it is preferably a trimerization sequence. Suitable oligomerization sequences are well known in the art and include, for example, the coiled coil of the yeast GCN4 leucine zipper protein, trimerizing sequence from bacteriophage T4 fibritin ("foldon"), and the trimer domain of influenza HA. Additionally, or alternatively, the F polypeptide conformationally constrained in the prefusion conformation can include at least two introduced cysteine residues, which are in close proximity to one another and form a disulfide bond that stabilizes the prefusion RSV F polypeptide. For example, the two cysteines can be within about 10 Å of each other. For example, cysteines can be introduced at positions 165 and 296 or at positions 155 and 290. An exemplary PreF antigen is represented by SEQ ID NO:7. The antigen may comprise or consist of preparations derived from HIV. The antigen may be a HIV protein such as a HIV envelope protein. For example, the antigen may be a HIV envelope gp120 polypeptide or an immunogenic fragment thereof.

One suitable antigen is the HIV Glade B gp120 polypeptide of SEQ ID NO: 8 of the published application WO 2008/107370 (or an immunogenic fragment of this polypeptide). SEQ ID NO: 8 of WO 2008/107370 is incorporated by reference into this application. Suitable antigens also include a polypeptide comprising the V1V2 region of SEQ ID NO: 1 of the published application WO 2015/036061, or an immunogenic derivative or fragment of the V1V2 region of SEQ ID NO: 1. In addition, a polypeptide comprising the V1V2 region of SEQ ID NO: 5 of WO 2015/036061 or an immunogenic derivative or fragment of the V1V2 region of SEQ ID NO: 5 may be used as a suitable antigen. SEQ ID NO: 1 and SEQ ID NO: 5 of WO2015/036061 are incorporated by reference.

In another embodiment, the antigen may comprise two or more different HIV envelope gp120 polypeptide antigens (or immunogenic fragments of these polypeptides). Suitable antigens include the and HIV Glade C gp120 polypeptide antigens including TV1 gp120 (SEQ ID No: 8) and 1086.0 gp120 (SEQ ID No: 9).

Other suitable HIV antigens include Nef, Gag and Pol HIV proteins and immunogenic fragments thereof.

The composition may comprise non-typeable *Haemophilus influenzae* antigen(s) for example selected from: Fimbrin protein [(U.S. Pat. No. 5,766,608—Ohio State Research Foundation)] and fusions comprising peptides therefrom [e.g. LB1(f) peptide fusions; U.S. Pat. No. 5,843,464 (OSU) or WO 99/64067]; OMP26 [WO 97/01638 (Cortecs)]; P6 [EP 281673 (State University of New York)]; TbpA and/or TbpB; Hia; Hsf; Hin47; Hif; Hmw1; Hmw2; Hmw3; Hmw4; Hap; D15 (WO 94/12641); protein D (EP 594610); P2; and P5 (WO 94/26304); protein E (WO07/084053) and/or PilA (WO05/063802). The composition may comprise *Moraxella catarrhalis* protein antigen(s), for example selected from: OMP106 [WO 97/41731 (Antex) & WO 96/34960 (PMC)]; OMP21; LbpA &/or LbpB [WO 98/55606 (PMC)]; TbpA &/or TbpB [WO 97/13785 & WO 97/32980 (PMC)]; CopB [Helminen M E, et al. (1993) Infect. Immun. 61: 2003-2010]; UspA1 and/or UspA2 [WO 93/03761 (University of Texas)]; OmpCD; HasR (PCT/EP99/03824); PilQ (PCT/EP99/03823); OMP85 (PCT/EP00/01468); lipo06 (GB 9917977.2); lipo10 (GB 9918208.1); lipo11 (GB 9918302.2); lipo18 (GB 9918038.2); P6 (PCT/EP99/03038); D15 (PCT/EP99/03822); OmplA1 (PCT/EP99/06781); Hly3 (PCT/EP99/03257); and OmpE. In an embodiment, the composition may comprise non-typeable *H. influenzae* (NTHi) protein antigen(s) and/or *M. catarrhalis* protein antigen(s). The composition may comprise Protein D (PD) from *H. influenzae*. Protein D may be as described in WO91/18926. The composition may further comprise Protein E (PE) and/or Pilin A (PilA) from *H. Influenzae*. Protein E and Pilin A may be as described in WO2012/139225. Protein E and Pilin A may be presented as a fusion protein; for example LVL735 as described in WO2012/139225. For example, the composition may comprise three NTHi antigens (PD, PE and PilA, with the two last ones combined as a PEPiIA fusion protein). The composition may further comprise UspA2 from *M. catarrhalis*. UspA2 may be as described in WO2015125118, for example MC-009 ((M) (UspA2 31-564) (HH)) described in WO2015125118. For example, the composition may comprise three NTHi antigens (PD, PE and PilA, with the two last ones combined as a PEPiIA fusion protein) and one *M. catarrhalis* antigen (UspA2).

A plurality of antigens may be provided. For example, a plurality of antigens may be provided to strengthen the elicited immune response (e.g. to ensure strong protection), a plurality of antigens may be provided to broaden the immune response (e.g. to ensure protection against a range of pathogen strains or in a large proportion of a subject population) or a plurality of antigens may be provided to currently elicit immune responses in respect of a number of disorders (thereby simplifying administration protocols). Where a plurality of antigens are provided, these may be as distinct proteins or may be in the form of one or more fusion proteins.

Antigen may be provided in an amount of 0.1 to 100 ug per human dose. The present invention may be applied for use in the treatment or prophylaxis of a disease or disorder associated with one or more antigens described above. In one embodiment the disease or disorder is selected from malaria, tuberculosis, COPD, HIV and herpes.

The adjuvant may be administered separately from an immunogen or antigen, or may be combined, either during manufacturing or extemporaneously), with an immunogen or antigen as an immunogenic composition for combined administration.

Sterilisation

For parenteral administration in particular, compositions should be sterile. Sterilisation can be performed by various methods although is conveniently undertaken by filtration through a sterile grade filter. Sterilisation may be performed a number of times during preparation of an adjuvant or immunogenic composition, but is typically performed at least at the end of manufacture.

By "sterile grade filter" it is meant a filter that produces a sterile effluent after being challenged by microorganisms at a challenge level of greater than or equal to $1\times10^7/cm^2$ of effective filtration area. Sterile grade filters are well known to the person skilled in the art of the invention for the purpose of the present invention, sterile grade filters have a pore size between 0.15 and 0.25 um, suitably 0.18-0.22 um, such as 0.2 or 0.22 um.

The membranes of the sterile grade filter can be made from any suitable material known to the skilled person, for example, but not limited to cellulose acetate, polyethersulfone (PES), polyvinylidene fluoride (PVDF), polytetrafluoroethylene (PTFE). In a particular embodiment of the invention one or more or all of the filter membranes of the present invention comprise polyethersulfone (PES), in particular hydrophilic polyethersulfone. In a particular embodiment of the invention, the filters used in the processes described herein are a double layer filter, in particular a sterile filter with build-in prefilter having larger pore size than the pore size of the end filter. In one embodiment the sterilizing filter is a double layer filter wherein the pre-filter membrane layer has a pore size between 0.3 and 0.5 nm, such as 0.35 or 0.45 nm. According to further embodiments, filters comprise asymmetric filter membrane(s), such as asymmetric hydrophilic PES filter membrane(s). Alternatively, the sterilizing filter layer may be made of PVDF, e.g. in combination with an asymmetric hydrophilic PES pre-filter membrane layer. In light of the intended medical uses, materials should be of pharmaceutical grade (such as parenteral grade).

The teaching of all references in the present application, including patent applications and granted patents, are herein fully incorporated by reference. A composition or method or process defined as "comprising" certain elements is understood to encompass a composition, method or process (respectively) consisting of those elements. As used herein, 'consisting essentially of' means additional components may be present provided they do not alter the overall properties or function.

The invention will be further described by reference to the following, non-limiting, examples:

EXAMPLES

Example 1

HPLC of a Crude Aqueous Extract of *Quillaja saponaria* Molina

Crude bark extract was separated by reverse phase HPLC using a C4 column and gradient elution: mobile phase A—water/acetonitrile, 7/3 v/v with 0.15% trifluoroacetic acid; mobile phase B—acetonitrile with 0.15% trifluoroacetic acid. UV detection was at 214 nm.

Crude bark extract samples are diluted as necessary with purified water. PVPP (60 mg/mL) was added, the mixture stirred for approximately 30 minutes, and then centrifuged to separate the PVPP resin from the supernatant.

The supernatant was then analysed to provide an HPLC UV chromatogram.

FIG. 1 provides a representative example of an HPLC UV chromatogram. The peak corresponding to the QS-21 fraction is indicated.

Example 2

Analytical Methods

HPLC-UV
Equipment
Waters Alliance 2690/2695 separations module
Waters 2487 UV Detector or 2996 PDA Detector
Vydac Protein C4 4.6×250 mm 5 um column
Mobile Phase A (MPA)—0.15% trifluoroacetic acid in water/acetonitrile (70:30 v/v)
Mobile Phase B (MPB)—0.15% trifluoroacetic acid in acetonitrile
Linear Gradient Conditions:

| Time | Flow rate (ml/min) | % MPA | % MPB |
|---|---|---|---|
| 0 | 1 | 100 | 0 |
| 30 | 1 | 78.6 | 21.4 |
| 33 | 1 | 14.3 | 85.7 |

10 ul of sample is injected. UV detection is set at 214 nM. Using a blank injection for reference, integration of peaks in the chromatogram provides a total absorbance. Peak of interest (e.g. QS-21 main peak) is compared to total absorbance to determine peak content as a percentage.

UPLC-UV
Equipment
Waters Acquity UPLC
Waters Acquity Tunable UV Detector
Waters Acquity BEH C18 2.1×100 mm 1.7 um column
Mobile Phase A (MPA)—0.025% acetic acid in water/acetonitrile (70:30 v/v)
Mobile Phase B (MPB)—0.025% trifluoroacetic acid in water/acetonitrile (30:70 v/v)
Linear Gradient Conditions:

| Time | Flow rate (ml/min) | % MPA | % MPB |
|---|---|---|---|
| 0 | 0.5 | 88 | 12 |
| 10.2 | 0.5 | 65.7 | 34.3 |
| 11.2 | 0.5 | 10 | 90 |
| 13.2 | 0.5 | 10 | 90 |

Column temperature 28 degrees C. 10 ul of sample is injected. UV detection is set at 214 nM.
Using a blank injection for reference, integration of peaks in the chromatogram provides a total absorbance. Peak of interest (e.g. QS-21 main peak) is compared to total absorbance to determine peak content as a percentage.

UPLC-UV/MS
Equipment
Waters Acquity UPLC
Waters Acquity Tunable UV Detector
Waters Single-Quadrupole Mass Detector
Waters Acquity BEH C18 2.1×100 mm 1.7 um column
Mobile Phase A (MPA)—0.025% trifluoroacetic acid in water/acetonitrile/isopropyl alcohol (75:20:5 v/v)
Mobile Phase B (MPB)—0.025% trifluoroacetic acid in water/acetonitrile/isopropyl alcohol (10:72:18 v/v)
Linear Gradient Conditions:

| Time | Flow rate (ml/min) | % MPA | % MPB |
|---|---|---|---|
| 0 | 0.6 | 100 | 0 |
| 6.23 | 0.6 | 23 | 77 |

Test sample is prepared in 0.2% acetic acid in water/acetonitrile (70:30 v/v). Column temperature 55 degrees C. 10 ul of sample is injected. UV detection is set at 214 nM.

Although retention times vary slightly between runs, the QS-21 group is located at approximately 3.8 min (B-isomer) to approximately 4.5 minutes (prior to lyo impurity).

Using a blank injection for reference, integration of peaks in the chromatogram that elute after the solvent front between 0.5 and around 5.50 minutes and do not appear in the blank is undertaken.

The monoisotope of the most abundant species is identified by combining TIC over the entire chromatogram to create a combined spectrum.

Ratio of 2002 component to 1988 component is calculated by comparing the ion current associated with the 2002 component with the ion current associated with the 1988 component within the QS-21 main peak.

Figure 5:
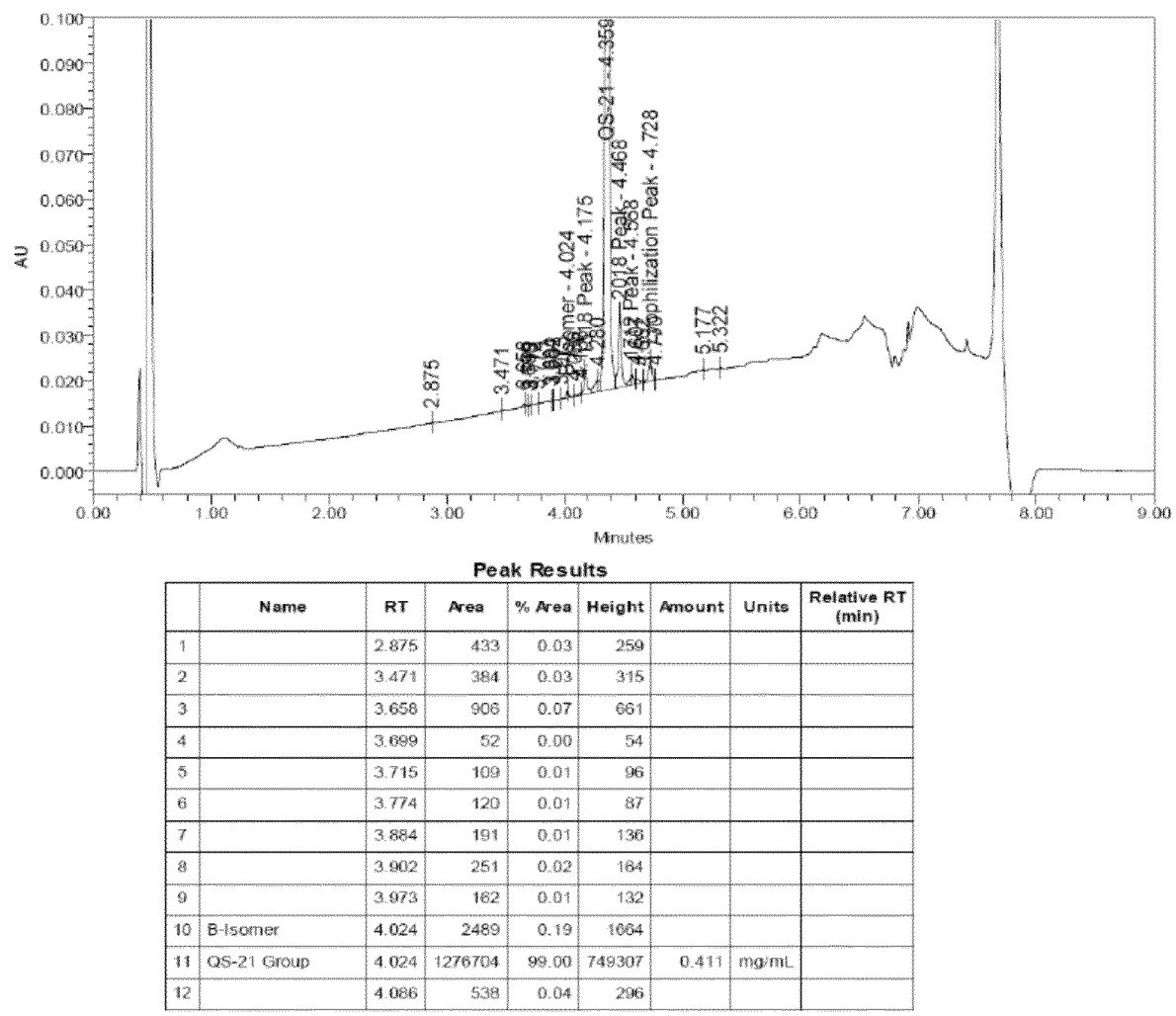

FIG. 5 provides an exemplary chromatogram of a saponin extract according to the present invention. FIG. 6 shows expanded detail of the region including the QS-21 group and lyo component.

Figure 7:
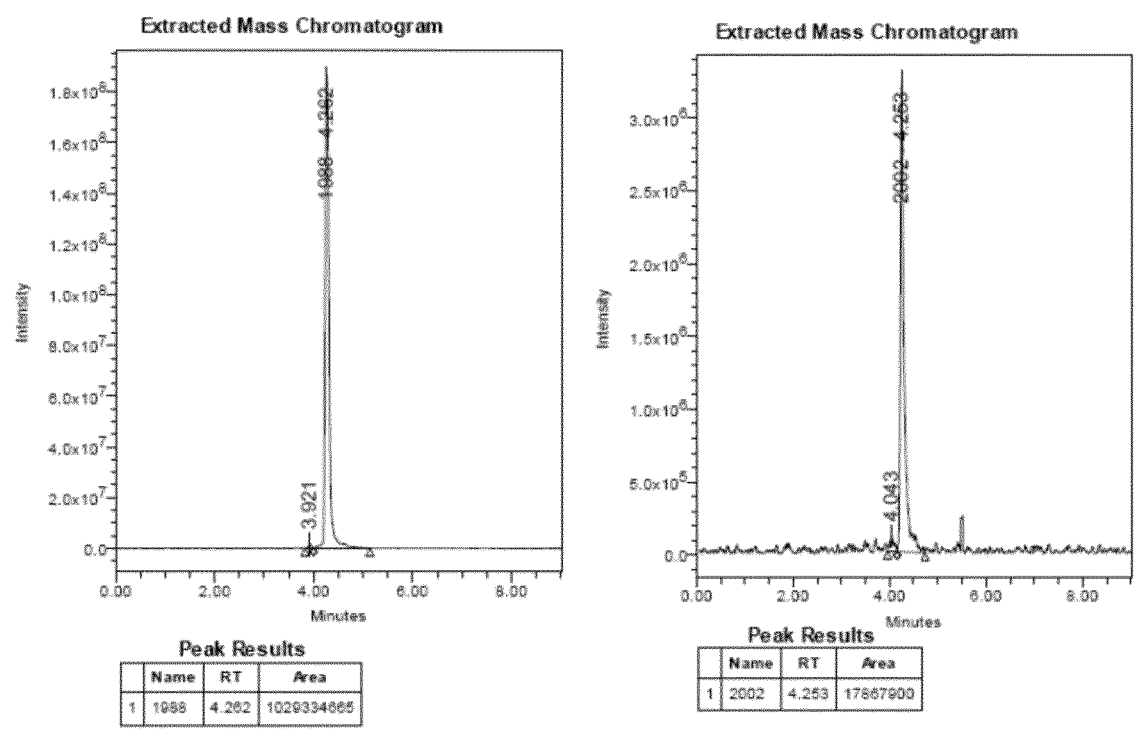
Figure 8:
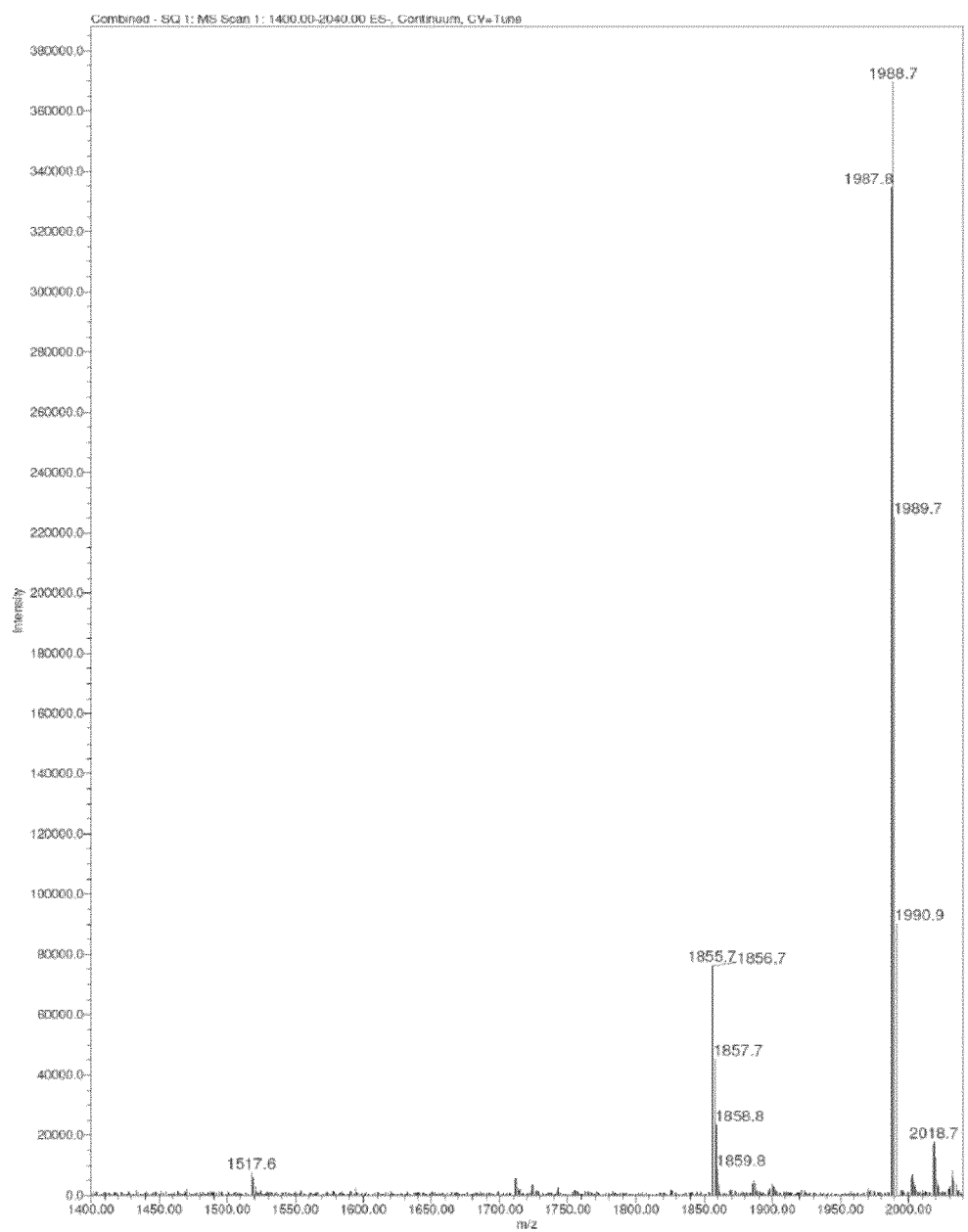

FIG. 7 provides an examplary extracted mass chromatograms for 1988 and 2002 molecular weight ions of a purified *Quillaja saponaria* Molina saponin extract.

Example 3

Purification of a Crude Aqueous Extract of *Quillaja saponaria* Molina

Crude aqueous extract of *Quillaja saponaria* Molina having a 2018 component to QS-21 main peak ratio of 0.064 or lower and a Preceding peak to QS-21 main peak ratio of 0.4 or lower, was treated with PVPP (1 kg PVPP per litre of crude aqueous extract). After adsorption the mixture was filtered to separate the PVPP and bound impurities from the liquor.

Figure 3:
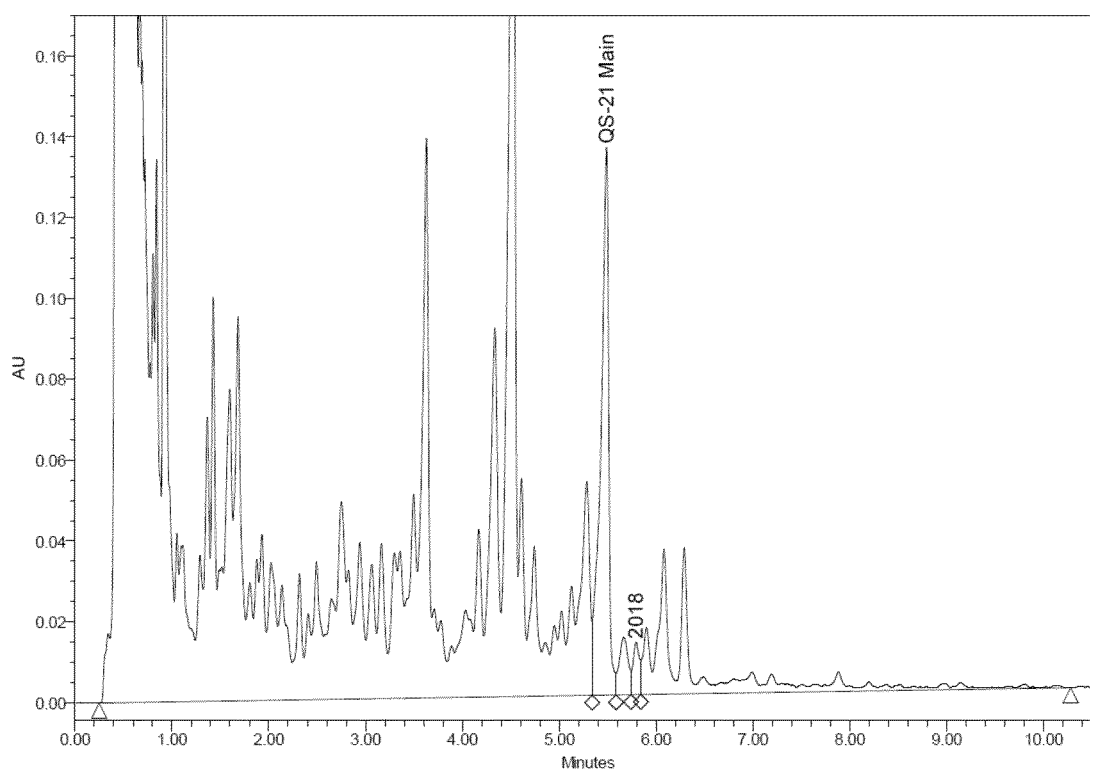

FIG. 2 provides an example HPLC-UV chromatogram for crude aqueous extract of Quillaja saponaria Molina (used for Preceding peak to QS-21 main peak ratio determination). FIG. 3 provides an example UPLC-UV chromatogram for crude aqueous extract of Quillaja saponaria Molina (used for 2018 component to QS-21 main peak ratio determination).

Filtered liquor was concentrated and further purified by ultrafiltration/diafiltration using a 30 kD Hellicon membrane.

Resulting permeate was purified by reverse phase chromatography using a polystyrene resin (Amberchrom XT20) and the following conditions:

| Step | Duration (min) | Initial % Eluent A | Initial % Eluent B | Final % Eluent A | Final % Eluent B |
|---|---|---|---|---|---|
| Injection + Rinse | 11.3 | 100% | 0% | 100% | 0% |
| Gradient Elution 1 | 3.0 | 100% | 0% | 71% | 29% |
| Gradient Elution 2 | 50.0 | 71% | 29% | 53% | 47% |
| Gradient Elution 3 | 3.0 | 53% | 47% | 0% | 100% |
| Regeneration | 10 | 0% | 100% | 0% | 100% |
| Gradient | 3.0 | 0% | 100% | 100% | 0% |
| Equilibration | 13.0 | 100% | 0% | 100% | 0% |

Eluent A: 5% Acetonitrile and 0.25% acetic acid
Eluent B: 90% Acetonitrile and 0.25% acetic acid
Column: 30 cm ID
Loading: 50-110 g per injection Fractions were pooled to provide polystyrene purified saponin extract with a composition:
% QS-21 main peak≥18% (by HPLC)
and
2018 component/QS-21 main peak ratio≤0.054 (by UPLC-UV).

Figure 4:
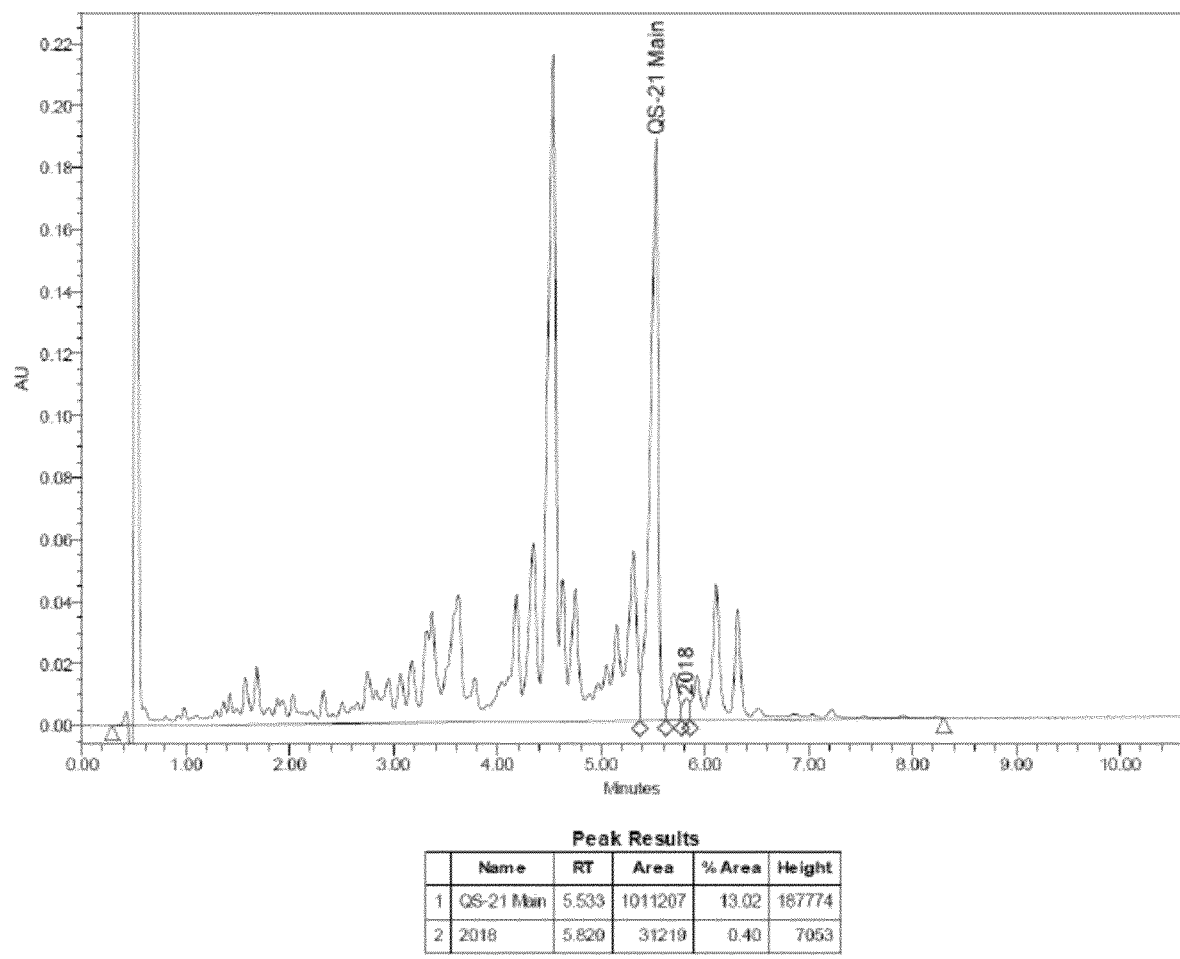

FIG. 4 provides an example UPLC-UV chromatogram for a polystyrene purified saponin extract pool.

The combined polystyrene purified fraction pool was further purified by reverse phase chromatography using a phenyl resin (EPDM) and the following conditions:

| Step | Duration (min) | % Eluent C | % Eluent B |
|---|---|---|---|
| Injection + Rinse | 2.0 | 100% | 0% |
| Isocratic Elution | 58.0 | 100% | 0% |
| Regeneration | 5.0 | 0% | 100% |
| Equilibration | 10.0 | 100% | 0% |

Eluent B: 90% Acetonitrile and 0.25% acetic acid
Eluent C: 35.2% acetonitrile and 0.25% acetic acid
Column: 45 cm ID
Loading: 13-21 g per injection Fractions were pooled to provide phenyl purified saponin extract with a composition:
% QS-21 group≥98.5%
% QS-21 main peak≥94.5%
% 2018 component≤2.7%
Main peak outside of the QS-21 group≤1% (by UPLC-UV/MS).

The combined phenyl purified saponin extract was concentrated by capture and release with reverse phase chromatography using a C8 resin (Lichroprep RP8) and the following conditions:

Loaded to column conditioned at 24% acetonitrile and 0.20% acetic acid.
Eluted with 60% acetonitrile and 0.20% acetic acid.
11 cm column
Load: 50-142 g per injection The C8 concentrated saponin extract was subjected to solvent exchange using ultrafiltration/diafiltration and a Pellicon 1 kDa membrane to reduce acetonitrile content below 21%.

The resulting solvent exchanged saponin extract was then lyophilised in a single step to provide the final product.

A series of process runs providing out of specification saponin extract were found to arise from the use of crude bark extract with excessive 2018 component content.

A plurality of runs according to the present invention, starting with a crude extract having a suitable 2018 component composition, were performed and on each occasion the final product was within specification.

The use of the process as described in Example 3 can consistently provide a purified saponin extract of Quillaja saponaria Molina having a defined content in terms of QS-21 main peak and 2018 component, such as consistently at least 93% of QS-21 main peak and 0.25-3% of 2018 and presenting a chromatographic profile comparable to the chromatograms shown in FIG. 5, FIG. 6 and FIG. 7.

Example 4

Immune Responses 6-8 week old female C57BL6 mice (5/group) were injected twice intramuscularly with a 14-day interval with gE antigen formulated with the adjuvant system AS01, a liposomal formulation comprising 3D-MPL and saponin extract prepared according to the present intention. A control group of 5 mice received gE with buffer alone.

Vaccine was prepared from three different lots of saponin extract and results are provided for two different dosage levels (0.4 and 0.1 ug 3D-MPL/QS-21 per animal corresponding to $\frac{1}{125}$ and $\frac{1}{500}$ of the human dose, respectively). Spleens were collected at D21 and sera at D21 and D28, and analysed for T and B cell responses, respectively.

ICS (Intracellular Cytokine Staining)

Spleens were collected and dissociated in RPMI medium using a potter tissue grinder (homogenizer) using two up and down strokes. Homogenized samples were transferred to 50 ml polypropylene tubes. Fibrous material was removed by filtration through a 100 uM nylon cell strainer. Cells were then washed, counted and re-suspended at $10^7$ cells per ml. ICS is the technology which allows the quantification of antigen specific T lymphocytes on the basis of cytokine production.

Lymphoid cells are re-stimulated overnight (O.N) in vitro with peptides gE or medium in the presence of a protein transport inhibitor (brefeldin A). These cells are then processed by conventional immunofluorescent procedure using fluorescent antibodies (extracellular staining: CD4, CD8; intracellular staining: TNF-alpha, IFN-gamma and IL2).

Figure 9:
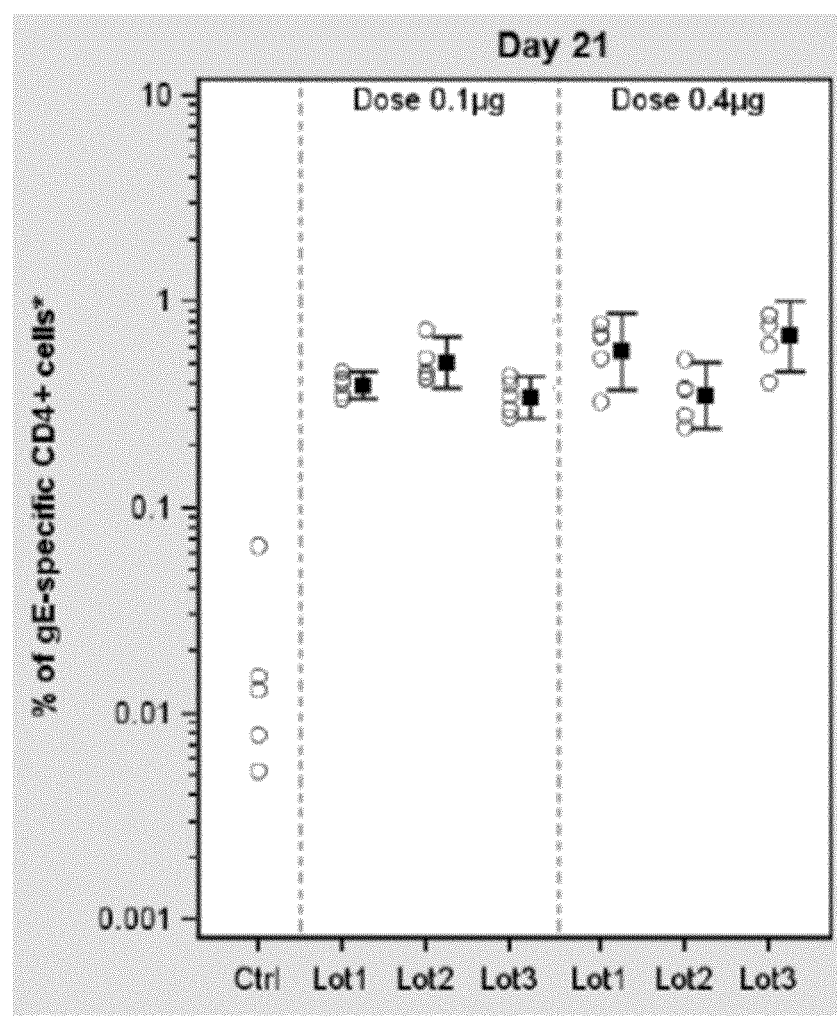

Results are expressed as a frequency of cytokine positive cells within CD4 cell populations after subtraction of the medium condition for each mouse. The data are presented for the population that showed expression of at least two cytokines (IL2, IFN-alpha or TNF-alpha). Results are shown in FIG. 9.

ELISA

Figure 10:
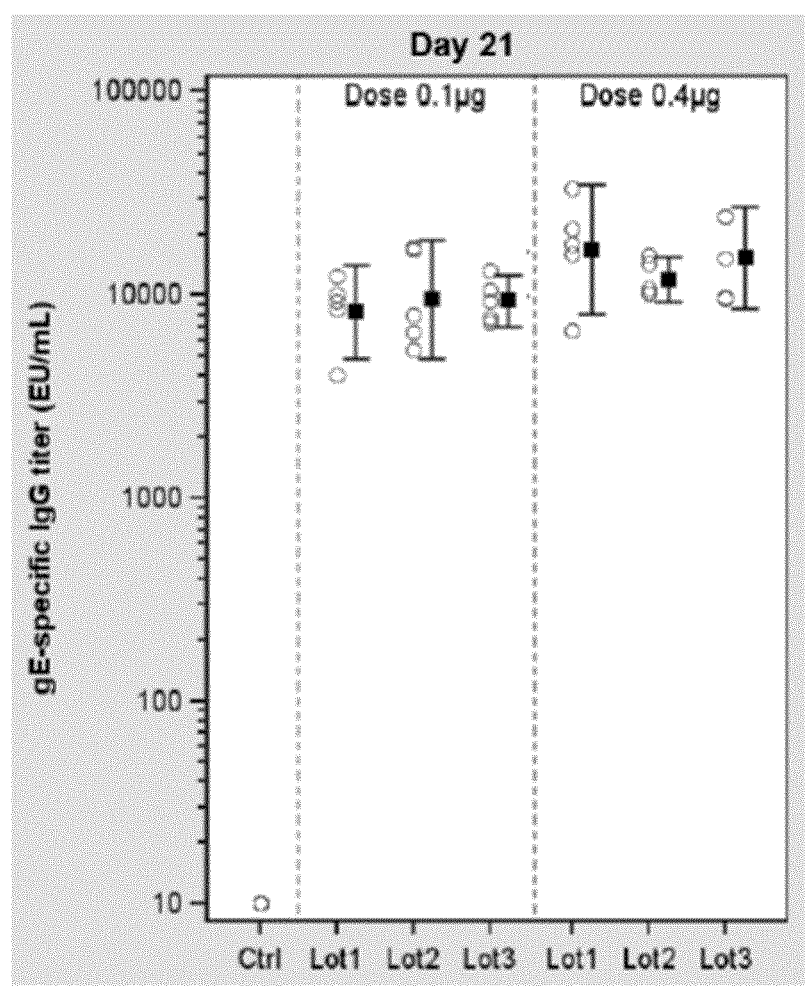
Figure 11:
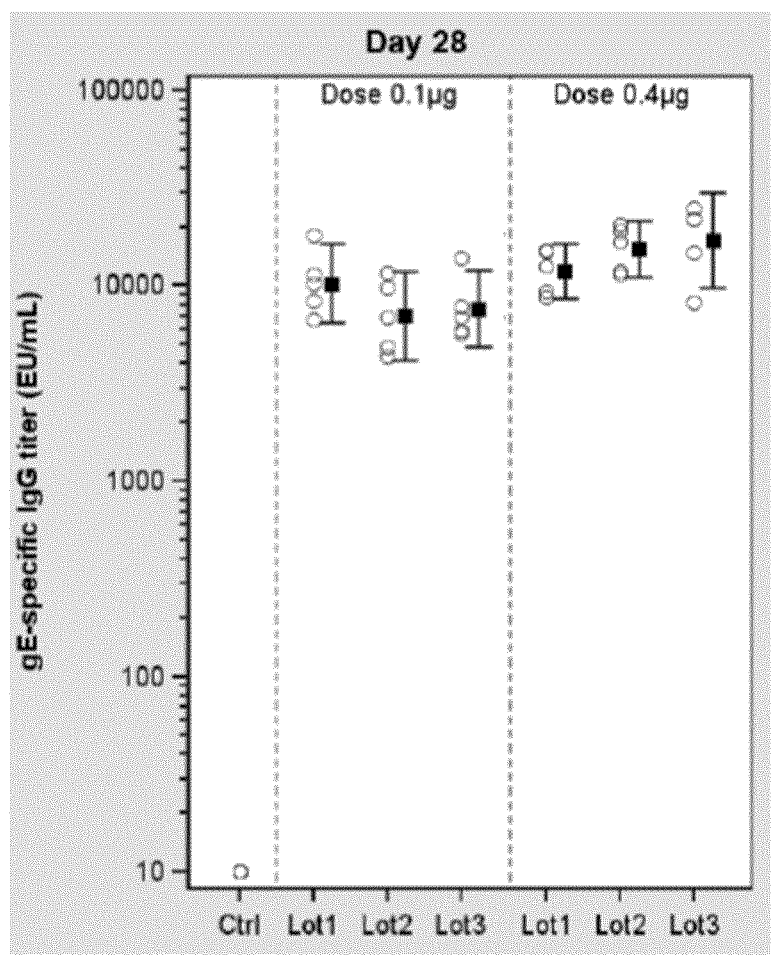

Anti-gE total IgG were measured by ELISA. 96 well-plates were coated with antigen overnight at 4° C. The plates were then washed and saturated with saturation buffer for 1 hour at 37° C. After, 100 ul of diluted mouse serum or standard or control was added and incubated for 1 h30 at 37° C. After wash, the plates were incubated for 1 hour at 37° C. with 100 µl anti mouse IgG-Biotinylated. After wash, the plates were incubated for 30 min at 37° C. with 100 ul Streptavidin-POD conjugate. After wash, 100 ul of TMB per well was added and the plates were kept in the dark at room temperature for 15 minutes. To stop the reaction, 100 ul of $H_2SO_4$ 0.4N was added per well. The absorbance was read at a wavelength of 450/630 nm by an Elisa plate reader. Results were calculated using the Softmax-Pro software. Results are shown in FIG. 10 (D21) and FIG. 11 (D28).

Conclusions

A consistent composition of saponin extract over different production lots resulted in immunological responses with a limited degree of variation.

BIBLIOGRAPHY

Dalsgaard et al. in 1974 ("Saponin adjuvants", Archiv. für die gesamte Virusforschung, Vol. 44, Springer Verlag, Berlin, p 243-254)

De Becker, G., V. Moulin, B. Pajak, C. Bruck, M. Francotte, C. Thiriart, J. Urbain, and M. Moser. 2000. The adjuvant monophosphoryl lipid A increases the function of antigen-presenting cells. *International immunology*. 12: 807-815.

Didierlaurent A. M., Collignon C., Bourguignon P., Wouters S., Fierens K., Fochesato M., Dendouga N., Langlet C., Malissen B., Lambrecht B. N., Garcon N., Van Mechelen M., and S. Morel. 2014 Enhancement of Adaptive Immunity by the Human Vaccine Adjuvant AS01 Depends on Activated Dendritic Cells *Journal of Immunology* 193(4): 1920-1930.

Didierlaurent et al, 2017 Adjuvant system AS01: helping to overcome the challenges of modern vaccines *Expert Reiews of Vaccines* 16(1): 55-63

Garcon, N., and M. Van Mechelen. 2011. Recent clinical experience with vaccines using MPL- and QS-21-containing adjuvant systems. *Expert review of vaccines*. 10: 471-486

Ismaili, J., J. Rennesson, E. Aksoy, J. Vekemans, B. Vincart, Z. Amraoui, F. Van Laethem, M. Goldman, and P. M. Dubois. 2002. Monophosphoryl lipid A activates both human dendritic cells and T cells. *Journal of immunology*. 168: 926-932.

Kensil, C. R., U. Patel, M. Lennick, and D. Marciani. 1991. Separation and characterization of saponins with adjuvant activity from *Quillaja saponaria* Molina cortex. *Journal of immunology*. 146: 431-437.

Kensil, C. R., and R. Kammer. 1998. QS-21: a water-soluble triterpene glycoside adjuvant. *Expert opinion on investigational drugs*. 7: 1475-1482.

Lambrecht, B. N., M. Kool, M. A. Willart, and H. Hammad. 2009. Mechanism of action of clinically approved adjuvants. *Current opinion in immunology*. 21: 23-29.

Leroux-Roels I. et al. J. Infect. Dis. 2012, 206: 1280-1290

Li, H., S. B. Willingham, J. P. Ting, and F. Re. 2008. Cutting edge: inflammasome activation by alum and alum's adjuvant effect are mediated by NLRP3. *Journal of immunology*. 181: 17-21.

Livingston, P. O., S. Adluri, F. Helling, T. J. Yao, C. R. Kensil, M. J. Newman, and D. Marciani. 1994. Phase 1 trial of immunological adjuvant QS-21 with a GM2 ganglioside-keyhole limpet haemocyanin conjugate vaccine in patients with malignant melanoma. *Vaccine*. 12: 1275-1280.

Ragupathi, G., J. R. Gardner, P. O. Livingston, and D. Y. Gin. 2011. Natural and synthetic saponin adjuvant QS-21 for vaccines against cancer. *Expert review of vaccines*. 10: 463-470

Martin, M., S. M. Michalek, and J. Katz. 2003. Role of innate immune factors in the adjuvant activity of monophosphoryl lipid A. *Infection and immunity*. 71: 2498-2507.

Marty-Roix, R. et al. Identification of QS-21 as an Inflammasome-activating Molecular Component of Saponin Adjuvants. *J. Biol. Chem*. 291, 1123-36 (2016)

Mata-Haro, V., C. Cekic, M. Martin, P. M. Chilton, C. R. Casella, and T. C. Mitchell. 2007. The vaccine adjuvant monophosphoryl lipid A as a TRIF-biased agonist of TLR4. *Science*. 316: 1628-1632.

Newman, M. J., J. Y. Wu, B. H. Gardner, K. J. Munroe, D. Leombruno, J. Recchia, C. R. Kensil, and R. T. Coughlin. 1992. Saponin adjuvant induction of ovalbumin-specific CD8+ cytotoxic T lymphocyte responses. *Journal of immunology*. 148: 2357-2362.

Soltysik, S., J. Y. Wu, J. Recchia, D. A. Wheeler, M. J. Newman, R. T. Coughlin, and C. R. Kensil. 1995. Structure/function studies of QS-21 adjuvant: assessment of triterpene aldehyde and glucuronic acid roles in adjuvant function. *Vaccine*. 13: 1403-1410.

The invention claimed is:

1. A method for the manufacture of a purified saponin extract comprising the steps of:
   (i) selecting a crude aqueous extract of *Quillaja saponaria* Molina having a 2018 component to QS-21 main peak ratio of 0.075 or lower;
   (ii) purifying the extract by polyvinylpyrollidone adsorption;
   (iii) purifying the extract by diafiltration, ultrafiltration or dialysis;
   (iv) purifying the extract by reverse phase chromatography using a polystyrene resin; and
   (v) purifying the extract by reverse phase chromatography using a phenyl resin.

2. The method of claim 1, wherein the crude aqueous extract of *Quillaja saponaria* Molina is an aqueous solution containing at least 1 g/L QS-21 main peak.

3. The method of claim 1, wherein the crude aqueous extract of *Quillaja saponaria* Molina is a bark extract.

4. An adjuvant composition comprising a saponin extract containing at least 93% QS-21 main peak and 0.25-3% 2018 component by UV adsorbance at 214 nm, wherein the adjuvant composition is a liposomal formulation.

5. An adjuvant composition comprising a saponin extract containing at least 93% QS-21 main peak and 0.25-3% 2018 component by UV adsorbance at 214 nm, wherein the adjuvant composition comprises a TLR4 agonist.

6. The adjuvant composition according to claim 5, wherein the TLR4 agonist is 3D-MPL.

7. An immunogenic composition comprising:
   a) an adjuvant composition comprising a saponin extract containing at least 93% QS-21 main peak and 0.25-3% 2018 component by UV adsorbance at 214 nm; and
   b) an immunogen or antigen, or a polynucleotide encoding the immunogen or antigen.

8. The immunogenic composition according to claim 7, wherein the antigen is derived from *Varicella zoster* virus.

9. The immunogenic composition according to claim 7, wherein the antigen is derived from human respiratory syncytial virus.

10. The immunogenic composition according to claim 8, wherein the antigen derived from *Varicella zoster* virus comprises the amino acid sequence of SEQ ID NO: 6.

11. The immunogenic composition according to claim 9, wherein the antigen derived from human respiratory syncytial virus comprises the amino acid sequence of SEQ ID NO: 7.

12. The adjuvant composition according to claim 4, wherein the monoisotope of the most abundant species of the saponin extract is 1987.9 m/z.

13. The adjuvant composition according to claim 4, wherein the saponin extract contains at least 98% QS-21 group by UV absorbance at 214 nm.

14. The adjuvant composition according to claim 4, wherein the saponin extract contains at least 98% QS-21 group, at least 93% QS-21 main peak, 0.25-3% 2018 component, 1% or less of largest peak outside the QS-21 group by UV absorbance at 214 nm and wherein the monoisotope of the most abundant species of the saponin extract is 1987.9 m/z.

15. The adjuvant composition according to claim 4, wherein the saponin extract contains at least 65% 1988 component by UV absorbance at 214 nm and by relative ion abundance.

16. The adjuvant composition according to claim 4, wherein the saponin extract contains at least 5% 1856 component by UV absorbance at 214 nm and by relative ion abundance.

17. The adjuvant composition according to claim 4, wherein the saponin extract contains at least 0.5% 2002 component by UV absorbance at 214 nm and by relative ion abundance.

18. The adjuvant composition according to claim 4, wherein the saponin extract contains at least 1% 2018 component by UV absorbance at 214 nm.

19. The adjuvant composition according to claim 5, wherein the monoisotope of the most abundant species of the saponin extract is 1987.9 m/z.

20. The adjuvant composition according to claim 5, wherein the saponin extract contains at least 98% QS-21 group by UV absorbance at 214 nm.

21. The adjuvant composition according to claim 5, wherein the saponin extract contains at least 98% QS-21 group, at least 93% QS-21 main peak, 0.25-3% 2018 component, 1% or less of largest peak outside the QS-21 group by UV absorbance at 214 nm and wherein the monoisotope of the most abundant species of the saponin extract is 1987.9 m/z.

22. The adjuvant composition according to claim 5, wherein the saponin extract contains at least 65% 1988 component by UV absorbance at 214 nm and by relative ion abundance.

23. The adjuvant composition according to claim 5, wherein the saponin extract contains at least 5% 1856 component by UV absorbance at 214 nm and by relative ion abundance.

24. The adjuvant composition according to claim 5, wherein the saponin extract contains at least 0.5% 2002 component by UV absorbance at 214 nm and by relative ion abundance.

25. The adjuvant composition according to claim 5, wherein the saponin extract contains at least 1% 2018 component by UV absorbance at 214 nm.

26. The immunogenic composition according to claim 7, wherein the monoisotope of the most abundant species of the saponin extract is 1987.9 m/z.

27. The immunogenic composition according to claim 7, wherein the saponin extract contains at least 98% QS-21 group by UV absorbance at 214 nm.

28. The immunogenic composition according to claim 7, wherein the saponin extract contains at least 98% QS-21 group, at least 93% QS-21 main peak, 0.25-3% 2018 component, 1% or less of largest peak outside the QS-21 group by UV absorbance at 214 nm and wherein the monoisotope of the most abundant species of the saponin extract is 1987.9 m/z.

29. The immunogenic composition according to claim 7, wherein the saponin extract contains at least 65% 1988 component by UV absorbance at 214 nm and by relative ion abundance.

30. The immunogenic composition according to claim 7, wherein the saponin extract contains at least 5% 1856 component by UV absorbance at 214 nm and by relative ion abundance.

31. The immunogenic composition according to claim 7, wherein the saponin extract contains at least 0.5% 2002 component by UV absorbance at 214 nm and by relative ion abundance.

32. The immunogenic composition according to claim 7, wherein the saponin extract contains at least 1% 2018 component by UV absorbance at 214 nm.

* * * * *